United States Patent
Habashita et al.

(10) Patent No.: US 7,732,442 B2
(45) Date of Patent: Jun. 8, 2010

(54) CHEMOKINE RECEPTOR ANTAGONIST AND MEDICAL USE THEREOF

(75) Inventors: Hiromu Habashita, Mishima-gun (JP); Hiroshi Ochiai, Mishima-gun (JP); Natsuko Tokuda, Mishima-gun (JP); Shiro Shibayama, Tsukuba (JP); Noriki Watanabe, Tsukuba (JP); Takaki Komiya, Tsukuba (JP); Kazuhiko Takeda, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 522 days.

(21) Appl. No.: 10/570,813

(22) PCT Filed: Sep. 3, 2004

(86) PCT No.: PCT/JP2004/013186

§ 371 (c)(1),
(2), (4) Date: Mar. 6, 2007

(87) PCT Pub. No.: WO2005/023771

PCT Pub. Date: Mar. 17, 2005

(65) Prior Publication Data

US 2007/0254886 A1 Nov. 1, 2007

(30) Foreign Application Priority Data

Sep. 5, 2003 (JP) .............................. 2003-314248
May 19, 2004 (JP) .............................. 2004-149683

(51) Int. Cl.
*A61K 31/538* (2006.01)
(52) U.S. Cl. .................... 514/230.5; 544/105; 546/122; 546/139; 546/152; 546/297
(58) Field of Classification Search .................. 546/297
See application file for complete search history.

(56) References Cited

U.S. PATENT DOCUMENTS

| 5,403,930 | A * | 4/1995 | Agback et al. ............... 544/235 |
| 6,448,290 | B1 * | 9/2002 | Ohuchida et al. ............ 514/471 |
| 2006/0004010 | A1 | 1/2006 | Habashita et al. | |

FOREIGN PATENT DOCUMENTS

| WO | 93/10094 A1 | 5/1993 |
| WO | 0198273 A1 | 12/2001 |
| WO | 02/30358 A2 | 4/2002 |
| WO | 02076457 A1 | 10/2002 |
| WO | 03018566 A1 | 3/2003 |
| WO | 03018576 A1 | 3/2003 |
| WO | 03051870 A1 | 6/2003 |
| WO | 03059893 A1 | 7/2003 |
| WO | 2004005295 A1 | 1/2004 |
| WO | 2004007472 A1 | 1/2004 |
| WO | 2005/021513 A1 | 3/2005 |
| WO | 2006/002284 A1 | 1/2006 |

OTHER PUBLICATIONS

West, Anthony R., Solid State Chemistry and its Applications, Wiley, New York, 1988, pp. 358 and 365.*
Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
International Serach Report dated Nov. 22, 2004.
Supplemental European Search Report issued in European Patent Application No. 04772925.6-2101/1661889; dated Jul. 6, 2009.

* cited by examiner

*Primary Examiner*—James O Wilson
*Assistant Examiner*—Brian McDowell
(74) *Attorney, Agent, or Firm*—Sughrue Mion, PLLC

(57) ABSTRACT

The present invention relates to a compound represented by formula (I), a salt thereof, an N-oxide thereof, a solvate thereof or a prodrug thereof, and medical use thereof (the symbols in the formula are as described in the specification).

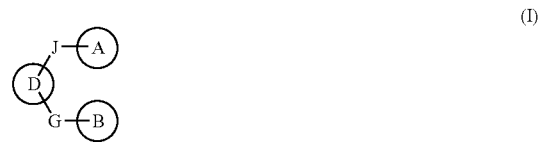

(I)

The compound represented by formula (I) has chemokine receptor (especially in CCR4 and/or CCR5) antagonistic activity. Therefore it is useful for prevention and/or treatment of a chemokine receptor-mediated disease such as inflammatory and/or allergic diseases [systemic inflammatory response syndrome (SIRS), anaphylaxis, anaphylactoid reaction, allergic angiitis, transplant rejection reaction, hepatitis, nephritis, nephropathy, pancreatitis, rhinitis, arthritis, inflammatory ocular disease, inflammatory bowel disease, disease in cerebro and/or circulatory system, respiratory disease, dermatosis, autoimmune disease, and the like], infection [viral disease (human immunodeficiency virus infection, acquired immunodeficiency syndrome, SARS, etc.), and the like], and the like.

3 Claims, No Drawings

CHEMOKINE RECEPTOR ANTAGONIST AND MEDICAL USE THEREOF

This is a national stage application under 35 U.S.C. 371 of PCT/JP04/013186 filed on Sep. 3, 2004, which claims priority from Japanese patent application 2003-314248 filed on Sep. 5, 2003, and Japanese patent application 2004-149683 filed on May 19, 2004, all of which are incorporated herein by reference.

TECHNICAL FIELD

The present invention relates to a compound having chemokine receptor (especially in CCR4 and/or CCR5) antagonistic activity which is useful as a medicament, a process for preparation of the same, and use thereof.

BACKGROUND ART

Chemokine is known as a basic protein having endogenous leukocyte chemotactic and activating activities and strong heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found locally and differentiation, maturation and the like of lymphocytes are carried out at certain specific sites. That is, various necessary cells migrate into certain specified sites and accumulate therein to cause a series of inflammations and immune responses. Accordingly, migration of cells is also an indispensable phenomenon to lead to the immune system in addition to differentiation, proliferation and death of cells.

Migration of hemocytes in the living body starts firstly in the development stage by the shift of hematopoiesis started in the AGM (Aorta-Gonad-Mesonephros) region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which is subjected to clone selection migrates into secondary lymphoid tissues and takes part in an immune response in the periphery. The Langerhans's cell of the skin activated and differentiated by capturing an antigen migrates into the T cell region of a topical lymph node and activates naive T cell therein as a dendritic cell. The memory T cell demonstrates its homing ability again into the lymph node via lymphatic and blood vessels. Also, B cell, T cell in the intestinal epithelium, γδT cell, NKT cell and dendritic cell migrate from bone marrow without passing through the thymus gland and differentiate to take part in an immune response.

Chemokine is deeply related to the migration of these various cells. For example, CCR4 which is a receptor for MDC (Macrophage-derived chemokine) and TARC (Thymus and activation-regulated chemokine) is expressed in Th2 cell (see *J. Immunol.*, 161, 5111 (1998)), and is known to play an important role in the migration of Th2 cell into topical sites where immune and inflammatory responses related to the Th2 cell is induced. In a mouse OVA-induced airway hypersensitivity model, an anti-MDC antibody suppressed the number of eosinophils accumulated in the lung interstitium, and suppressed airway hypersensitivity (see *J. Immunol.*, 163, 403 (1999)). In a mouse OVA-induced airway hypersensitivity model, anti-TARC antibody suppressed infiltration of eosinophils and lymphocytes into the airway as well as airway hypersensitivity (see *J. Immunol*, 166, 2055 (2001)). In the investigation with Nc/Nga mouse, it was recognized that amounts of TARC and MDC have increased in the atopic dermatitis-like lesion site (see *J. Clin. Invest.*, 104, 1097 (1999)). For CCR4 relation to human pathologic conditions, the number of CCR4 positive memory-T lymphocyte in peripheral blood increased depending on severity of dermatitis (see *J. Allergy Clin. Immunol.*, 107, 353 (2001)), and the amount of TARC in the serum was also correlated to the severity in the atopic dermatitis patients (see *J. Allergy Clin. Immunol.*, 107, 535 (2001)). The amount of TARC in the serum and the induced sputum also increased in the asthma patients (see *Allergy*, 57, 173 (2002)). MDC concentration in the blood was high in Th2 diseases such as atopic dermatitis and Sezary syndrome (see *Eur. J. Immunol.*, 30, 201 (2000)).

There have been many reports suggesting correlation with other inflammatory diseases than allergic diseases, and CCR4 positive cell was accumulated selectively in the affected site of Lupus nephritis (see *Arthritis Rheum.*, 46, 735 (2002)). Expression of TARC and MDC was high in the affected site of Crohn's disease (see *Eur. Cytokine Netw.*, 12, 468 (2001)). CCR4 expression rose in the peripheral blood CD4 positive cells of systemic lupus erythematodes patients as compared with healthy persons (see *J. Leuko., Biol.*, 70, 749 (2001)).

Furthermore, it has been known that chemokine play various roles in immune responses in addition to the migration of various cells. In the investigation with CCR4 deficient mouse, it was recognized that lethality by high dose LPS shock reduced as compared with wild type, and further, amounts of TNFα, IL-1β and MIP-1α also reduced in the blood after administration of LPS. Furthermore, in a rat fulminant hepatitis model (P.acnes+LPS), an anti-TARC antibody suppressed increase of the amount of ALT in the blood and increase of the expression amounts of TNFα and FasL in the liver and also improved lethality of the rats (see *J. Clin. Invest.*, 102, 1933 (1998)). It was shown that CCR4 contributes to the binding of activated T cells and dendritic cells (see *J. Immunol.*, 167, 4791 (2001)). Furthermore, TARC and MDC caused platelet aggregation mediated by CCR4 (see *Thrombosis Research*, 101, 279 (2001)), which is one of various physiological activities of chemokines and chemokine receptors.

Based on the above, chemokines and chemokine receptors are greatly related to the control of inflammation and/or immune responses through a mechanism in which they are expressed at certain specified periods in variously specific cells and its effector cells are accumulated in a region where chemokine is produced.

Acquired immunodeficiency syndrome (called AIDS) which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with *pneumocystis carinii* pneumonia and the like various opportunistic infections. Such conditions are the onset of AIDS, and it is well known that they induce and worsen Kaposi sarcoma and the like malignant tumors.

As the recent preventive and therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell*, 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

In 1996, a cell membrane protein called Fusin was identified as a factor other than the CD4 molecule, which is related to the HIV infection (*Science*, 272, 872 (1996)). It was confirmed that this Fusin molecule is a receptor (namely, CXCR4) of stromal derived factor-1 (hereinafter referred to as "SDF-1"). In addition, it was confirmed also in vitro that the SDF-1 specifically inhibits infection of T cell tropic (X4) HIV (*Nature*, 382, 829 (1996), *Nature*, 382, 833 (1996)). That is, it is considered that the HIV infection was inhibited by the binding of SDF-1 to CXCR4 preceding HIV, thereby depriving HIV of a foothold for infecting cells.

Also at that time, it was discovered that another chemokine receptor CCR5, which is a receptor of RANTES, MIP-1α and MIP-1β, is also used at the time of the infection with a macrophage tropic (R5) HIV (*Science*, 272, 1955 (1996)).

Accordingly, substances which can compete with CXCR4 and CCR5 for HIV, or which can bind to HIV virus thus causing the virus unable to bind to CXCR4 and CCR5, could become HIV infection inhibitors. Also, there is a case in which a low molecular compound initially discovered as an HIV infection inhibitor was actually a CXCR4 antagonist (*Nature Medicine*, 4, 72 (1998)).

Therefore, it is considered to use chemokine receptor antagonist as a preventive and/or therapeutic agent for inflammatory and/or allergic disease [for example, systemic inflammatory response syndrome (SIRS), anaphylaxis or anaphylactoid reaction, allergic vasculitis, transplant rejection reaction, hepatitis, nephritis, nephropathy, pancreatitis, rhinitis, arthritis, inflammatory ocular disease (e.g., conjunctivitis, etc.), inflammatory bowel disease (e.g., ulcerative colitis, Crohn's disease, eosinophilic gastroenteropathy, etc.), disease in cerebro and/or circulatory system (e.g., arteriosclerosis, thrombosis, ischemic/reperfusion disorder, restenosis, infarction, etc.), respiratory disease (e.g., acute respiratory distress syndrome (ARDS), asthma, pulmonary fibrosis, allergic broncho-pulmonary aspergillosis, etc.), dermatosis (e.g., dermatitis such as atopic dermatitis, psoriasis, contact dermatitis, eczema, urticaria and pruritus, and the like), autoimmune disease (e.g., multiple sclerosis, chronic articular rheumatism, systemic lupus erythematodes, Type I diabetes mellitus, glomerular nephritis, Sjoegren's syndrome, etc.), and the like], metabolism and/or endocrine system disease (e.g., diabetes mellitus, etc.), cancer disease [for example, malignant neoplasm such as leukemia, cancer and cancer metastasis, etc.), and the like], infection [for example, viral disease (e.g., human immunodeficiency virus infection, acquired immunodeficiency syndrome, SARS, etc.), and the like], and the like.

Until now, some compounds were disclosed as low molecular weight compounds having chemokine receptor antagonistic activity (see the specification of WO02/030357, WO02/030358, WO02/094264, WO03/051870, WO03/059893 and WO03/099773).

Also, the following sulfonamide compounds are known.

For example, the compound represented by formula (Y):

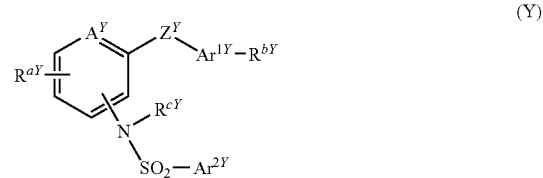

(Y)

is known to be useful as an antiulcer agent (WO99/050237).

Also, the compound represented by formula (W):

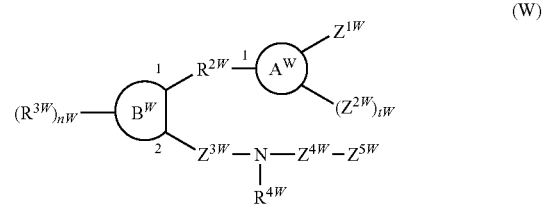

(W)

is known to be useful as an antagonist and/or an agonist of PGE2 (WO98/027053). In this specification, 4-({[3-[(phenylsulfonyl)amino]-5-(trifluoromethyl)pyridin-2-yl]oxy}methyl)benzoic acid is disclosed specifically (CAS No.: 209687-70-7).

Moreover, sulfonamide compounds of the following (1) to (17) are known:

(1) N-[3-(benzyloxy)pyridin-2-yl]-4-(trifluoromethoxy)benzenesulfonamide (CAS No.: 497060-26-1), (2) N-[3-(benzyloxy)pyridin-2-yl]-4-fluorobenzenesulfonamide (CAS No.: 486441-58-1), (3) N-{3-[(3,4-dichlorobenzyl)oxy]pyridin-2-yl}-4-propylbenzenesulfonamide (CAS No.: 307352-98-3), (4) N-{3-[(3,4-dichlorobenzyl)oxy]pyridin-2-yl}-4-methoxybenzenesulfonamide (CAS No.: 307352-95-0), (5) 4-bromo-N-{3-[(3,4-dichlorobenzyl)oxy]pyridin-2-yl}benzenesulfonamide (CAS No.: 307352-94-9), (6) 4-chloro-N-{3-[(3,4-dichlorobenzyl)oxy]pyridin-2-yl}benzenesulfonamide (CAS No.: 307352-93-8), (7) N-{3-[(3,4-dichlorobenzyl)oxy]pyridin-2-yl}-4-methylbenzenesulfonamide (CAS No.: 307352-92-7), (8) N-{3-[(3,5-difluorobenzyl)oxy]pyridin-2-yl}-3,4-difluorobenzenesulfonamide (CAS No.: 307352-33-6), (9) N-{3-[(3,5-difluorobenzyl)oxy]pyridin-2-yl}-2-(trifluoromethyl)benzenesulfonamide (CAS No.: 307352-29-0),

(10) N-{3-[(3,5-difluorobenzyl)oxy]pyridin-2-yl}-4-pentylbenzenesulfonamide (CAS No.: 307352-21-2),

(11) N-{3-[(3,5-difluorobenzyl)oxy]pyridin-2-yl}-4-methylbenzenesulfonamide (CAS No.: 307352-20-1),

(12) N-{3-[(3,5-difluorobenzyl)oxy]pyridin-2-yl}-4-isopropylbenzenesulfonamide (CAS No.: 307352-11-0),

(13) N-{3-[(3,5-difluorobenzyl)oxy]pyridin-2-yl}-4-propyl-benzenesulfonamide (CAS No.: 307352-10-9),
(14) 3-chloro-N-{3-[(3,5-difluorobenzyl)oxy]pyridin-2-yl}benzenesulfonamide (CAS No.: 307352-08-5),
(15) N-{3-[(3,5-difluorobenzyl)oxy]pyridin-2-yl}-4-methoxybenzenesulfonamide (CAS No.: 307352-07-4),
(16) N-{3-[(3,4-dichlorobenzyl)oxy]pyridin-2-yl}-4-isopropylbenzenesulfonamide (CAS No.: 307352-01-8), and
(17) N-{3-[(3,4-dichlorobenzyl)oxy]pyridin-2-yl}benzenesulfonamide (CAS No.: 307351-98-0).

DISCLOSURE OF THE INVENTION

The problem to be solved by the present invention is to provide a compound useful as a preventive and/or therapeutic agent for asthma, pulmonary fibrosis, atopic dermatitis, human immunodeficiency virus infection, acquired immunodeficiency syndrome and/or transplant rejection reaction, which is excellent in oral absorption, can be safely administered, and has an ability to antagonize chemokine receptor The present inventors have intensively studied to find a compound having chemokine receptor (especially in CCR4 and/or CCR5) antagonistic activity, and as a result, have found that the purpose is achieved by the compound of the present invention represented by formula (I), and then have completed the present invention. Additionally, the present inventors have found that the compound of the present invention strongly antagonizes chemokine receptor in the presence of protein.

That is, the present invention relates to:

1. a compound represented by formula (I):

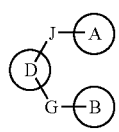

(I)

wherein ring A, ring B and ring D are each independently an optionally substituted cyclic group; J is a bond or a spacer having 1 to 8 atom(s) in its main chain; and G is a bond or a spacer having 1 to 4 atom(s) in its main chain;
a salt thereof, an N-oxide thereof, a solvate thereof or a prodrug thereof, 2. the compound according to above 1, wherein ring D is an optionally substituted monocyclic hetero ring, 3. the compound according to above 2, wherein ring D is an optionally substituted pyrazine ring, 4. the compound according to above 2, wherein ring D is an optionally substituted pyridine ring, 5. the compound according to above 1, wherein ring D is an optionally substituted bicyclic hetero ring, 6. the compound according to above 5, wherein ring D is an optionally substituted cyclic group selected from the group of the following (a) to (y), and wherein, when an arrowhead binds to J, another one binds to G,

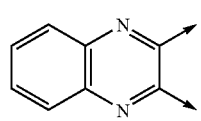
(a)

-continued

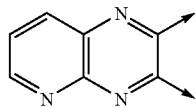
(b)

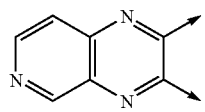
(c)

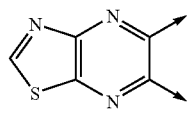
(d)

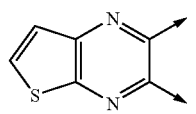
(e)

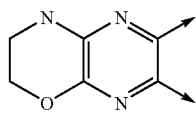
(f)

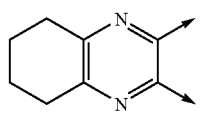
(g)

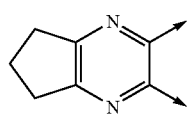
(h)

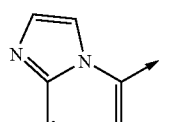
(i)

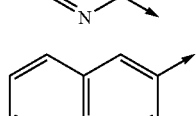
(j)

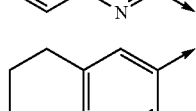
(k)

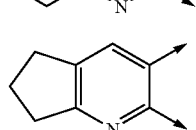
(l)

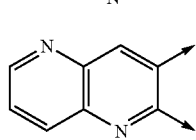
(m)

(n)

-continued

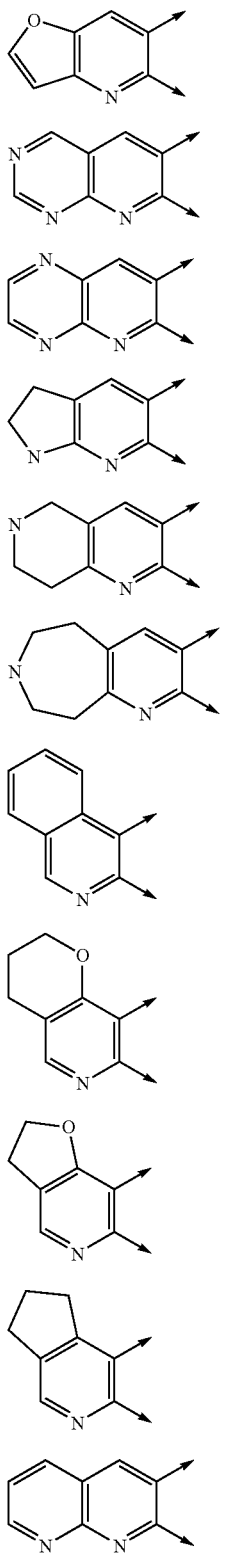

7. the compound according to above 3, 4 or 6, wherein the substituent(s) of ring D is one or two substituent(s) selected from the group consisting of halogen atom and methyl substituted by 1 to 3 of halogen atom(s), 8. the compound according to above 1, wherein J is —O—CH₂—, —NHCH₂—, —NHCO— or —C≡C—, and wherein ring A binds to right side of each group, 9. the compound according to above 1, wherein ring A is a 5- to 10-membered cyclic group, 10. the compound according to above 1, wherein ring A is a 8- to 10-membered bicyclic ring, 11. the compound according to above 9, wherein ring A is an optionally substituted benzene ring, pyridine ring, 3,4-dihydro-2H-1,4-benzoxaxazine ring, 1,2,3,4-tetrahydro-1,8-naphthyridine ring, quinoline ring, 1,2,3,4-tetrahydroisoquinoline ring, pyrazole ring or thiazole ring, 12. the compound according to above 11, wherein the substituent(s) of ring A is one to three substituent(s) selected from the group consisting of chlorine atom, methoxy, 2-(dimethylamino)ethoxy, piperidin-4-ylmethoxy, 1-methylpiperidin-4-ylmethoxy, methyl, t-butoxycarbonyl and phenyl, 13. the compound according to above 1, wherein G is —NHSO₂—, and wherein the nitrogen atom binds to ring D, 14. the compound according to above 1, wherein ring B is an optionally substituted C3-8 monocyclic aromatic carbon ring or an optionally substituted monocyclic aromatic hetero ring having 1 to 4 nitrogen atom(s), 1 or 2 oxygen atom(s) and/or 1 or 2 sulfur atom(s) as a hetero atom(s), 15. the compound according to above 14, wherein ring B is an optionally benzene ring or thiophene ring, 16. the compound according to above 14, wherein the substituent(s) of ring B is one or two substituent(s) selected from the group consisting of halogen atom and methyl substituted by 1 to 3 of halogen atom(s), 17. the compound according to above 1, which is represented by formula (I-1):

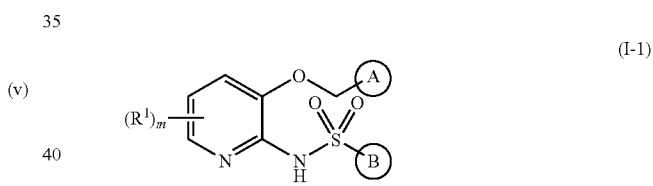

wherein R¹ is the substituent(s) of ring D depicted in above 1, m is 0 or an integer of 1 to 3, and other symbols have the same meanings as above 1, 18. the compound according to above 1, which is represented by formula (I-4):

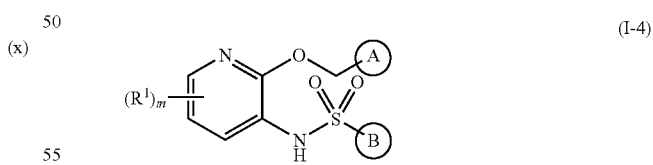

wherein all symbols have the same meanings as above 1 or 17, 19. the compound according to above 1, which is selected from the group consisting of N-[5-bromo-3-({3-[2-(dimethylamino)ethoxy]-4-methoxybenzyl}oxy)pyridin-2-yl]-4-methylbenzenesulfonamide;

3-chloro-N-[3-({4-chloro-3-[(1-methylpiperidin-4-yl)methoxy]benzyl}oxy)-5-methylpyrazin-2-yl]-2-methylbenzenesulfonamide;

2-chloro-N-[3-({4-chloro-3-[(1-methylpiperidin-4-yl)methoxy]benzyl}oxy)-5-methylpyrazin-2-yl]-2-methylbenzenesulfonamide;
3-chloro-2-methyl-N-[5-methyl-3-(quinolin-2-ylmethoxy)pyrazin-2-yl]benzenesulfonamide;
2-chloro-N-[3-({3-[2-(dimethylamino)ethoxy]-4-methoxybenzyl}oxy)quinoxalin-2-yl]benzenesulfonamide;
N-[3-({4-chloro-3-[(1-methylpiperidin-4-yl)methoxy]benzyl}oxy)-5-methylpyrazin-2-yl]-4-methylbenzenesulfonamide;
N-[3-({4-chloro-3-[(1-methylpiperidin-4-yl)methoxy]benzyl}oxy)-5-methylpyrazin-2-yl]-2-(trifluoromethyl)benzenesulfonamide;
3-chloro-2-methyl-N-{5-methyl-3-[(2-methyl-1,2,3,4-tetrahydro-7-isoquinolinyl)methoxy]-2-pyrazinyl}benzenesulfonamide;
N-[5-bromo-3-({4-chloro-3-[(1-methyl-4-piperidinyl)methoxy]benzyl}oxy)-2-pyrazinyl]-4-methylbenzenesulfonamide;
3-chloro-N-{3-[(3,5-dimethyl-1-phenyl-1H-pyrazol-4-yl)methoxy]-5-methyl-2-pyrazinyl}-2-methylbenzenesulfonamide;
3-chloro-2-methyl-N-{5-methyl-3-[(2-phenyl-1,3-thiazol-4-yl)methoxy]-2-pyrazinyl}benzenesulfonamide;
tert-butyl 7-{[[(6-bromo-3-{[(4-methylphenyl)sulfonyl]amino}-2-pyrazinyl)oxy]methyl}-3,4-dihydro-2(1H)-isoquinolinecarboxylate;
N-[5-chloro-3-({3-[2-(dimethylamino)ethoxy]-4-methoxybenzyl}oxy)-2-pyridinyl]-4-methylbenzenesulfonamide and
3-chloro-N-[5-chloro-3-({3-[2-(dimethylamino)ethoxy]-4-methoxybenzyl}oxy)-2-pyridinyl]-2-methylbenzenesulfonamide, 20. a pharmaceutical composition which comprises a compound represented by formula (I):

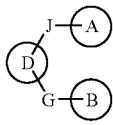
(I)

wherein all symbols have the same meanings as above 1, a salt thereof, an N-oxide thereof, a solvate thereof or a prodrug thereof, 21. the pharmaceutical composition according to above 20, which is a chemokine receptor antagonist, 22. the pharmaceutical composition according to above 21, wherein chemokine receptor is CCR4 and/or CCR5, 23. the pharmaceutical composition according to above 21, which is an agent for prevention and/or treatment of a chemokine receptor-mediated disease, 24. the pharmaceutical composition according to above 23, wherein the chemokine receptor-mediated disease is inflammatory disease, allergic disease, metabolism/endocrine-related disease, cancer and/or infectious disease, 25. the pharmaceutical composition according to above 23, wherein the chemokine receptor-mediated disease is asthma, pulmonary fibrosis, atopic dermatitis, infection of human immunodeficiency virus, acquired immunodeficiency syndrome and/or transplant rejection reaction, 26. the pharmaceutical composition according to above 20, which is a function inhibitor of effector cell, 27. the pharmaceutical composition according to above 26, wherein the function of effector cell is cell migration, increase of vascular permeability, infiltration to tissue, accumulation to tissue, release of humoral factor and/or expression of cell surface antigen, 28. a method for prevention and/or treatment of a chemokine receptor-mediated disease in a mammal, which comprises administering to a mammal an effective amount of a compound represented by formula (I) depicted in above 1, a salt thereof, an N-oxide thereof, a solvate thereof or a prodrug thereof, 29. use of a compound represented by formula (I) depicted in above 1, a salt thereof, an N-oxide thereof, a solvate thereof or a prodrug thereof for the manufacture of an agent for prevention and/or treatment of a chemokine receptor-mediated disease, 30. a medicament, which comprises a compound represented by formula (I) depicted in above 1, a salt thereof, an N-oxide thereof, a solvate thereof or a prodrug thereof in combination with one or two or more of selected from the group consisting of bronchodilator, steroid, nonsteroidal antiinflammatory drug, leukotriene receptor antagonist, phosphodiesterase inhibitor, immunosuppressive drug, antiallergic drug, mediator release inhibitor, antihistamine drug, metabolism accelerator, protease inhibitor, reverse transcriptase inhibitor, integrase inhibitor, fusion inhibitor, interferon, aldose reductase inhibitor, cannabinoid-2 receptor stimulator, adrenocorticotropic hormone, metalloprotease inhibitor, prostaglandin, disease modifying antirheumatic drug, antiinflammatory enzyme drug, cartilage protective drug, T-cell suppressor, TNFα inhibitor, IL-1 inhibitor, IL-6 inhibitor, interferon γ stimulator, NF-κB inhibitor and/or chemokine antagonist, 31. the compound according to above 1, which is represented by formula (I-1):

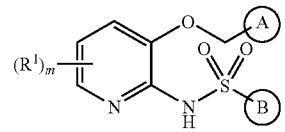
(I-1)

or (I-4):

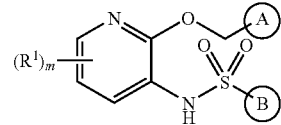
(I-4)

wherein all symbols have the same meanings as above 1 or 17, and wherein the compounds of the following (1) to (18) are excepted:

(1) N-[3-(benzyloxy)pyridin-2-yl]-4-(trifluoromethoxy)benzenesulfonamide,
(2) N-[3-(benzyloxy)pyridin-2-yl]-4-fluorobenzenesulfonamide,
(3) N-{3-[(3,4-dichlorobenzyl)oxy]pyridin-2-yl}-4-propylbenzenesulfonamide,
(4) N-{3-[(3,4-dichlorobenzyl)oxy]pyridin-2-yl}-4-methoxybenzenesulfonamide, (5) 4-bromo-N-{3-[(3,4-dichlorobenzyl)oxy]pyridin-2-yl}benzenesulfonamide,
(6) 4-chloro-N-{3-[(3,4-dichlorobenzyl)oxy]pyridin-2-yl}benzenesulfonamide,
(7) N-{3-[(3,4-dichlorobenzyl)oxy]pyridin-2-yl}-4-methyl-benzenesulfonamide,
(8) N-{3-[(3,5-difluorobenzyl)oxy]pyridin-2-yl}-3,4-difluorobenzenesulfonamide,
(9) N-{3-[(3,5-difluorobenzyl)oxy]pyridin-2-yl}-2-(trifluoromethyl)benzenesulfonamide,
(10) N-{3-[(3,5-difluorobenzyl)oxy]pyridin-2-yl}-4-pentyl-benzenesulfonamide,
(11) N-{3-[(3,5-difluorobenzyl)oxy]pyridin-2-yl}-4-methylbenzenesulfonamide,
(12) N-{3-[(3,5-difluorobenzyl)oxy]pyridin-2-yl}-4-isopropylbenzenesulfonamide,
(13) N-{3-[(3,5-difluorobenzyl)oxy]pyridin-2-yl}-4-propyl-benzenesulfonamide,
(14) 3-chloro-N-{3-[(3,5-difluorobenzyl)oxy]pyridin-2-yl}benzenesulfonamide,
(15) N-{3-[(3,5-difluorobenzyl)oxy]pyridin-2-yl}-4-methoxybenzenesulfonamide,
(16) N-{3-[(3,4-dichlorobenzyl)oxy]pyridin-2-yl}-4-isopropylbenzenesulfonamide,
(17) N-{3-[(3,4-dichlorobenzyl)oxy]pyridin-2-yl}benzenesulfonamide, and
(18) 4-({[3-[(phenylsulfonyl)amino]-5-(trifluoromethyl)pyridin-2-yl]oxy}methyl)benzoic acid], and 32. a process for preparation of the compound represented by formula (I), a salt thereof, an N-oxide thereof, a solvate thereof or a prodrug thereof.

In the specification, the "cyclic group" in the "optionally substituted cyclic group" represented by ring A, ring B and ring D means, for example, a carbocyclic ring and a heterocyclic ring. The carbocyclic ring includes, for example, a "C3-15 mono-, bi- or tri-cyclic carbon ring". The "C3-15 mono-, bi- or tri-cyclic carbon ring" as used herein includes a C3-15 mono-, bi- or tri-cyclic unsaturated carbon ring and partially or fully saturated one, a spiro-fused bicyclic carbon ring and a bridged bicyclic carbon ring. The "C3-15 mono-, bi- or tri-cyclic unsaturated carbon ring and partially or fully saturated one" includes, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene ring, and the like. The "spiro-fused bicyclic carbon ring" includes, for example, spiro[4.4]nonane, spiro[4.5]decane, spiro[5.5]undecane ring, and the like. The "bridged bicyclic carbon ring" includes, for example, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane ring, and the like. Among these, the "C3-15 mono-, bi- or tri-cyclic aromatic carbon ring" includes, for example, benzene, azulene, naphthalene, phenanthrene, anthracene ring, and the like.

The heterocyclic ring includes, for example, a "3- to 15-membered mono-, bi- or tri-cyclic hetero ring having 1 to 4 nitrogen atom(s), 1 or 2 oxygen atom(s) and/or 1 or 2 sulfur atom(s) as a hetero atom(s)". The "3- to 15-membered mono-, bi- or tri-cyclic hetero ring having 1 to 4 nitrogen atom(s), 1 or 2 oxygen atom(s) and/or 1 or 2 sulfur atom(s) as a hetero atom(s)" as used herein includes a 3- to 15-membered mono-, bi- or tri-cyclic unsaturated hetero ring having 1 to 4 nitrogen atom(s), 1 or 2 oxygen atom(s) and/or 1 or 2 sulfur atom(s) as a hetero atom(s) and partially or fully saturated one, a spiro-fused bicyclic hetero ring and a bridged bicyclic hetero ring. The "3- to 15-membered mono-, bi- or tri-cyclic unsaturated hetero ring having 1 to 4 nitrogen atom(s), 1 or 2 oxygen atom(s) and/or 1 or 2 sulfur atom(s) as a hetero atom(s) and partially or fully saturated one" includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole(oxazolidine), dihydroisoxazole, tetrahydroisoxazole(isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzokazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole, pyrido[2,3-b]pyrazine, pyrido[3,4-b]pyrazine, [1,3]thiazolo[4,5-b]pyrazine, thieno[2,3-b]pyrazine, 3,4-dihydro-2H-pyrazino[2,3-b][1,4]oxazine, 6,7-dihydro-5H-cyclopenta[b]pyrazine, imidazo[1,2-a]pyrazine, 6,7-dihydro-5H-cyclopenta[b]pyridine, furo[3,2-b]pyridine, pyrido[2,3-d]pyrimidine, 2,3-dihydro-1H-pyrrolo[2,3-b]pyridine, 5,6,7,8-tetrahydro-1,6-naphthyridine, 6,7,8,9-tetrahydro-5H-pyrido[2,3-d]azepine, 3,4-dihydro-2H-pyrano[3,2-c]pyridine, 2,3-dihydrofuro[3,2-c]pyridine ring, and the like. The "spiro-fused bicyclic hetero ring" includes, for example, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane ring, and the like. The "bridged bicyclic hetero ring" includes, for example, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane ring, and the like. Among these, the "3- to 15-membered mono-, bi- or tri-cyclic aromatic hetero ring having 1 to 4 nitrogen atom(s), 1 or 2 oxygen atom(s) and/or 1 or 2 sulfur atom(s) as a hetero atom(s)" includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine ring, and the like.

The "substituent" in the "optionally substituted cyclic group" represented by ring A, ring B and ring D is not particularly limited, so long as it is a substituent. The "substituent" includes, for example, the substituents as exemplified below.

The "substituent" in the above-described "optionally substituted cyclic group" includes, for example, (1) a substituent selected from the following Group I, (2) a substituent selected from the following Group II, (3) an optionally substituted 3- to 15-membered cyclic group, (4) an optionally substituted carbamoyl, (5) an optionally substituted aliphatic hydrocarbon group, and the like. One to ten, preferably one to five, more preferably one to three substituent(s) among these optional substituents may be located at any position where substitution is possible.

<Group I>
(1) halogen atom (chlorine, bromine, fluorine, and iodine), (2) cyano, (3) nitro, (4) trifluoromethyl, (5) trifluoromethoxy, (6) oxo and (7) thioxo.

<Group II>
(1) —$OR^{a1}$, (2) —$NR^{a1}R^{a2}$, (3) —$NR^{a1}COR^{a2}$, (4) —$COOR^{a1}$, (5) —$SR^{a1}$, (6) —$SOR^{a1}$, (7) —$SO_2R^{a1}$ and (8) —$COR^{a1}$, wherein $R^{a1}$ and $R^{a2}$ are each independently (a) hydrogen atom, (b) an optionally substituted aliphatic hydrocarbon group, or (c) an optionally substituted 3- to 15-membered cyclic group. If plural substituents are selected from this group, plural $R^{a1}$ or plural $R^{a2}$ are the same or different.

The "aliphatic hydrocarbon group" in the "optionally substituted aliphatic hydrocarbon group" as used herein represented by $R^{a1}$ and $R^{a2}$ includes, for example, a "straight or branched aliphatic hydrocarbon group", and the like. The "straight or branched aliphatic hydrocarbon group" includes, for example, a "C1-8 aliphatic hydrocarbon group", and the like. The "C1-8 aliphatic hydrocarbon group" includes, for example, C1-8 alkyl, C2-8 alkenyl, C2-8 alkynyl, and the like.

As C1-8 alkyl, for example, methyl, ethyl, propyl, isopropyl, butyl, sec-butyl, tert-butyl, pentyl, hexyl, heptyl, octyl, and isomers thereof can be included.

As C2-8 alkenyl, for example, vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl, and isomers thereof can be included.

As C2-8 alkynyl, for example, ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl, and isomers thereof can be included.

The "substituent" in the "optionally substituted aliphatic hydrocarbon group" represented by $R^{a1}$ and $R^{a2}$ includes, for example, (1) a substituent selected from the above-described Group I, (2) a substituent selected from the following Group III, (3) an optionally substituted 3- to 15-membered cyclic group, and the like. One to eight, preferably one to five substituent(s) among these optional substituents may be located at any position where substitution is possible.

<Group III>
(1) —$OR^{b1}$ and (2) —$NR^{b1}R^{b2}$, wherein $R^{b1}$ and $R^{b2}$ are each independently (a) hydrogen atom, (b) hydroxy, (c) amino, (d) C1-8 alkyl (which has the same meaning as described above), (e) C1-8 alkoxy (e.g., methoxy, ethoxy, propoxy, butoxy, pentyloxy, hexyloxy, heptyloxy, octyloxy, and isomers thereof, etc.), (f) monosubstituted or disubstituted C1-8 alkylamino (e.g., methylamino, ethylamino, propylamino, dimethylamino, diethylamino, etc.), (g) C1-8 alkyl substituted by "monosubstituted or disubstituted C1-8 alkylamino" (C1-8 alkyl has the same meaning as described above), and (h) C1-8 alkoxy substituted by "monosubstituted or disubstituted C1-8 alkylamino" (C1-8 alkoxy has the same meaning as described above). If plural substituents are selected from this group, plural $R^{b1}$ or plural $R^{b2}$ are the same or different.

In the specification, the "3- to 15-membered cyclic group" in the "optionally substituted 3- to 15-membered cyclic group" includes, for example, the above-described "C3-15 mono-, bi- or tri-cyclic carbon ring", "3- to 15-membered mono-, bi- or tri-cyclic hetero ring having 1 to 4 nitrogen atom(s), 1 or 2 oxygen atom(s) and/or 1 or 2 sulfur atom(s) as hetero atom(s)", and the like.

The "substituent" in the "optionally substituted 3- to 15-membered cyclic group" includes, for example, (1) a substituent selected from the above-described Group I, (2) an optionally substituted aliphatic hydrocarbon group, (3) a substituent selected from the following Group IV, (4) an optionally substituted 3- to 8-membered cyclic group, and the like. One to ten, preferably one to five, more preferably one to three substituent(s) among these optional substituents may be located at any position where substitution is possible. The "aliphatic hydrocarbon group" in the "optionally substituted aliphatic hydrocarbon group" as used herein includes, for example, the above-described "C1-8 aliphatic hydrocarbon group", and the like. The "substituent" in the "optionally substituted aliphatic hydrocarbon group" includes, for example, (1) a substituent selected from the above-described Group I, (2) a substituent selected from the following Group IV, (3) an optionally substituted 3- to 8-membered cyclic group, and the like. One to eight, preferably one to five substituent(s) among these optional substituents may be located at any position where substitution is possible.

<Group IV>

(1) —$OR^{c1}$, (2) —$SR^{c1}$, (3) —$NR^{c1}R^{c2}$, (4) —$COR^{c1}$, (5) —$COOR^{c1}$, (6) —$NR^{c1}COR^{c2}$, (7) —$CONR^{c1}R^{c2}$, (8) —$SOR^{c1}$ and (9) —$SO_2R^{c1}$, wherein $R^{c1}$ and $R^{c2}$ are each independently (a) hydrogen atom, (b) an optionally substituted 3- to 8-membered cyclic group, or (c) an aliphatic hydrocarbon group which may be substituted by an optionally substituted 3- to 8-membered cyclic group. If plural substituents are selected from this group, plural $R^{c1}$ or plural $R^{c2}$ are the same or different.

The "aliphatic hydrocarbon group" in the "aliphatic hydrocarbon group which may be substituted by an optionally substituted 3- to 8-membered cyclic group" as used herein represented by $R^{c1}$ or $R^{c2}$ includes, for example, the above-described "C1-8 aliphatic hydrocarbon group", and the like.

In the specification, the "3- to 8-membered cyclic group" in the "optionally substituted 3- to 8-membered cyclic group" includes, for example, a "C3-8 monocyclic carbon ring", a "3- to 8-membered monocyclic hetero ring", and the like.

The "C3-8 monocyclic carbon ring" as used herein includes a C3-8 monocyclic unsaturated carbon ring, or partially or fully saturated one. The "C3-8 monocyclic unsaturated carbon ring, or partially or fully saturated one" includes, for example, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene ring, and the like. Among these, the "C3-8 monocyclic aromatic carbon ring" includes, for example, benzene ring, and the like.

Also, the "3- to 8-membered monocyclic hetero ring" includes, for example, "3- to 8-membered monocyclic hetero ring having 1 to 4 nitrogen atom(s), 1 or 2 oxygen atom(s) and/or 1 or 2 sulfur atom(s) as hetero atom(s)", and the like. The "3- to 8-membered monocyclic hetero ring having 1 to 4 nitrogen atom(s), 1 or 2 oxygen atom(s) and/or 1 or 2 sulfur atom(s) as hetero atom(s)" as used herein includes a 3- to 8-membered monocyclic unsaturated hetero ring having 1 to 4 nitrogen atom(s), 1 or 2 oxygen atom(s) and/or 1 or 2 sulfur atom(s) as hetero atom(s) and partially or fully saturated one. The "3- to 8-membered monocyclic unsaturated hetero ring having 1 to 4 nitrogen atom(s), 1 or 2 oxygen atom(s) and/or 1 or 2 sulfur atom(s) as hetero atom(s) and partially or fully saturated one" includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole(oxazolidine), dihydroisoxazole, tetrahydroisoxazole(isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane ring, and the like. Among these, the "3- to 8-membered monocyclic aromatic hetero ring" includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole ring, and the like.

The "substituent" in the "optionally substituted 3- to 8-membered cyclic group" includes, for example, (1) a substituent selected from the above-described Group I, (2) C1-8 alkyl (which has the same meaning as described above), (3) C2-8 alkenyl (which has the same meaning as described above), (4) C2-8 alkynyl (which has the same meaning as described above), and (5) hydroxy, and the like. One to eight, preferably one to five substituent(s) among these optional substituents may be located at any position where substitution is possible.

The "optionally substituted carbamoyl" as the "substituent" in the "optionally substituted cyclic group" represented by ring A, ring B and ring D includes, for example, N-monosubstituted carbamoyl and N,N-disubstituted carbamoyl, in addition to unsubstituted carbamoyl. The "N-monosubstituted carbamoyl" means carbamoyl having one substituent on the nitrogen atom, and the "N,N-disubstituted carbamoyl" means carbamoyl having two substituents on the nitrogen atom. The substituent of carbamoyl includes, for example, (1) the above-described "3- to 15-membered cyclic group", (2) an optionally substituted aliphatic hydrocarbon group, (3) an optionally protected hydroxy, and the like. One or two substituent(s) among these optional substituents may be located at any position where substitution is possible. The substituents of carbamoyl in the "N,N-disubstituted carbamoyl" may be taken together with nitrogen atom which they are bound to represent (4) an optionally substituted 3- to 8-membered nitrogen atom-containing hetero ring.

The "optionally protected hydroxy" as used herein includes, for example, hydroxy and protected hydroxy. The "protective group" in the "protected hydroxy" includes, for example, (1) an optionally substituted C1-8 alkyl (C1-8 alkyl has the same meaning as described above), (2) an optionally substituted C2-8 alkenyl (C2-8 alkenyl has the same meaning as described above), (3) an optionally substituted C2-8 alkynyl (C2-8 alkynyl has the same meaning as described above), (4) the above-described "optionally substituted 3- to 15-membered cyclic group", and the like. The "substituent" in the "optionally substituted C1-8 alkyl", the "optionally substituted C2-8 alkenyl" and the "optionally substituted C2-8 alkynyl" as used herein includes, for example, (1) the above-described "optionally substituted 3- to 15-membered cyclic group", (2) a substituent selected from the above-described Group I, and the like. One to eight, preferably one to five substituent(s) among these optional substituents may be located at any position where substitution is possible.

The "aliphatic hydrocarbon group" in the "optionally substituted aliphatic hydrocarbon group" as the substituent of the "N-monosubstituted carbamoyl" and the "N,N-disubstituted carbamoyl" includes, for example, the above-described "C1-8 aliphatic hydrocarbon group", and the like. The "substituent" in the "optionally substituted aliphatic hydrocarbon group" as used herein includes, for example, (1) a substituent selected from the above-described Group I, (2) the above-described "optionally substituted 3- to 15-membered cyclic group", (3) a substituent selected from the above-described Group II, and the like. One to eight, preferably one to five substituent(s) among these optional substituents may be located at any position where substitution is possible.

In the specification, the "3- to 8-membered nitrogen atom-containing hetero ring" in the "optionally substituted 3- to 8-membered nitrogen atom-containing hetero ring" includes, for example, a "3- to 8-membered monocyclic hetero ring having at least one nitrogen atom as a hetero atom(s) and 0 to 3 nitrogen atom(s), 0 to 1 oxygen atom and/or 0 to 1 sulfur atom as an other hetero atom(s)", and the like. The "3- to 8-membered monocyclic hetero ring having at least one nitrogen atom as a hetero atom(s) and 0 to 3 nitrogen atom(s), 0 to 1 oxygen atom and/or 0 to 1 sulfur atom as an other hetero atom(s)" as used herein includes, for example, a 3- to 8-membered monocyclic unsaturated hetero ring having at least one nitrogen atom as a hetero atom(s) and 0 to 3 nitrogen atoms, 0 to 1 oxygen atom and/or 0 to 1 sulfur atom as an other hetero atom(s), or partially or completely saturated one. The "3- to 8-membered monocyclic unsaturated hetero ring having at least one nitrogen atom as a hetero atom(s) and 0 to 3 nitrogen atoms, 0 to 1 oxygen atom and/or 0 to 1 sulfur atom as an other hetero atom(s), or partially or completely saturated one" includes, for example, pyrrole, imidazole, triazole, tetrazole, pyrazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole(thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine ring, and the like. Among these, the "3- to 8-membered monocyclic aromatic hetero ring having at least one nitrogen atom as a hetero atom(s) and 0 to 3 nitrogen atoms, 0 to 1 oxygen atom and/or 0 to 1 sulfur atom as an other hetero atom(s)" includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole ring, and the like.

The "substituent" in the "optionally substituted 3- to 8-membered nitrogen atom-containing hetero ring" includes, for example, (1) a substituent selected from the above-described Group I, (2) hydroxy, (3) C1-8 alkyl which may be substituted by 1 to 8 hydroxy (C1-8 alkyl has the same meaning as described above), and the like. One to eight, preferably one to five substituent(s) among these optional substituents may be located at any position where substitution is possible.

The "aliphatic hydrocarbon group" in the "optionally substituted aliphatic hydrocarbon group" as the "substituent" in the "optionally substituted cyclic group" represented by ring A, ring B and ring D includes, for example, the above-described "C1-8 aliphatic hydrocarbon group", and the like. The "substituent" in the "optionally substituted aliphatic hydrocarbon group" as used herein includes, for example, (1) a substituent selected from the above-described Group I, (2) the above-described "optionally substituted 3- to 15-membered cyclic group", (3) the above-described "optionally substituted carbamoyl", (4) a substituent selected from the above-described Group II, and the like. One to eight, preferably one to five substituent(s) among these optional substituents may be located at any position where substitution is possible.

The "spacer having 1 to 4 atom(s) in its main chain" represented by G means a space in which 1 to 4 atom(s) exist uninterruptedly in its main chain. The "number of atom in its main chain" is counted such that the number of atom in its main chain are minimized. For example, the number of atom in 1,2-cyclopentylene is counted as 2, and in 1,3-cyclopentylene is counted as 3.

The "spacer having 1 to 4 atom(s) in its main chain" includes, for example, a bivalent group having 1 to 4 uninterrupted atom(s) in its main chain and consisting of 1 to 4 groups selected from —O—, —S—, —CO—, —SO—, —SO$_2$—, an optionally substituted nitrogen atom, an optionally substituted bivalent C1-4 aliphatic hydrocarbon group, an optionally substituted bivalent C3-8 monocyclic carbon ring, and an optionally substituted bivalent 3- to 8-membered monocyclic hetero ring, and the like. The "optionally substituted nitrogen atom" as used herein represents —NH—, and further a group in which the hydrogen atom in the "—NH—" is substituted with (1) an optionally substituted C1-8 alkyl (C1-8 alkyl has the same meaning as described above), (2) an optionally substituted C2-8 alkenyl (C2-8 alkenyl has the same meaning as described above), (3) an optionally substituted C2-8 alkynyl (C2-8 alkynyl has the same meaning as described above), (4) the above-described "optionally substituted 3- to 8-membered cyclic group", or the like. The "substituent" in the "optionally substituted C1-8 alkyl", the "optionally substituted C2-8 alkenyl" and the "optionally substituted C2-8 alkynyl" as the "substituent" in the "optionally substituted nitrogen atom" as used herein includes, for example, (a) hydroxy, (b) the above-described "optionally substituted 3- to 8-membered cyclic group", and the like. One to eight, preferably one to five substituent(s) among these optional substituents may be located at any position where substitution is possible.

The "bivalent C1-4 aliphatic hydrocarbon group" in the "optionally substituted bivalent C1-4 aliphatic hydrocarbon group" includes, for example, C1-4 alkylene (e.g., —CH$_2$—, —(CH$_2$)$_2$—, —(CH$_2$)$_3$—, —(CH$_2$)$_4$—, etc.), C2-4 alkenylene (e.g., —CH=CH—, —CH$_2$—CH=CH—, —CH=CH—CH$_2$—, —(CH$_2$)$_2$—CH=CH—, —CH=CH—(CH$_2$)$_2$—, —CH$_2$—CH=CH—CH$_2$—, etc.), C2-4 alkynylene (e.g., —C≡C—, —CH$_2$—C≡C—, —C≡C—CH$_2$—, —(CH$_2$)$_2$—C≡C—, —C≡C—(CH$_2$)$_2$—, —CH$_2$—C≡C—CH$_2$—, etc.), and the like.

The "substituent" in the "optionally substituted bivalent C1-4 aliphatic hydrocarbon group" includes, for example, (1) C1-8 alkyl (which has the same meaning as described above), (2) C1-8 alkoxy (which has the same meaning as described above), (3) halogen atom (which has the same meaning as described above), (4) hydroxy, (5) oxo, (6) thioxo, (7) amino, (8) =N—OR″, wherein R″ represents hydrogen atom or has the same meaning as the "substituent" in the "optionally substituted nitrogen atom", and the like. One to five, preferably one to two substituent(s) among these optional substituents may be located at any position where substitution is possible.

In addition, the "bivalent C3-8 monocyclic carbon ring" in the "optionally substituted bivalent C3-8 monocyclic carbon ring" includes, for example, a bivalent group made by removing any two hydrogen atoms from the rings exemplified as the above-described "C3-8 monocyclic carbon ring", and the like. The "substituent" in the "optionally substituted bivalent C3-8 monocyclic carbon ring" includes, for example, a substituent which was exemplified as the "substituent" in the above-described "optionally substituted 3- to 8-membered cyclic group", and the like. One to eight, preferably one to five substituent(s) among these optional substituents may be located at any position where substitution is possible.

The "bivalent 3- to 8-membered monocyclic hetero ring" in the "optionally substituted bivalent 3- to 8-membered monocyclic hetero ring" includes, for example, a bivalent group made by removing any two hydrogen atoms from the rings exemplified as the above-described "3- to 8-membered monocyclic hetero ring", and the like. The "substituent" in the "optionally substituted bivalent 3- to 8-membered monocyclic hetero ring" includes, for example, a substituents which was exemplified as the substituent in the above-described "optionally substituted 3- to 8-membered cyclic group", and the like. One to eight, preferably one to five substituent(s) among these optional substituents may be located at any position where substitution is possible.

The "spacer having 1 to 4 atom(s) in its main chain and containing at least one nitrogen atom" represents a bivalent group containing at least one "optionally substituted nitrogen atom", which is above-described, among the groups of the "spacer having 1 to 4 atom(s) in its main chain". When the "optionally substituted nitrogen atom" is contained in two or more, the substituents of each nitrogen atom are the same or different. The "spacer having 1 to 4 atoms in its main chain and containing at least one nitrogen atom" preferably includes, for example, —NR$^{T1}$—, —NR$^{T1}$—SO$_2$—, —NR$^{T1}$—CO—, NR$^{T1}$—CO—NR$^{T2}$—, —NR$^{T1}$—SO$_2$—NR$^{T2}$—, —NR$^{T1}$—COO—, —NR$^{T1}$—O—, —NR$^{T1}$—NR$^{T2}$—, —NR$^{T1}$—W—, —SO$_2$—NR$^{T1}$—, —CO—NR$^{T1}$—, —OCO—NR$^{T1}$—, —O—NR$^{T1}$—, —W—NR$^{T1}$—, wherein W represents the "optionally substituted bivalent C1-3 aliphatic hydrocarbon group", and R$^{T1}$ and R$^{T2}$ each independently represents hydrogen or has the same meaning as the substituents in the above-described "optionally substituted nitrogen atom", and the like. The "bivalent C1-3 aliphatic hydrocarbon group" in the "optionally substituted bivalent C1-3 aliphatic hydrocarbon group" represented by W as used herein represents C1-3 alkylene (e.g., —CH$_2$—, —(CH$_2$)$_2$—, —(CH$_2$)$_3$—, etc.), C2-3 alkenylene (e.g., —CH=CH—, —CH$_2$—CH=CH—, —CH=CH—CH$_2$—, etc.) and C2-3 alkynylene (e.g., —C≡C—, —CH$_2$—C≡C—, —C≡C—CH$_2$—, etc.), and the like. Furthermore, the "substituent" in the "optionally substituted bivalent C1-3 aliphatic hydrocarbon group" has the same meaning as the substituent in the above-described "optionally substituted bivalent C1-4 aliphatic hydrocarbon group".

The "spacer having 1 to 8 atom(s) in its main chain" represented by J means a space in which 1 to 8 atom(s) exist uninterruptedly in its main chain. The "number of atom in its main chain" is counted such that the number of atom in its main chain are minimized as in the above-described "spacer having 1 to 4 atom(s) in its main chain". For example, the number of atom in 1,4-phenylene is counted as 4, and in 1,3-phenylene is counted as 3.

The "spacer having 1 to 8 atom(s) in its main chain" includes, for example, a bivalent group having 1 to 8 uninterrupted atoms in its main chain and consisting of 1 to 8 groups selected from —O—, —S—, —CO—, —SO—, —SO$_2$—, the above-described "optionally substituted nitrogen atom", an optionally substituted bivalent C1-8 aliphatic hydrocarbon group, the above-described "optionally substituted bivalent C3-8 monocyclic carbon ring", and the above-described "optionally substituted 3- to 8-membered monocyclic hetero ring", and the like.

The "bivalent C1-8 aliphatic hydrocarbon group" in the "optionally substituted bivalent C1-8 aliphatic hydrocarbon group" as used herein includes, for example, C1-8 alkylene (e.g., methylene, ethylene, trimethylene, tetramethylene, pentamethylene, hexamethylene, heptamethylene, octamethylene, etc.), C2-8 alkenylene (e.g., ethenylene, propenylene, butenylene, butadienylene, pentenylene, pentadienylene, hexenylene, hexadienylene, heptenylene, heptadienylene, octenylene, octadienylene, etc.), C2-8 alkynylene (e.g., ethynylene, propynylene, butynylene, butadiynylene, pentynylene, pentadiynylene, hexynylene, hexadiynylene, heptynylene, heptadiynylene, octynylene, octadiynylene, etc.), and the like. The "substituent" in the "optionally substituted bivalent C1-8 aliphatic hydrocarbon group" includes, for example, those exemplified as the "substituent" in the above-described "optionally substituted bivalent C1-4 aliphatic hydrocarbon group", and the like. One to ten, preferably one to five, more preferably one to three substituent(s) among these optional substituents may be located at any position where substitution is possible.

In the present specification, the effector cells include all T cells except naive T cells. The naive T cells mean T cells which have never received antigen stimulation. The effector cells include, for example, RA negative and/or RO positive T cells. The "RA negative and/or RO positive T cells" include, for example, Th1 cells, Th2 cells, cytotoxic T-lymphocytes (CTL), central memory T cells (TCM), effector memory T cell (TEM), and the like. RA and RO mean cell surface antigens. The term "negative" means that surface antigen can not be detected, and the term "positive" means that surface antigen can be detected. A method used to detect the surface antigen includes all the methods of detecting a surface antigen known so far. For example, it includes techniques used for the skilled persons in the art to detect proteins (e.g., flow cytometry (FACS), immunostaining, Western blot, fluorescent antibody method, etc.) or equivalent techniques thereof TCM and TEM are those defined in literatures (*Nature*. Oct. 14, 1999; 401 (6754): 708-12.). In the present invention, preferable effector cells are effector cells which express CCR4 and/OR CCR5, namely CCR4 and/or CCR5-positive effector cells.

In the specification, a function of effector cell include all functions of effector cell related to CCR4. The functions of effector cell related to CCR4 include, for example, cell migration, increase of vascular permeability, infiltration to tissue, accumulation to tissue, release of humoral factor expression of cell surface antigen, and the like.

In the specification, TNFα regulating activity mean activity of regulating TNFα amount in the living body, preferably reducing TNFα amount in the tissue or the blood, more specifically, reducing TNFα amount in the tissue or the blood in various diseases known to increase TNFα amount in the tissue or the blood.

Unless otherwise specified, the present invention includes all isomers. For example, alkyl, alkenyl, alkynyl, alkoxy, alkylthio, alkylene, alkenylene, alkynylene, etc. include straight or branched ones. In addition, the present invention also include isomers on double bond, ring, fused ring (E-, Z-, cis-, trans-isomer), isomers generated from asymmetric carbon atoms (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at any ratios and racemic mixtures.

Salts:

The compound of the present invention represented by formula (I) may be converted into non-toxic and pharmacologically acceptable salts by a known method. Salts of the compound represented by formula (I) include all non-toxic salts and pharmacologically acceptable salts. The pharmacologically acceptable salts are preferably non-toxic and water-soluble salts. Suitable salts of the compound represented by formula (I) include, for example, salts of alkali metals (potassium, sodium, lithium, etc.), salts of alkaline earth metals (calcium, magnesium, etc.), ammonium salts (tetramethylammonium salts, tetrabutylammonium salts, etc.), salts with organic amines (triethylamine, methylamine, dimethylamine, cyclopentylamine, benzylamine, phenethylamine, piperidine, monoethanolamine, diethanolamine, tris(hydroxymethyl)methylamine, lysine, arginine or N-methyl-D-glucamine, etc.) and acid addition salts [salts of inorganic acids (hydrochloride, hydrobromide, hydroiodide, sulfate, phosphate, nitrate, etc.), salts of organic acids (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.)], and the like.

Furthermore, the salts of the compound of the present invention also include quaternary ammonium salts. The quaternary ammonium salts mean compounds where a nitrogen atom of the compound represented by formula (I) is quaternized by $R^0$ ($R^0$ represents C1-8 alkyl or C1-8 alkyl substituted by phenyl).

Furthermore, the present invention also includes N-oxides of the compound represented by formula (I). The N-oxides mean compounds where nitrogen atom of the compound represented by formula (I) is oxidized. The compound of the present invention can be converted to N-oxide by any known method.

Moreover, the present invention also includes solvates of the above-described non-toxic and pharmacologically acceptable salts of the compound represented by formula (I) and solvates of the N-oxide of the compound represented by formula (I), in addition to solvates of the compound represented by formula (I). The solvates are preferably non-toxic and water-soluble one. The appropriate solvates include, for example, solvates of water, alcohol solvents (ethanol, etc.), and the like.

The prodrug of the compound represented by formula (I) means a compound which is converted to the compound represented by formula (I) by reaction with an enzyme, a gastric acid, or the like, in the living body. Examples of the prodrug of the compound represented by formula (I) include a compound wherein amino of the compound represented by formula (I) is substituted by acyl, alkyl, phosphoric acid, or the like (e.g., a compound wherein amino of the compound represented by formula (I) is substituted by eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethy, tert-butyl, etc.); a compound wherein hydroxy of the compound represented by formula (I) is substituted with acyl, alkyl, phosphoryl, boryl, or the like (e.g., a compound wherein hydroxy of the compound represented by formula (I) is substituted by acetyl, palmitoyl, propanoyl, pivaloyl, succinyl, fumaryl, alanyl, dimethylaminomethylcarbonyl, etc.); a compound wherein carboxy of the compound represented by formula (I) is esterified or amidated (e.g., a compound wherein carboxy of the compound represented by formula (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester, methyl amide, etc.), and the like. These compounds may be prepared by per se known method. In addition, the prodrug of the compound represented by formula (I) may hydrate or non-hydrate. In addition, the prodrug of the compound represented by formula (I) may be a compound which is converted into the compound represented by formula (I) under the physiological conditions as described in *Development of Medicine*, Vol. 7 "Molecular Design", pages 163-198 published in 1990 by Hirokawa Publishing Co. In addition, the compound represented by formula (I) may be labeled with an isotope (e.g., $^3H$, $^{14}C$, $^{35}S$, $^{125}I$, etc.) and the like.

The compound of the present invention represented by formula (I) excels in solubility and absorbability. Also, the compound of the present invention inhibits drug-metabolizing enzyme weakly. These properties are most important physical, chemical, or pharmaceutical properties which are requested at the developmental stage of medicinal drugs, so the compound of the present invention has the properties enough to be good medicinal drugs (see *The Merck Manual of Diagnosis and Therapy* ($17^{th}$ Ed), Merck & Co.).

In formula (I) of the present invention, any of each definition represented by ring A, ring B, ring D, J, and G is preferred. In the following, preferred groups, and preferred rings will be listed. The symbols used herein have the same meanings as described above.

The "cyclic group" in the "optionally substituted cyclic group" represented by ring A is preferably, for example, a carbocyclic ring, a heterocyclic ring, and the like; more preferably, for example, the "5- to 10-membered cyclic group" (e.g., 5- to 10-membered cyclic group of the above-described carbocyclic ring or the heterocyclic ring), and the like; furthermore preferably, the "5- to 7-membered monocyclic ring or 8- to 10-membered bicyclic ring" (e.g., 5- to 7-membered monocyclic ring or 8- to 10-membered bicyclic ring of the above-described carbocyclic ring or the heterocyclic ring), and the like. Most preferably, for example, benzene, naphthalene, pyridine, pyrazole, dioxaindan, benzodioxane, cyclopropane, cyclopentane, cyclohexane, furan, thiophene, tetrahydrofuran, piperidine, morpholine, pyridine-1-oxide, 1-methylpyridinium, dihydrobenzoxazine or tetrahydronaphthyridine, quinoline, tetrahydroisoquinoline, thiazole ring, and the like can be cited. As specifically preferable one, for example, benzene, pyridine, dihydrobenzoxazine, tetrahydronaphthyridine, quinoline, pyrazole, tetrahydroisoquinoline, thiazole ring, and the like can be cited.

The "substituent" in the "optionally substituted cyclic group" represented by ring A is preferably, for example, halogen, trifluoromethyl, an optionally substituted aliphatic hydrocarbon group, —OR$^{a1}$, —NR$^{a1}$R$^{a2}$, —COOR$^{a1}$, an optionally substituted 3- to 15-membered cyclic group, and the like; more preferably, for example, (a) halogen, (b) an optionally substituted C1-8 alkyl, (c) hydroxy, (d) amino, (e) —O—(C1-8 alkyl) which may be substituted by —NR$^{b1}$R$^{b2}$ or an optionally substituted 3- to 15-membered cyclic group, (f) an optionally substituted 3- to 15-membered cyclic group, (g) —COOR$^{a1}$ and the like; most preferably, for example, (a) halogen, (b) an optionally substituted C1-4 alkyl, (c) hydroxy, (d) amino, (e) —O—(C1-4 alkyl) which may be substituted by —NR$^{b1}$R$^{b2}$ or an optionally substituted 5- to 7-membered heterocyclic ring (e.g., 5- to 7-membered heterocyclic ring of the above-described 3- to 15-membered heterocyclic ring), (f) optionally substituted C5-7 carbocyclic ring (e.g., 5- to 7-membered carbocyclic ring of the above-described 3- to 15-membered carbocyclic ring), (g) —COO(C1-4 alkyl) and the like. As specifically preferable one, for example, fluorine, chlorine, methyl, hydroxy, methoxy, 2-dimethylaminoethyloxy, piperidin-4-ylmethoxy, 1-methylpiperidin-4-ylmethoxy, t-butoxycarbonyl, phenyl, amino and the like can be cited. The number of substituents of ring A is preferably 0 to 5, more preferably 0 to 3.

The "cyclic group" in the "optionally substituted cyclic group" represented by ring B is preferably, for example, a carbocyclic ring, a heterocyclic ring, and the like; more preferably, for example, a "C3-15 mono-, bi- or tri-cyclic carbon ring", a "3- to 15-membered mono-, bi- or tri-cyclic hetero ring having 1 to 4 nitrogen atom(s), 1 or 2 oxygen atom(s) and/or 1 or 2 sulfur atom(s) as a hetero atom(s)", and the like. Specifically, for example, benzene, pyridine, thiophene, naphthalene, pyrrole, pyrazole, isoxazole, thiazole, benzothiadiazole, benzothiophene, imidazole, benzofurazan, furan, benzopyran ring, and the like can be cited. Among the "C3-15 mono-, bi- or tri-cyclic carbon ring", or the "3- to 15-membered mono-, bi- or tri-cyclic hetero ring having 1 to 4 nitrogen atom(s), 1 or 2 oxygen atom(s) and/or 1 or 2 sulfur atom(s) as a hetero atom(s)", for example, a C3-8 monocyclic carbon ring, a 3- to 8-membered monocyclic hetero ring having 1 to 4 nitrogen atom(s), 1 or 2 oxygen atom(s) and/or 1 or 2 sulfur atom(s) as a hetero atom(s), and the like can be cited preferably. Among them, a "C3-8 monocyclic aromatic carbon ring", a "3- to 8-membered monocyclic aromatic hetero ring having 1 to 4 nitrogen atom(s), 1 or 2 oxygen atom(s) and/or 1 or 2 sulfur atom(s) as a hetero atom(s)" can be cited more preferably. Specifically, for example, benzene, pyridine, thiophene, furan, pyrrole, pyrazole, isoxazole, thiazole ring, and the like can be cited preferably. For example, benzene or thiophen ring and the like can be cited most preferably.

The "substituent" in the "optionally substituted cyclic group" represented by ring B is preferably, for example, a substituent selected from the above-described Group I, an optionally substituted aliphatic hydrocarbon group, a substituent selected from the above-described Group II, an optionally substituted carbamoyl, and the like; more preferably, for example, an optionally substituted aliphatic hydrocarbon group, halogen, nitro, cyano, methyl which may be substituted by 1 to 3 of halogen atom(s) (e.g., methyl, fluoromethyl, difluoromethyl, trifluoromethyl, chloromethyl, dichloromethyl, trichloromethyl, bromomethyl, etc.), trifluoromethoxy, —OR$^{a1}$, —NR$^{a1}$R$^{a2}$, —SO$_2$R$^{a1}$, —SR$^{a1}$, —COOR$^{a1}$, —COR$^{a1}$, and the like; especially preferably, for example, C1-8 alkyl, halogen, nitro, trifluoromethyl, and the like and most preferably, for example, methyl, fluorine, chlorine, bromine, nitro, trifluoromethyl, or the like. For example, methyl, fluorine, chlorine, trifluoromethyl, and the like can be cited most preferably. The number of substituents of ring B is preferably 0 to 5, more preferably 0 to 2.

The "cyclic group" in the "optionally substituted cyclic group" represented by ring D is preferably, for example, a carbocyclic ring, a heterocyclic ring, and the like; more preferably, for example, a "3- to 15-membered mono-, bi- or tri-cyclic hetero ring having 1 to 4 nitrogen atom(s), 1 or 2 oxygen atom(s) and/or 1 or 2 sulfur atom(s) as a hetero atom(s)", and the like; and especially preferably, for example, a "3- to 10-membered mono- or bi-cyclic hetero ring having 1 to 4 nitrogen atom(s), 1 or 2 oxygen atom(s) and/or 1 or 2 sulfur atom(s) as a hetero atom(s)", and the like. The "3- to 10-membered mono- or bi-cyclic hetero ring having 1 to 4 nitrogen atom(s), 1 or 2 oxygen atom(s) and/or 1 or 2 sulfur atom(s) as a hetero atom(s)" is preferably, for example, pyrazine, pyridine, and the rings selected from the group consisting of the following (a) to (y), and the like.

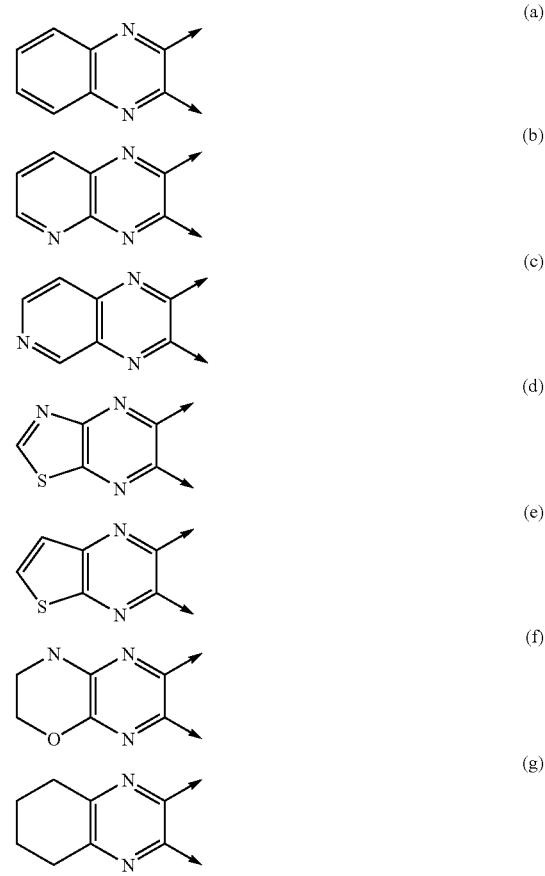

-continued (h) 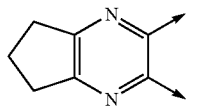

(i) 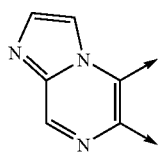

(j) 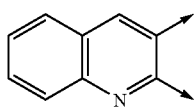

(k) 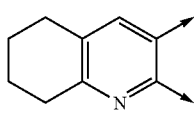

(l) 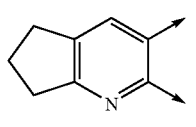

(m) 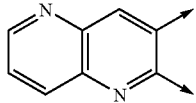

(n) 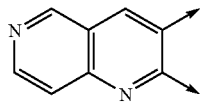

(o) 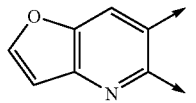

(p) 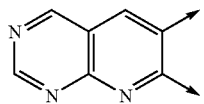

(q) 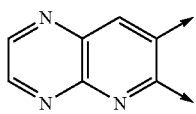

(r) 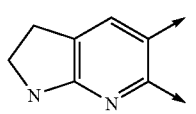

(s) 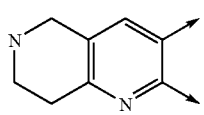

(t) 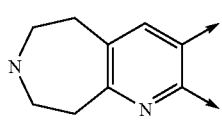

-continued (u) 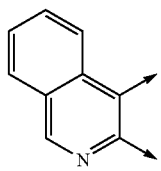

(v) 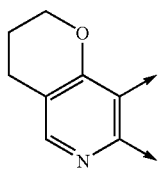

(w) 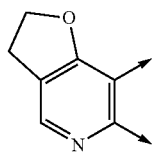

(x) 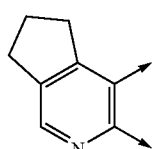

(y) 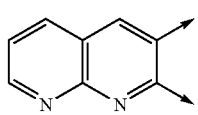

The "substituent" in the "optionally substituted cyclic group" represented by ring D is preferably, for example, an optionally substituted aliphatic hydrocarbon group, halogen, cyano, methyl which may be substituted by 1 to 3 of halogen atom(s) (e.g., methyl, fluoromethyl, difluoromethyl, trifluoromethyl, chloromethyl, dichloromethyl, trichloromethyl, bromomethyl, and the like), —COOR$^{a1}$, an optionally substituted 3- to 15-membered cyclic group, and the like; more preferably, for example, C1-8 alkyl, halogen, trifluoromethyl, an optionally substituted C3-10 mono- or bi-cyclic carbon ring, and the like; and especially preferably, for example, methyl, chlorine, bromine, trifluoromethyl, an optionally substituted benzene ring, and the like. The number of substituents of ring D is preferably 0 to 5, more preferably 0 to 2, and especially preferably 1 to 2.

G is preferably, for example, a spacer having 1 to 4 atom(s) in its main chain, and the like; more preferably, for example, a spacer having 1 to 4 atom(s) in its main chain and containing at least one nitrogen atom, and the like; and especially preferably, for example, —NR$^{T1}$—, —NR$^{T1}$—SO$_2$—, —NR$^{T1}$—CO—, —NR$^{T1}$—CO—NR$^{T2}$—, —NR$^{T1}$—SO$_2$—NR$^{T2}$—, —NR$^{T1}$—COO—, —NR$^{T1}$—O—, —NR$^{T1}$—NR$^{T2}$—, —NR$^{T1}$—W—, —SO$_2$—NR$^{T1}$—, —CO—NR$^{T1}$—, —OCO—NR$^{T1}$—, —O—NR$^{T1}$—, —W—NR$^{T1}$—, and the like. Among these, —NR$^{T1}$—SO$_2$— (wherein the nitrogen atom is bound to ring D, and the sulfur atom is bound to ring B) is preferred, and for example, —NH—SO$_2$— (wherein the nitrogen atom is bound to ring D, and the sulfur is bound to ring B) is especially preferred.

J is preferably, for example, a spacer having 1 to 8 atom(s) in its main chain, and the like; more preferably, for example, a spacer having 1 to 8 atom(s) in its main chain and containing at least one oxygen atom or one nitrogen atom (for example, the "spacer having 1 to 8 atom(s) in its main chain and containing at least one oxygen atom or one nitrogen atom" means a bivalent group which containing at least one —O— among the before-described spacer having 1 to 8 atom(s) in its main chain.), and the like; and especially preferably, for example, a spacer having 2 atoms in its main chain (for example, the "spacer having 2 atoms in its main chain" means a spacer having 2 atoms in its main chain among the before-described "spacer having 1 to 8 atom(s) in its main chain"), and the like. As especially preferable one, for example, —O—CH$_2$—, —NHCH$_2$—, and —NHCO—, and wherein the ring A is bound to the right side of each group) can be cited.

In the present invention, preferred is the compound represented by formula (I) comprising a combination of the above-described preferred groups and preferred rings.

As the preferred compounds among the compounds represented by formula (I), the compounds represented by formula (I-1):

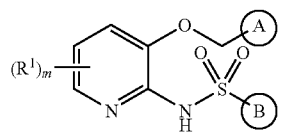
(I-1)

wherein R$^1$ is the before-described substituent of ring D, m is 0 or an integer of 1 to 3, and other symbols have the same meanings as described above, the compounds represented by formula (I-2):

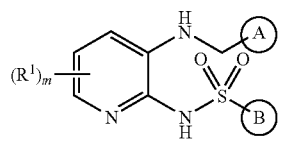
(I-2)

wherein all symbols have the same meanings as described above, the compounds represented by formula (I-3):

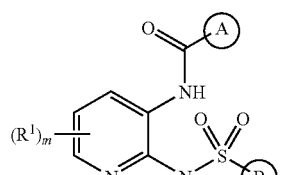
(I-3)

wherein all symbols have the same meanings as described above, the compounds represented by formula (I-4):

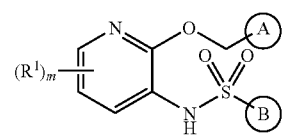
(I-4)

wherein all symbols have the same meanings as described above, the compounds represented by formula (I-5):

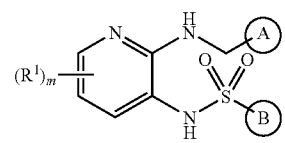
(I-5)

wherein all symbols have the same meanings as described above, the compounds represented by formula (I-6):

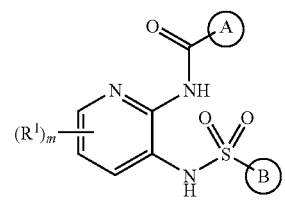
(I-6)

wherein all symbols have the same meanings as described above, the compounds represented by formula (I-7):

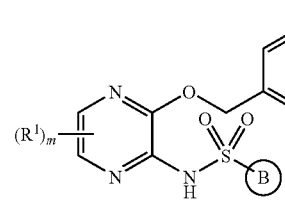
(I-7)

wherein R$^2$ is the before-described substituent of ring A, and other symbols have the same meanings as described above, the compounds represented by formula (I-8):

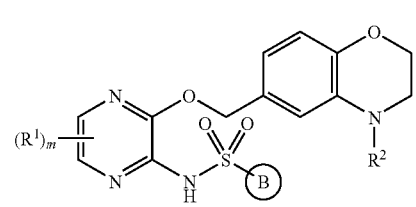
(I-8)

wherein all symbols have the same meanings as described above, the compounds represented by formula (I-9):

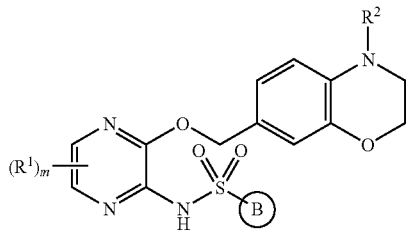

wherein all symbols have the same meanings as described above, or the compounds represented by formula (I-10):

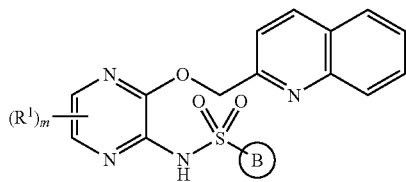

wherein all symbols have the same meanings as described above, a salt thereof, an N-oxide thereof, a solvate thereof or a pro drug thereof, and the like can be cited.

As the specifically preferable compounds, for example, the compounds described in the following (1) to (547) or Examples in the specification, a salt thereof, an N-oxide thereof, a solvate thereof or a prodrug thereof, and the like can be cited.

(1) 3-chloro-N-[3-({4-chloro-3-[(1-methylpiperidin-4-yl) methoxy]benzyl}oxy)pyrazin-2-yl]-2-methylbenzenesulfonamide,
(2) 3-chloro-2-methyl-N-{3-[(4-methyl-3,4-dihydro-2H-1, 4-benzoxazin-6-yl)methoxy]pyrazin-2-yl}benzenesulfonamide,
(3) 3-chloro-2-methyl-N-{3-[(4-methyl-3,4-dihydro-2H-1, 4-benzoxazin-7-yl)methoxy]pyrazin-2-yl}benzenesulfonamide,
(4) 3-chloro-2-methyl-N-[2-(pyridin-3-ylmethoxy)quinolin-3-yl]benzenesulfonamide,
(5) 3-chloro-N-{2-[(3,4-dimethoxybenzyl)oxy]quinolin-3-yl}-2-methylbenzenesulfonamide,
(6) 3-chloro-N-[2-({3-[2-(dimethylamino)ethoxy]-4-methoxybenzyl}oxy)quinolin-3-yl]-2-methylbenzenesulfonamide,
(7) 3-chloro-N-[2-({4-chloro-3-[(1-methylpiperidin-4-yl) methoxy]benzyl}oxy)quinolin-3-yl]-2-methylbenzenesulfonamide,
(8) 3-chloro-N-[2-({4-chloro-3-[2-(dimethylamino)ethoxy] benzyl}oxy)quinolin-3-yl]-2-methylbenzenesulfonamide,
(9) 3-chloro-2-methyl-N-{2-[(4-methyl-3,4-dihydro-2H-1, 4-benzoxazin-6-yl)methoxy]quinolin-3-yl}benzenesulfonamide,
(10) 3-chloro-2-methyl-N-{2-[(4-methyl-3,4-dihydro-2H-1, 4-benzoxazin-7-yl)methoxy]quinolin-3-yl}benzenesulfonamide,
(11) 3-chloro-2-methyl-N-[2-(2-phenoxyethoxy)quinolin-3-yl]benzenesulfonamide,
(12) 3-chloro-2-methyl-N-[3-(pyridin-3-ylmethoxy)quinolin-2-yl]benzenesulfonamide,
(13) 3-chloro-N-{3-[(3,4-dimethoxybenzyl)oxy]quinolin-2-yl}-2-methylbenzenesulfonamide,
(14) 3-chloro-N-[3-({3-[2-(dimethylamino)ethoxy]-4-methoxybenzyl}oxy)quinolin-2-yl]-2-methylbenzenesulfonamide,
(15) 3-chloro-N-[3-({4-chloro-3-[(1-methylpiperidin-4-yl) methoxy]benzyl}oxy)quinolin-2-yl]-2-methylbenzenesulfonamide,
(16) 3-chloro-N-[3-({4-chloro-3-[2-(dimethylamino) ethoxy]benzyl}oxy)quinolin-2-yl]-2-methylbenzenesulfonamide,
(17) 3-chloro-2-methyl-N-{3-[(4-methyl-3,4-dihydro-2H-1, 4-benzoxazin-6-yl)methoxy]quinolin-2-yl}benzenesulfonamide,
(18) 3-chloro-2-methyl-N-{3-[(4-methyl-3,4-dihydro-2H-1, 4-benzoxazin-7-yl)methoxy]quinolin-2-yl}benzenesulfonamide,
(19) 3-chloro-2-methyl-N-[3-(2-phenoxyethoxy)quinolin-2-yl]benzenesulfonamide,
(20) 3-chloro-2-methyl-N-[7-(pyridin-3-ylmethoxy)pyrido [2,3-d]pyrimidin-6-yl]benzenesulfonamide,
(21) 3-chloro-N-{7-[(3,4-dimethoxybenzyl)oxy]pyrido[2,3-d]pyrimidin-6-yl}-2-methylbenzenesulfonamide,
(22) 3-chloro-N-[7-({3-[2-(dimethylamino)ethoxy]-4-methoxybenzyl}oxy)pyrido[2,3-d]pyrimidin-6-yl]-2-methylbenzenesulfonamide,
(23) 3-chloro-N-[7-({4-chloro-3-[(1-methylpiperidin-4-yl) methoxy]benzyl}oxy)pyrido[2,3-d]pyrimidin-6-yl]-2-methylbenzenesulfonamide,
(24) 3-chloro-N-[7-({4-chloro-3-[2-(dimethylamino) ethoxy]benzyl}oxy)pyrido[2,3-d]pyrimidin-6-yl]-2-methylbenzenesulfonamide,
(25) 3-chloro-2-methyl-N-{7-[(4-methyl-3,4-dihydro-2H-1, 4-benzoxazin-6-yl)methoxy]pyrido[2,3-d]pyrimidin-6-yl}benzenesulfonamide,
(26) 3-chloro-2-methyl-N-{7-[(4-methyl-3,4-dihydro-2H-1, 4-benzoxazin-7-yl)methoxy]pyrido[2,3-d]pyrimidin-6-yl}benzenesulfonamide,
(27) 3-chloro-2-methyl-N-[7-(2-phenoxyethoxy)pyrido[2,3-d]pyrimidin-6-yl]benzenesulfonamide,
(28) 3-chloro-2-methyl-N-[6-(pyridin-3-ylmethoxy)pyrido [2,3-d]pyrimidin-7-yl]benzenesulfonamide,
(29) 3-chloro-N-{6-[(3,4-dimethoxybenzyl)oxy]pyrido[2,3-d]pyrimidin-7-yl}-2-methylbenzenesulfonamide,
(30) 3-chloro-N-[6-({3-[2-(dimethylamino)ethoxy]-4-methoxybenzyl}oxy)pyrido[2,3-d]pyrimidin-7-yl]-2-methylbenzenesulfonamide,
(31) 3-chloro-N-[6-({4-chloro-3-[(1-methylpiperidin-4-yl) methoxy]benzyl}oxy)pyrido[2,3-d]pyrimidin-7-yl]-2-methylbenzenesulfonamide,
(32) 3-chloro-N-[6-({4-chloro-3-[2-(dimethylamino) ethoxy]benzyl}oxy)pyrido[2,3-d]pyrimidin-7-yl]-2-methylbenzenesulfonamide,
(33) 3-chloro-2-methyl-N-{6-[(4-methyl-3,4-dihydro-2H-1, 4-benzoxazin-6-yl)methoxy]pyrido[2,3-d]pyrimidin-7-yl}benzenesulfonamide,
(34) 3-chloro-2-methyl-N-{6-[(4-methyl-3,4-dihydro-2H-1, 4-benzoxazin-7-yl)methoxy]pyrido[2,3-d]pyrimidin-7-yl}benzenesulfonamide,
(35) 3-chloro-2-methyl-N-[6-(2-phenoxyethoxy)pyrido[2,3-d]pyrimidin-7-yl]benzenesulfonamide,
(36) 3-chloro-2-methyl-N-[2-(pyridin-3-ylmethoxy)-5,6,7, 8-tetrahydroquinolin-3-yl]benzenesulfonamide,

(37) 3-chloro-N-{2-[(3,4-dimethoxybenzyl)oxy]-5,6,7,8-tetrahydroquinolin-3-yl}-2-methylbenzenesulfonamide,
(38) 3-chloro-N-[2-({3-[2-(dimethylamino)ethoxy]-4-methoxybenzyl}oxy)-5,6,7,8-tetrahydroquinolin-3-yl]-2-methylbenzenesulfonamide,
(39) 3-chloro-N-[2-({4-chloro-3-[(1-methylpiperidin-4-yl)methoxy]benzyl}oxy)-5,6,7,8-tetrahydroquinolin-3-yl]-2-methylbenzenesulfonamide,
(40) 3-chloro-N-[2-({4-chloro-3-[2-(dimethylamino)ethoxy]benzyl}oxy)-5,6,7,8-tetrahydroquinolin-3-yl]-2-methylbenzenesulfonamide,
(41) 3-chloro-2-methyl-N-{2-[(4-methyl-3,4-dihydro-2H-1,4-benzoxazin-6-yl)methoxy]-5,6,7,8-tetrahydroquinolin-3-yl}benzenesulfonamide,
(42) 3-chloro-2-methyl-N-{2-[(4-methyl-3,4-dihydro-2H-1,4-benzoxazin-7-yl)methoxy]-5,6,7,8-tetrahydroquinolin-3-yl}benzenesulfonamide,
(43) 3-chloro-2-methyl-N-[2-(2-phenoxyethoxy)-5,6,7,8-tetrahydroquinolin-3-yl]benzenesulfonamide,
(44) 3-chloro-2-methyl-N-[3-(pyridin-3-ylmethoxy)-5,6,7,8-tetrahydroquinolin-2-yl]benzenesulfonamide,
(45) 3-chloro-N-{3-[(3,4-dimethoxybenzyl)oxy]-5,6,7,8-tetrahydroquinolin-2-yl}-2-methylbenzenesulfonamide,
(46) 3-chloro-N-[3-({3-[2-(dimethylamino)ethoxy]-4-methoxybenzyl}oxy)-5,6,7,8-tetrahydroquinolin-2-yl]-2-methylbenzenesulfonamide,
(47) 3-chloro-N-[3-({4-chloro-3-[(1-methylpiperidin-4-yl)methoxy]benzyl}oxy)-5,6,7,8-tetrahydroquinolin-2-yl]-2-methylbenzenesulfonamide,
(48) 3-chloro-N-[3-({4-chloro-3-[2-(dimethylamino)ethoxy]benzyl}oxy)-5,6,7,8-tetrahydroquinolin-2-yl]-2-methylbenzenesulfonamide,
(49) 3-chloro-2-methyl-N-{3-[(4-methyl-3,4-dihydro-2H-1,4-benzoxazin-6-yl)methoxy]-5,6,7,8-tetrahydroquinolin-2-yl}benzenesulfonamide,
(50) 3-chloro-2-methyl-N-{3-[(4-methyl-3,4-dihydro-2H-1,4-benzoxazin-7-yl)methoxy]-5,6,7,8-tetrahydroquinolin-2-yl}benzenesulfonamide,
(51) 3-chloro-2-methyl-N-[3-(2-phenoxyethoxy)-5,6,7,8-tetrahydroquinolin-2-yl]benzenesulfonamide,
(52) 3-chloro-2-methyl-N-[3-(pyridin-3-ylmethoxy)isoquinolin-4-yl]benzenesulfonamide,
(53) 3-chloro-N-{3-[(3,4-dimethoxybenzyl)oxy]isoquinolin-4-yl}-2-methylbenzenesulfonamide,
(54) 3-chloro-N-[3-({3-[2-(dimethylamino)ethoxy]-4-methoxybenzyl}oxy)isoquinolin-4-yl]-2-methylbenzenesulfonamide,
(55) 3-chloro-N-[3-({4-chloro-3-[(1-methylpiperidin-4-yl)methoxy]benzyl}oxy)isoquinolin-4-yl]-2-methylbenzenesulfonamide,
(56) 3-chloro-N-[3-({4-chloro-3-[2-(dimethylamino)ethoxy]benzyl}oxy)isoquinolin-4-yl]-2-methylbenzenesulfonamide,
(57) 3-chloro-2-methyl-N-{3-[(4-methyl-3,4-dihydro-2H-1,4-benzoxazin-6-yl)methoxy]isoquinolin-4-yl}benzenesulfonamide,
(58) 3-chloro-2-methyl-N-{3-[(4-methyl-3,4-dihydro-2H-1,4-benzoxazin-7-yl)methoxy]isoquinolin-4-yl}benzenesulfonamide,
(59) 3-chloro-2-methyl-N-[3-(2-phenoxyethoxy)isoquinolin-4-yl]benzenesulfonamide,
(60) 3-chloro-2-methyl-N-[4-(pyridin-3-ylmethoxy)isoquinolin-3-yl]benzenesulfonamide,
(61) 3-chloro-N-{4-[(3,4-dimethoxybenzyl)oxy]isoquinolin-3-yl}-2-methylbenzenesulfonamide,
(62) 3-chloro-N-[4-({3-[2-(dimethylamino)ethoxy]-4-methoxybenzyl}oxy)isoquinolin-3-yl]-2-methylbenzenesulfonamide,
(63) 3-chloro-N-[4-({4-chloro-3-[(1-methylpiperidin-4-yl)methoxy]benzyl}oxy)isoquinolin-3-yl]-2-methylbenzenesulfonamide,
(64) 3-chloro-N-[4-({4-chloro-3-[2-(dimethylamino)ethoxy]benzyl}oxy)isoquinolin-3-yl]-2-methylbenzenesulfonamide,
(65) 3-chloro-2-methyl-N-{4-[(4-methyl-3-4-dihydro-2H-1,4-benzoxazin-6-yl)methoxy]isoquinolin-3-yl}benzenesulfonamide,
(66) 3-chloro-2-methyl-N-{4-[(4-methyl-3,4-dihydro-2H-1,4-benzoxazin-7-yl)methoxy]isoquinolin-3-yl}benzenesulfonamide,
(67) 3-chloro-2-methyl-N-[4-(2-phenoxyethoxy)isoquinolin-3-yl]benzenesulfonamide,
(68) 3-chloro-2-methyl-N-[2-oxo-6-(pyridin-3-ylmethoxy)-2,3-dihydro-1H-pyrrolo[2,3-b]pyridin-5-yl]benzenesulfonamide,
(69) 3-chloro-N-{6-[(3,4-dimethoxybenzyl)oxy]-2-oxo-2,3-dihydro-1H-pyrrolo[2,3-b]pyridin-5-yl}-2-methylbenzenesulfonamide,
(70) 3-chloro-N-[6-({3-[2-(dimethylamino)ethoxy]-4-methoxybenzyl}oxy)-2-oxo-2,3-dihydro-1H-pyrrolo[2,3-b]pyridin-5-yl]-2-methylbenzenesulfonamide,
(71) 3-chloro-N-[6-({4-chloro-3-[(1-methylpiperidin-4-yl)methoxy]benzyl}oxy)-2-oxo-2,3-dihydro-1H-pyrrolo[2,3-b]pyridin-5-yl]-2-methylbenzenesulfonamide,
(72) 3-chloro-N-[6-({4-chloro-3-[2-(dimethylamino)ethoxy]benzyl}oxy)-2-oxo-2,3-dihydro-1H-pyrrolo[2,3-b]pyridin-5-yl]-2-methylbenzenesulfonamide,
(73) 3-chloro-2-methyl-N-{6-[(4-methyl-3,4-dihydro-2H-1,4-benzoxazin-6-yl)methoxy]-2-oxo-2,3-dihydro-1H-pyrrolo[2,3-b]pyridin-5-yl}benzenesulfonamide,
(74) 3-chloro-2-methyl-N-{6-[(4-methyl-3,4-dihydro-2H-1,4-benzoxazin-7-yl)methoxy]-2-oxo-2,3-dihydro-1H-pyrrolo[2,3-b]pyridin-5-yl}benzenesulfonamide,
(75) 3-chloro-2-methyl-N-[2-oxo-6-(2-phenoxyethoxy)-2,3-dihydro-1H-pyrrolo[2,3-b]pyridin-5-yl]benzenesulfonamide,
(76) 3-chloro-2-methyl-N-[2-oxo-5-(pyridin-3-ylmethoxy)-2,3-dihydro-1H-pyrrolo[2,3-b]pyridin-6-yl]benzenesulfonamide,
(77) 3-chloro-N-{5-[(3,4-dimethoxybenzyl)oxy]-2-oxo-2,3-dihydro-1H-pyrrolo[2,3-b]pyridin-6-yl}-2-methylbenzenesulfonamide,
(78) 3-chloro-N-[5-({3-[2-(dimethylamino)ethoxy]-4-methoxybenzyl}oxy)-2-oxo-2,3-dihydro-1H-pyrrolo[2,3-b]pyridin-6-yl]-2-methylbenzenesulfonamide,
(79) 3-chloro-N-[5-({4-chloro-3-[(1-methylpiperidin-4-yl)methoxy]benzyl}oxy)-2-oxo-2,3-dihydro-1H-pyrrolo[2,3-b]pyridin-6-yl]-2-methylbenzenesulfonamide,
(80) 3-chloro-N-[5-({4-chloro-3-[2-(dimethylamino)ethoxy]benzyl}oxy)-2-oxo-2,3-dihydro-1H-pyrrolo[2,3-b]pyridin-6-yl]-2-methylbenzenesulfonamide,
(81) 3-chloro-2-methyl-N-{5-[(4-methyl-3,4-dihydro-2H-1,4-benzoxazin-6-yl)methoxy]-2-oxo-2,3-dihydro-1H-pyrrolo[2,3-b]pyridin-6-yl}benzenesulfonamide,
(82) 3-chloro-2-methyl-N-{5-[(4-methyl-3,4-dihydro-2H-1,4-benzoxazin-7-yl)methoxy]-2-oxo-2,3-dihydro-1H-pyrrolo[2,3-b]pyridin-6-yl}benzenesulfonamide,
(83) 3-chloro-2-methyl-N-[2-oxo-5-(2-phenoxyethoxy)-2,3-dihydro-1H-pyrrolo[2,3-b]pyridin-6-yl]benzenesulfonamide,

(84) 3-chloro-2-methyl-N-[6-methyl-2-(pyridin-3-yl-methoxy)-5,6,7,8-tetrahydro-1,6-naphthyridin-3-yl]benzenesulfonamide,

(85) 3-chloro-N-{2-[(3,4-dimethoxybenzyl)oxy]-6-methyl-5,6,7,8-tetrahydro-1,6-naphthyridin-3-yl}-2-methylbenzenesulfonamide,

(86) 3-chloro-N-[2-({3-[2-(dimethylamino)ethoxy]-4-methoxybenzyl}oxy)-6-methyl-5,6,7,8-tetrahydro-1,6-naphthyridin-3-yl]-2-methylbenzenesulfonamide,

(87) 3-chloro-N-[2-({4-chloro-3-[(1-methylpiperidin-4-yl)methoxy]benzyl}oxy)-6-methyl-5,6,7,8-tetrahydro-1,6-naphthyridin-3-yl]-2-methylbenzenesulfonamide,

(88) 3-chloro-N-[2-({4-chloro-3-[2-(dimethylamino)ethoxy]benzyl}oxy)-6-methyl-5,6,7,8-tetrahydro-1,6-naphthyridin-3-yl]-2-methylbenzenesulfonamide,

(89) 3-chloro-2-methyl-N-{6-methyl-2-[(4-methyl-3,4-dihydro-2H-1,4-benzoxazin-6-yl)methoxy]-5,6,7,8-tetrahydro-1,6-naphthyridin-3-yl}benzenesulfonamide,

(90) 3-chloro-2-methyl-N-{6-methyl-2-[(4-methyl-3,4-dihydro-2H-1,4-benzoxazin-7-yl)methoxy]-5,6,7,8-tetrahydro-1,6-naphthyridin-3-yl}benzenesulfonamide,

(91) 3-chloro-2-methyl-N-[6-methyl-2-(2-phenoxyethoxy)-5,6,7,8-tetrahydro-1,6-naphthyridin-3-yl]benzenesulfonamide,

(92) 3-chloro-2-methyl-N-[6-methyl-3-(pyridin-3-yl-methoxy)-5,6,7,8-tetrahydro-1,6-naphthyridin-2-yl]benzenesulfonamide,

(93) 3-chloro-N-{3-[(3,4-dimethoxybenzyl)oxy]-6-methyl-5,6,7,8-tetrahydro-1,6-naphthyridin-2-yl}-2-methylbenzenesulfonamide,

(94) 3-chloro-N-[3-({3-[2-(dimethylamino)ethoxy]-4-methoxybenzyl}oxy)-6-methyl-5,6,7,8-tetrahydro-1,6-naphthyridin-2-yl]-2-methylbenzenesulfonamide,

(95) 3-chloro-N-[3-({4-chloro-3-[(1-methylpiperidin-4-yl)methoxy]benzyl}oxy)-6-methyl-5,6,7,8-tetrahydro-1,6-naphthyridin-2-yl]-2-methylbenzenesulfonamide,

(96) 3-chloro-N-[3-({4-chloro-3-[2-(dimethylamino)ethoxy]benzyl}oxy)-6-methyl-5,6,7,8-tetrahydro-1,6-naphthyridin-2-yl]-2-methylbenzenesulfonamide,

(97) 3-chloro-2-methyl-N-{6-methyl-3-[(4-methyl-3,4-dihydro-2H-1,4-benzoxazin-6-yl)methoxy]-5,6,7,8-tetrahydro-1,6-naphthyridin-2-yl}benzenesulfonamide,

(98) 3-chloro-2-methyl-N-{6-methyl-3-[(4-methyl-3,4-dihydro-2H-1,4-benzoxazin-7-yl)methoxy]-5,6,7,8-tetrahydro-1,6-naphthyridin-2-yl}benzenesulfonamide,

(99) 3-chloro-2-methyl-N-[6-methyl-3-(2-phenoxyethoxy)-5,6,7,8-tetrahydro-1,6-naphthyridin-2-yl]benzenesulfonamide, (100) 3-chloro-2-methyl-N-[2-(pyridin-3-ylmethoxy)-6,7-dihydro-5H-cyclopenta[b]pyridin-3-yl]benzenesulfonamide, (101) 3-chloro-N-{2-[(3,4-dimethoxybenzyl)oxy]-6,7-dihydro-5H-cyclopent[b]pyridin-3-yl}-2-methylbenzenesulfonamide, (102) 3-chloro-N-[2-({3-[2-(dimethylamino)ethoxy]-4-methoxybenzyl}oxy)-6,7-dihydro-5H-cyclopent[b]pyridin-3-yl]-2-methylbenzenesulfonamide, (103) 3-chloro-N-[2-({4-chloro-3-[(1-methylpiperidin-4-yl)methoxy]benzyl}oxy)-6,7-dihydro-5H-cyclopent[b]pyridin-3-yl]-2-methylbenzenesulfonamide, (104) 3-chloro-N-[2-({4-chloro-3-[2-(dimethylamino)ethoxy]benzyl}oxy)-6,7-dihydro-5H-cyclopent[b]pyridin-3-yl]-2-methylbenzenesulfonamide, (105) 3-chloro-2-methyl-N-{2-[(4-methyl-3,4-dihydro-2H-1,4-benzoxazin-6-yl)methoxy]-6,7-dihydro-5H-cyclopent[b]pyridin-3-yl}benzenesulfonamide, (106) 3-chloro-2-methyl-N-{2-[(4-methyl-3,4-dihydro-2H-1,4-benzoxazin-7-yl)methoxy]-6,7-dihydro-5H-cyclopent[b]pyridin-3-yl}benzenesulfonamide, (107) 3-chloro-2-methyl-N-[2-(2-phenoxyethoxy)-6,7-dihydro-5H-cyclopent[b]pyridin-3-yl]benzenesulfonamide, (108) 3-chloro-2-methyl-N-[4-(pyridin-3-ylmethoxy)-6,7-dihydro-5H-cyclopent[b]pyridin-3-yl]benzenesulfonamide, (109) 3-chloro-N-{4-[(3,4-dimethoxybenzyl)oxy]-6,7-dihydro-5H-cyclopent[b]pyridin-3-yl}-2-methylbenzenesulfonamide, (110) 3-chloro-N-[4-({3-[2-(dimethylamino)ethoxy]-4-methoxybenzyl}oxy)-6,7-dihydro-5H-cyclopent[b]pyridin-3-yl]-2-methylbenzenesulfonamide, (111) 3-chloro-N-[4-({4-chloro-3-[(1-methylpiperidin-4-yl)methoxy]benzyl}oxy)-6,7-dihydro-5H-cyclopent[b]pyridin-3-yl]-2-methylbenzenesulfonamide, (112) 3-chloro-N-[4-({4-chloro-3-[2-(dimethylamino)ethoxy]benzyl}oxy)-6,7-dihydro-5H-cyclopent[b]pyridin-3-yl]-2-methylbenzenesulfonamide, (113) 3-chloro-2-methyl-N-{4-[(4-methyl-3,4-dihydro-2H-1,4-benzoxazin-6-yl)methoxy]-6,7-dihydro-5H-cyclopent[b]pyridin-3-yl}benzenesulfonamide, (114) 3-chloro-2-methyl-N-{4-[(4-methyl-3,4-dihydro-2H-1,4-benzoxazin-7-yl)methoxy]-6,7-dihydro-5H-cyclopent[b]pyridin-3-yl}benzenesulfonamide, (115) 3-chloro-2-methyl-N-[4-(2-phenoxyethoxy)-6,7-dihydro-5H-cyclopent[b]pyridin-3-yl]benzenesulfonamide, (116) 3-chloro-2-methyl-N-[3-(pyridin-3-ylmethoxy)-6,7-dihydro-5H-cyclopent[b]pyridin-2-yl]benzenesulfonamide, (117) 3-chloro-N-{3-[(3,4-dimethoxybenzyl)oxy]-6,7-dihydro-5H-cyclopent[b]pyridin-2-yl}-2-methylbenzenesulfonamide, (118) 3-chloro-N-[3-({3-[2-(dimethylamino)ethoxy]-4-methoxybenzyl}oxy)-6,7-dihydro-5H-cyclopent[b]pyridin-2-yl]-2-methylbenzenesulfonamide, (119) 3-chloro-N-[3-({4-chloro-3-[(1-methylpiperidin-4-yl)methoxy]benzyl}oxy)-6,7-dihydro-5H-cyclopent[b]pyridin-2-yl]-2-methylbenzenesulfonamide, (120) 3-chloro-N-[3-({4-chloro-3-[2-(dimethylamino)ethoxy]benzyl}oxy)-6,7-dihydro-5H-cyclopent[b]pyridin-2-yl]-2-methylbenzenesulfonamide, (121) 3-chloro-2-methyl-N-{3-[(4-methyl-3,4-dihydro-2H-1,4-benzoxazin-6-yl)methoxy]-6,7-dihydro-5H-cyclopent[b]pyridin-2-yl}benzenesulfonamide, (122) 3-chloro-2-methyl-N-{3-[(4-methyl-3,4-dihydro-2H-1,4-benzoxazin-7-yl)methoxy]-6,7-dihydro-5H-cyclopent[b]pyridin-2-yl}benzenesulfonamide, (123) 3-chloro-2-methyl-N-[3-(2-phenoxyethoxy)-6,7-dihydro-5H-cyclopent[b]pyridin-2-yl]benzenesulfonamide, (124) 3-chloro-2-methyl-N-[3-(pyridin-3-ylmethoxy)-6,7-dihydro-5H-cyclopent[b]pyridin-4-yl]benzenesulfonamide, (125) -3-chloro-N-{3-[(3,4-dimethoxybenzyl)oxy]-6,7-dihydro-5H-cyclopent[b]pyridin-4-yl}-2-methylbenzenesulfonamide, (126) 3-chloro-N-[3-({3-[2-(dimethylamino)ethoxy]-4-methoxybenzyl}oxy)-6,7-dihydro-5H-cyclopent[b]pyridin-4-yl]-2-methylbenzenesulfonamide, (127) 3-chloro-N-[3-({4-chloro-3-[(1-methylpiperidin-4-yl)methoxy]benzyl}oxy)-6,7-dihydro-5H-cyclopent[b]pyridin-4-yl]-2-methylbenzenesulfonamide, (128) 3-chloro-N-[3-({4-chloro-3-[2-(dimethylamino)ethoxy]benzyl}oxy)-6,7-dihydro-5H-cyclopent[b]pyridin-4-yl]-2-methylbenzenesulfonamide, (129) 3-chloro-2-methyl-N-{3-[(4-methyl-3,4-dihydro-2H-1,4-benzoxazin-6-yl)methoxy]-6,7-dihydro-5H-cyclopent[b]pyridin-4-yl}benzenesulfonamide,
(130) 3-chloro-2-methyl-N-{3-[(4-methyl-3,4-dihydro-2H-1,4-benzoxazin-7-yl)methoxy]-6,7-dihydro-5H-cyclopent[b]pyridin-4-yl}benzenesulfonamide,
(131) 3-chloro-2-methyl-N-[3-(2-phenoxyethoxy)-6,7-dihydro-5H-cyclopent[b]pyridin-4-yl]benzenesulfonamide,
(132) 3-chloro-N-[7-ethyl-2-(pyridin-3-ylmethoxy)-6,7,8,9-tetrahydro-5H-pyrido[2,3-d]azepin-3-yl]-2-methylbenzenesulfonamide,
(133) 3-chloro-N-{2-[(3,4-dimethoxybenzyl)oxy]-7-ethyl-6,7,8,9-tetrahydro-5H-pyrido[2,3-d]azepin-3-yl}-2-methylbenzenesulfonamide,
(134) 3-chloro-N-[2-({3-[2-(dimethylamino)ethoxy]-4-methoxybenzyl}oxy)-7-ethyl-6,7,8,9-tetrahydro-5H-pyrido[2,3-d]azepin-3-yl]-2-methylbenzenesulfonamide,
(135) 3-chloro-N-[2-({4-chloro-3-[(1-methylpiperidin-4-yl)methoxy]benzyl}oxy)-7-ethyl-6,7,8,9-tetrahydro-5H-pyrido[2,3-d]azepin-3-yl]-2-methylbenzenesulfonamide,
(136) 3-chloro-N-[2-({4-chloro-3-[2-(dimethylamino)ethoxy]benzyl}oxy)-7-ethyl-6,7,8,9-tetrahydro-5H-pyrido[2,3-d]azepin-3-yl]-2-methylbenzenesulfonamide,
(137) 3-chloro-N-{7-ethyl-2-[(4-methyl-3,4-dihydro-2H-1,4-benzoxazin-6-yl)methoxy]-6,7,8,9-tetrahydro-5H-pyrido[2,3-d]azepin-3-yl}-2-methylbenzenesulfonamide,
(138) 3-chloro-N-{7-ethyl-2-[(4-methyl-3,4-dihydro-2H-1,4-benzoxazin-7-yl)methoxy]-6,7,8,9-tetrahydro-5H-pyrido[2,3-d]azepin-3-yl}-2-methylbenzenesulfonamide,
(139) 3-chloro-N-[7-ethyl-2-(2-phenoxyethoxy)-6,7,8,9-tetrahydro-5H-pyrido[2,3-d]azepin-3-yl]-2-methylbenzenesulfonamide,
(140) 3-chloro-N-[7-ethyl-3-(pyridin-3-ylmethoxy)-6,7,8,9-tetrahydro-5H-pyrido[2,3-d]azepin-2-yl]-2-methylbenzenesulfonamide,
(141) 3-chloro-N-{3-[(3,4-dimethoxybenzyl)oxy]-7-ethyl-6,7,8,9-tetrahydro-5H-pyrido[2,3-d]azepin-2-yl}-2-methylbenzenesulfonamide,
(142) 3-chloro-N-[3-({3-[2-(dimethylamino)ethoxy]-4-methoxybenzyl}oxy)-7-ethyl-6,7,8,9-tetrahydro-5H-pyrido[2,3-d]azepin-2-yl]-2-methylbenzenesulfonamide,
(143) 3-chloro-N-[3-({4-chloro-3-[(1-methylpiperidin-4-yl)methoxy]benzyl}oxy)-7-ethyl-6,7,8,9-tetrahydro-5H-pyrido[2,3-d]azepin-2-yl]-2-methylbenzenesulfonamide,
(144) 3-chloro-N-[3-({4-chloro-3-[2-(dimethylamino)ethoxy]benzyl}oxy)-7-ethyl-6,7,8,9-tetrahydro-5H-pyrido[2,3-d]azepin-2-yl]-2-methylbenzenesulfonamide,
(145) 3-chloro-N-{7-ethyl-3-[(4-methyl-3,4-dihydro-2H-1,4-benzoxazin-6-yl)methoxy]-6,7,8,9-tetrahydro-5H-pyrido[2,3-d]azepin-2-yl}-2-methylbenzenesulfonamide,
(146) 3-chloro-N-{7-ethyl-3-[(4-methyl-3,4-dihydro-2H-1,4-benzoxazin-7-yl)methoxy]-6,7,8,9-tetrahydro-5H-pyrido[2,3-d]azepin-2-yl}-2-methylbenzenesulfonamide,
(147) 3-chloro-N-[7-ethyl-3-(2-phenoxyethoxy)-6,7,8,9-tetrahydro-5H-pyrido[2,3-d]azepin-2-yl]-2-methylbenzenesulfonamide,
(148) 3-chloro-2-methyl-N-[6-(pyridin-3-ylmethoxy)furo[3,2-b]pyridin-5-yl]benzenesulfonamide,
(149) 3-chloro-N-{6-[(3,4-dimethoxybenzyl)oxy]furo[3,2-b]pyridin-5-yl}-2-methylbenzenesulfonamide,
(150) 3-chloro-N-[6-({3-[2-(dimethylamino)ethoxy]-4-methoxybenzyl}oxy)furo[3,2-b]pyridin-5-yl]-2-methylbenzenesulfonamide,
(151) 3-chloro-N-[6-({4-chloro-3-[(1-methylpiperidin-4-yl)methoxy]benzyl}oxy)furo[3,2-b]pyridin-5-yl]-2-methylbenzenesulfonamide,
(152) 3-chloro-N-[6-({4-chloro-3-[2-(dimethylamino)ethoxy]benzyl}oxy)furo[3,2-b]pyridin-5-yl]-2-methylbenzenesulfonamide,
(153) 3-chloro-2-methyl-N-{6-[(4-methyl-3,4-dihydro-2H-1,4-benzoxazin-6-yl)methoxy]furo[3,2-b]pyridin-5-yl}benzenesulfonamide,
(154) 3-chloro-2-methyl-N-{6-[(4-methyl-3,4-dihydro-2H-1,4-benzoxazin-7-yl)methoxy]furo[3,2-b]pyridin-5-yl}benzenesulfonamide,
(155) 3-chloro-2-methyl-N-[6-(2-phenoxyethoxy)furo[3,2-b]pyridin-5-yl]benzenesulfonamide,
(156) 3-chloro-2-methyl-N-[5-(pyridin-3-ylmethoxy)furo[3,2-b]pyridin-6-yl]benzenesulfonamide,
(157) 3-chloro-N-{5-[(3,4-dimethoxybenzyl)oxy]furo[3,2-b]pyridin-6-yl}-2-methylbenzenesulfonamide,
(158) 3-chloro-N-[5-({3-[2-(dimethylamino)ethoxy]-4-methoxybenzyl}oxy)furo[3,2-b]pyridin-6-yl]-2-methylbenzenesulfonamide,
(159) 3-chloro-N-[5-({4-chloro-3-[(1-methylpiperidin-4-yl)methoxy]benzyl}oxy)furo[3,2-b]pyridin-6-yl]-2-methylbenzenesulfonamide,
(160) 3-chloro-N-[5-({4-chloro-3-[2-(dimethylamino)ethoxy]benzyl}oxy)furo[3,2-b]pyridin-6-yl]-2-methylbenzenesulfonamide,
(161) 3-chloro-2-methyl-N-{5-[(4-methyl-3,4-dihydro-2H-1,4-benzoxazin-6-yl)methoxy]furo[3,2-b]pyridin-6-yl}benzenesulfonamide,
(162) 3-chloro-2-methyl-N-{5-[(4-methyl-3,4-dihydro-2H-1,4-benzoxazin-7-yl)methoxy]furo[3,2-b]pyridin-6-yl}benzenesulfonamide,
(163) 3-chloro-2-methyl-N-[5-(2-phenoxyethoxy)furo[3,2-b]pyridin-6-yl]benzenesulfonamide,
(164) 3-chloro-2-methyl-N-[2-(pyridin-3-ylmethoxy)-1,6-naphthyridin-3-yl]benzenesulfonamide,
(165) 3-chloro-N-{2-[(3,4-dimethoxybenzyl)oxy]-1,6-naphthyridine3-yl}-2-methylbenzenesulfonamide,
(166) 3-chloro-N-[2-({3-[2-(dimethylamino)ethoxy]-4-methoxybenzyl}oxy)-1,6-naphthyridine3-yl]-2-methylbenzenesulfonamide,
(167) 3-chloro-N-[2-({4-chloro-3-[(1-methylpiperidin-4-yl)methoxy]benzyl}oxy)-1,6-naphthyridine3-yl]-2-methylbenzenesulfonamide,
(168) 3-chloro-N-[2-({4-chloro-3-[2-(dimethylamino)ethoxy]benzyl}oxy)-1,6-naphthyridine3-yl]-2-methylbenzenesulfonamide,
(169) 3-chloro-2-methyl-N-{2-[(4-methyl-3,4-dihydro-2H-1,4-benzoxazin-6-yl)methoxy]-1,6-naphthyridine3-yl}benzenesulfonamide,
(170) 3-chloro-2-methyl-N-{2-[(4-methyl-3,4-dihydro-2H-1,4-benzoxazin-7-yl)methoxy]-1,6-naphthyridine3-yl}benzenesulfonamide,
(171) 3-chloro-2-methyl-N-[2-(2-phenoxyethoxy)-1,6-naphthyridine3-yl]benzenesulfonamide,
(172) 3-chloro-2-methyl-N-[3-(pyridin-3-ylmethoxy)-1,6-naphthyridine2-yl]benzenesulfonamide,
(173) 3-chloro-N-{3-[(3,4-dimethoxybenzyl)oxy]-1,6-naphthyridine2-yl}-2-methylbenzenesulfonamide,
(174) 3-chloro-N-[3-({3-[2-(dimethylamino)ethoxy]-4-methoxybenzyl}oxy)-1,6-2-yl]-2-methylbenzenesulfonamide,
(175) 3-chloro-N-[3-({4-chloro-3-[(1-methylpiperidin-4-yl)methoxy]benzyl}oxy)-1,6-naphthyridine2-yl]-2-methylbenzenesulfonamide,
(176) 3-chloro-N-[3-({4-chloro-3-[2-(dimethylamino)ethoxy]benzyl}oxy)-1,6-naphthyridine2-yl]-2-methylbenzenesulfonamide, (177) 3-chloro-2-methyl-N-{3-[(4-methyl-3,4-dihydro-2H-1,4-benzoxazin-6-yl)methoxy]-1,6-naphthyridine2-yl}benzenesulfonamide,
(178) 3-chloro-2-methyl-N-{3-[(4-methyl-3,4-dihydro-2H-1,4-benzoxazin-7-yl)methoxy]-1,6-naphthyridine2-yl}benzenesulfonamide,
(179) 3-chloro-2-methyl-N-[3-(2-phenoxyethoxy)-1,6-naphthyridine2-yl]benzenesulfonamide,
(180) 3-chloro-2-methyl-N-[6-(pyridin-3-ylmethoxy)pyrido[2,3-b]pyrazin-7-yl]benzenesulfonamide,
(181) 3-chloro-N-{6-[(3,4-dimethoxybenzyl)oxy]pyrido[2,3-b]pyrazin-7-yl}-2-methylbenzenesulfonamide,
(182) 3-chloro-N-[6-({3-[2-(dimethylamino)ethoxy]-4-methoxybenzyl}oxy)pyrido[2,3-b]pyrazin-7-yl]-2-methylbenzenesulfonamide,
(183) 3-chloro-N-[6-({4-chloro-3-[(1-methylpiperidin-4-yl)methoxy]benzyl}oxy)pyrido[2,3-b]pyrazin-7-yl]-2-methylbenzenesulfonamide,
(184) 3-chloro-N-[6-({4-chloro-3-[2-(dimethylamino)ethoxy]benzyl}oxy)pyrido[2,3-b]pyrazin-7-yl]-2-methylbenzenesulfonamide,
(185) 3-chloro-2-methyl-N-{6-[(4-methyl-3,4-dihydro-2H-1,4-benzoxazin-6-yl)methoxy]pyrido[2,3-b]pyrazin-7-yl}benzenesulfonamide,
(186) 3-chloro-2-methyl-N-{6-[(4-methyl-3,4-dihydro-2H-1,4-benzoxazin-7-yl)methoxy]pyrido[2,3-b]pyrazin-7-yl}benzenesulfonamide,
(187) 3-chloro-2-methyl-N-[6-(2-phenoxyethoxy)pyrido[2,3-b]pyrazin-7-yl]benzenesulfonamide,
(188) 3-chloro-2-methyl-N-[7-(pyridin-3-ylmethoxy)pyrido[2,3-b]pyrazin-6-yl]benzenesulfonamide,
(189) 3-chloro-N-{7-[(3,4-dimethoxybenzyl)oxy]pyrido[2,3-b]pyrazin-6-yl}-2-methylbenzenesulfonamide,
(190) 3-chloro-N-[7-({3-[2-(dimethylamino)ethoxy]-4-methoxybenzyl}oxy)pyrido[2,3-b]pyrazin-6-yl]-2-methylbenzenesulfonamide,
(191) 3-chloro-N-[7-({4-chloro-3-[(1-methylpiperidin-4-yl)methoxy]benzyl}oxy)pyrido[2,3-b]pyrazin-6-yl]-2-methylbenzenesulfonamide,
(192) 3-chloro-N-[7-({4-chloro-3-[2-(dimethylamino)ethoxy]benzyl}oxy)pyrido[2,3-b]pyrazin-6-yl]-2-methylbenzenesulfonamide,
(193) 3-chloro-2-methyl-N-{7-[(4-methyl-3,4-dihydro-2H-1,4-benzoxazin-6-yl)methoxy]pyrido[2,3-b]pyrazin-6-yl}benzenesulfonamide,
(194) 3-chloro-2-methyl-N-{7-[(4-methyl-3,4-dihydro-2H-1,4-benzoxazin-7-yl)methoxy]pyrido[2,3-b]pyrazin-6-yl}benzenesulfonamide,
(195) 3-chloro-2-methyl-N-[7-(2-phenoxyethoxy)pyrido[2,3-b]pyrazin-6-yl]benzenesulfonamide,
(196) 3-chloro-2-methyl-N-[6-(pyridin-3-ylmethoxy)-2,3-dihydrofuro[3,2-c]pyridin-7-yl]benzenesulfonamide,
(197) 3-chloro-N-{6-[(3,4-dimethoxybenzyl)oxy]-2,3-dihydrofuro[3,2-c]pyridin-7-yl}-2-methylbenzenesulfonamide,
(198) 3-chloro-N-[6-({3-[2-(dimethylamino)ethoxy]-4-methoxybenzyl}oxy)-2,3-dihydrofuro[3,2-c]pyridin-7-yl]-2-methylbenzenesulfonamide,
(199) 3-chloro-N-[6-({4-chloro-3-[(1-methylpiperidin-4-yl)methoxy]benzyl}oxy)-2,3-dihydrofuro[3,2-c]pyridin-7-yl]-2-methylbenzenesulfonamide,
(200) 3-chloro-N-[6-({4-chloro-3-[2-(dimethylamino)ethoxy]benzyl}oxy)-2,3-dihydrofuro[3,2-c]pyridin-7-yl]-2-methylbenzenesulfonamide,
(201) 3-chloro-2-methyl-N-{6-[(4-methyl-3,4-dihydro-2H-1,4-benzoxazin-6-yl)methoxy]-2,3-dihydrofuro[3,2-c]pyridin-7-yl}benzenesulfonamide,
(202) 3-chloro-2-methyl-N-{6-[(4-methyl-3,4-dihydro-2H-1,4-benzoxazin-7-yl)methoxy]-2,3-dihydrofuro[3,2-c]pyridin-7-yl}benzenesulfonamide,
(203) 3-chloro-2-methyl-N-[6-(2-phenoxyethoxy)-2,3-dihydrofuro[3,2-c]pyridin-7-yl]benzenesulfonamide,
(204) 3-chloro-2-methyl-N-[7-(pyridin-3-ylmethoxy)-2,3-dihydrofuro[3,2-c]pyridin-6-yl]benzenesulfonamide,
(205) 3-chloro-N-{7-[(3,4-dimethoxybenzyl)oxy]-2,3-dihydrofuro[3,2-c]pyridin-6-yl}-2-methylbenzenesulfonamide,
(206) 3-chloro-N-[7-({3-[2-(dimethylamino)ethoxy]-4-methoxybenzyl}oxy)-2,3-dihydrofuro[3,2-c]pyridin-6-yl]-2-methylbenzenesulfonamide,
(207) 3-chloro-N-[7-({4-chloro-3-[(1-methylpiperidin-4-yl)methoxy]benzyl}oxy)-2,3-dihydrofuro[3,2-c]pyridin-6-yl]-2-methylbenzenesulfonamide,
(208) 3-chloro-N-[7-({4-chloro-3-[2-(dimethylamino)ethoxy]benzyl}oxy)-2,3-dihydrofuro[3,2-c]pyridin-6-yl]-2-methylbenzenesulfonamide,
(209) 3-chloro-2-methyl-N-{7-[(4-methyl-3,4-dihydro-2H-1,4-benzoxazin-6-yl)methoxy]-2,3-dihydrofuro[3,2-c]pyridin-6-yl}benzenesulfonamide,
(210) 3-chloro-2-methyl-N-{7-[(4-methyl-3,4-dihydro-2H-1,4-benzoxazin-7-yl)methoxy]-2,3-dihydrofuro[3,2-c]pyridin-6-yl}benzenesulfonamide,
(211) 3-chloro-2-methyl-N-[7-(2-phenoxyethoxy)-2,3-dihydrofuro[3,2-c]pyridin-6-yl]benzenesulfonamide,
(212) 3-chloro-2-methyl-N-[7-(pyridin-3-ylmethoxy)-3,4-dihydro-2H-pyrano[3,2-c]pyridin-8-yl]benzenesulfonamide,
(213) 3-chloro-N-{7-[(3,4-dimethoxybenzyl)oxy]-3,4-dihydro-2H-pyrano[3,2-c]pyridin-8-yl}-2-methylbenzenesulfonamide,
(214) 3-chloro-N-[7-({3-[2-(dimethylamino)ethoxy]-4-methoxybenzyl}oxy)-3,4-dihydro-2H-pyrano[3,2-c]pyridin-8-yl]-2-methylbenzenesulfonamide,
(215) 3-chloro-N-[7-({4-chloro-3-[(1-methylpiperidin-4-yl)methoxy]benzyl}oxy)-3,4-dihydro-2H-pyrano[3,2-c]pyridin-8-yl]-2-methylbenzenesulfonamide,
(216) 3-chloro-N-[7-({4-chloro-3-[2-(dimethylamino)ethoxy]benzyl}oxy)-3,4-dihydro-2H-pyrano[3,2-c]pyridin-8-yl]-2-methylbenzenesulfonamide,
(217) 3-chloro-2-methyl-N-{7-[(4-methyl-3,4-dihydro-2H-1,4-benzoxazin-6-yl)methoxy]-3,4-dihydro-2H-pyrano[3,2-c]pyridin-8-yl}benzenesulfonamide,
(218) 3-chloro-2-methyl-N-{7-[(4-methyl-3,4-dihydro-2H-1,4-benzoxazin-7-yl)methoxy]-3,4-dihydro-2H-pyrano[3,2-c]pyridin-8-yl}benzenesulfonamide,
(219) 3-chloro-2-methyl-N-[7-(2-phenoxyethoxy)-3,4-dihydro-2H-pyrano[3,2-c]pyridin-8-yl]benzenesulfonamide,
(220) 3-chloro-2-methyl-N-[8-(pyridin-3-ylmethoxy)-3,4-dihydro-2H-pyrano[3,2-c]pyridin-7-yl]benzenesulfonamide,
(221) 3-chloro-N-{8-[(3,4-dimethoxybenzyl)oxy]-3,4-dihydro-2H-pyrano[3,2-c]pyridin-7-yl}-2-methylbenzenesulfonamide,
(222) 3-chloro-N-[8-({3-[2-(dimethylamino)ethoxy]-4-methoxybenzyl}oxy)-3,4-dihydro-2H-pyrano[3,2-c]pyridin-7-yl]-2-methylbenzenesulfonamide,
(223) 3-chloro-N-[8-({4-chloro-3-[(1-methylpiperidin-4-yl)methoxy]benzyl}oxy)-3,4-dihydro-2H-pyrano[3,2-c]pyridin-7-yl]-2-methylbenzenesulfonamide,
(224) 3-chloro-N-[8-({4-chloro-3-[2-(dimethylamino)ethoxy]benzyl}oxy)-3,4-dihydro-2H-pyrano[3,2-c]pyridin-7-yl]-2-methylbenzenesulfonamide, (225) 3-chloro-2-methyl-N-{8-[(4-methyl-3,4-dihydro-2H-1,4-benzoxazin-6-yl)methoxy]-3,4-dihydro-2H-pyrano[3,2-c]pyridin-7-yl}benzenesulfonamide,
(226) 3-chloro-2-methyl-N-{8-[(4-methyl-3,4-dihydro-2H-1,4-benzoxazin-7-yl)methoxy]-3,4-dihydro-2H-pyrano[3,2-c]pyridin-7-yl}benzenesulfonamide,
(227) 3-chloro-2-methyl-N-[8-(2-phenoxyethoxy)-3,4-dihydro-2H-pyrano[3,2-c]pyridin-7-yl]benzenesulfonamide,
(228) 3-chloro-2-methyl-N-[2-(pyridin-3-ylmethoxy)thieno[2,3-b]pyrazin-3-yl]benzenesulfonamide,
(229) 3-chloro-N-{2-[(3,4-dimethoxybenzyl)oxy]thieno[2,3-b]pyrazin-3-yl}-2-methylbenzenesulfonamide,
(230) 3-chloro-N-[2-({3-[2-(dimethylamino)ethoxy]-4-methoxybenzyl}oxy)thieno[2,3-b]pyrazin-3-yl]-2-methylbenzenesulfonamide,
(231) 3-chloro-N-[2-({4-chloro-3-[(1-methylpiperidin-4-yl)methoxy]benzyl}oxy)thieno[2,3-b]pyrazin-3-yl]-2-methylbenzenesulfonamide,
(232) 3-chloro-N-[2-({4-chloro-3-[2-(dimethylamino)ethoxy]benzyl}oxy)thieno[2,3-b]pyrazin-3-yl]-2-methylbenzenesulfonamide,
(233) 3-chloro-2-methyl-N-{2-[(4-methyl-3,4-dihydro-2H-1,4-benzoxazin-6-yl)methoxy]thieno[2,3-b]pyrazin-3-yl}benzenesulfonamide,
(234) 3-chloro-2-methyl-N-{2-[(4-methyl-3,4-dihydro-2H-1,4-benzoxazin-7-yl)methoxy]thieno[2,3-b]pyrazin-3-yl}benzenesulfonamide,
(235) 3-chloro-2-methyl-N-[2-(2-phenoxyethoxy)thieno[2,3-b]pyrazin-3-yl]benzenesulfonamide,
(236) 3-chloro-2-methyl-N-[3-(pyridin-3-ylmethoxy)thieno[2,3-b]pyrazin-2-yl]benzenesulfonamide,
(237) 3-chloro-N-{3-[(3,4-dimethoxybenzyl)oxy]thieno[2,3-b]pyrazin-2-yl}-2-methylbenzenesulfonamide,
(238) 3-chloro-N-[3-({3-[2-(dimethylamino)ethoxy]-4-methoxybenzyl}oxy)thieno[2,3-b]pyrazin-2-yl]-2-methylbenzenesulfonamide,
(239) 3-chloro-N-[3-({4-chloro-3-[(1-methylpiperidin-4-yl)methoxy]benzyl}oxy)thieno[2,3-b]pyrazin-2-yl]-2-methylbenzenesulfonamide,
(240) 3-chloro-N-[3-({4-chloro-3-[2-(dimethylamino)ethoxy]benzyl}oxy)thieno[2,3-b]pyrazin-2-yl]-2-methylbenzenesulfonamide,
(241) 3-chloro-2-methyl-N-{3-[(4-methyl-3,4-dihydro-2H-1,4-benzoxazin-6-yl)methoxy]thieno[2,3-b]pyrazin-2-yl}benzenesulfonamide,
(242) 3-chloro-2-methyl-N-{3-[(4-methyl-3,4-dihydro-2H-1,4-benzoxazin-7-yl)methoxy]thieno[2,3-b]pyrazin-2-yl}benzenesulfonamide,
(243) 3-chloro-2-methyl-N-[3-(2-phenoxyethoxy)thieno[2,3-b]pyrazin-2-yl]benzenesulfonamide,
(244) 3-chloro-2-methyl-N-[5-(pyridin-3-ylmethoxy)[1,3]thiazolo[4,5-b]pyrazin-6-yl]benzenesulfonamide,
(245) 3-chloro-N-{5-[(3,4-dimethoxybenzyl)oxy][1,3]thiazolo[4,5-b]pyrazin-6-yl}-2-methylbenzenesulfonamide,
(246) 3-chloro-N-[5-({3-[2-(dimethylamino)ethoxy]-4-methoxybenzyl}oxy)[1,3]thiazolo[4,5-b]pyrazin-6-yl]-2-methylbenzenesulfonamide,
(247) 3-chloro-N-[5-({4-chloro-3-[(1-methylpiperidin-4-yl)methoxy]benzyl}oxy)[1,3]thiazolo[4,5-b]pyrazin-6-yl]-2-methylbenzenesulfonamide,
(248) 3-chloro-N-[5-({4-chloro-3-[2-(dimethylamino)ethoxy]benzyl}oxy)[1,3]thiazolo[4,5-b]pyrazin-6-yl]-2-methylbenzenesulfonamide,
(249) 3-chloro-2-methyl-N-{5-[(4-methyl-3,4-dihydro-2H-1,4-benzoxazin-6-yl)methoxy][1,3]thiazolo[4,5-b]pyrazin-6-yl}benzenesulfonamide,
(250) 3-chloro-2-methyl-N-{5-[(4-methyl-3,4-dihydro-2H-1,4-benzoxazin-7-yl)methoxy][1,3]thiazolo[4,5-b]pyrazin-6-yl}benzenesulfonamide,
(251) 3-chloro-2-methyl-N-[5-(2-phenoxyethoxy)[1,3]thiazolo[4,5-b]pyrazin-6-yl]benzenesulfonamide,
(252) 3-chloro-2-methyl-N-[6-(pyridin-3-ylmethoxy)[1,3]thiazolo[4,5-b]pyrazin-5-yl]benzenesulfonamide,
(253) 3-chloro-N-{6-[(3,4-dimethoxybenzyl)oxy][1,3]thiazolo[4,5-b]pyrazin-5-yl}-2-methylbenzenesulfonamide,
(254) 3-chloro-N-[6-({3-[2-(dimethylamino)ethoxy]-4-methoxybenzyl}oxy)[1,3]thiazolo[4,5-b]pyrazin-5-yl]-2-methylbenzenesulfonamide,
(255) 3-chloro-N-[6-({4-chloro-3-[(1-methylpiperidin-4-yl)methoxy]benzyl}oxy)[1,3]thiazolo[4,5-b]pyrazin-5-yl]-2-methylbenzenesulfonamide,
(256) 3-chloro-N-[6-({4-chloro-3-[2-(dimethylamino)ethoxy]benzyl}oxy)[1,3]thiazolo[4,5-b]pyrazin-5-yl]-2-methylbenzenesulfonamide,
(257) 3-chloro-2-methyl-N-{6-[(4-methyl-3,4-dihydro-2H-1,4-benzoxazin-6-yl)methoxy][1,3]thiazolo[4,5-b]pyrazin-5-yl}benzenesulfonamide,
(258) 3-chloro-2-methyl-N-{6-[(4-methyl-3,4-dihydro-2H-1,4-benzoxazin-7-yl)methoxy][1,3]thiazolo[4,5-b]pyrazin-5-yl}benzenesulfonamide,
(259) 3-chloro-2-methyl-N-[6-(2-phenoxyethoxy)[1,3]thiazolo[4,5-b]pyrazin-5-yl]benzenesulfonamide,
(260) 3-chloro-2-methyl-N-[4-methyl-6-(pyridin-3-ylmethoxy)-3,4-dihydro-2H-pyrazino[2,3-b][1,4]oxazin-7-yl]benzenesulfonamide,
(261) 3-chloro-N-{6-[(3,4-dimethoxybenzyl)oxy]-4-methyl-3,4-dihydro-2H-pyrazino[2,3-b][1,4]oxazin-7-yl}-2-methylbenzenesulfonamide,
(262) 3-chloro-N-[6-({3-[2-(dimethylamino)ethoxy]-4-methoxybenzyl}oxy)-4-methyl-3,4-dihydro-2H-pyrazino[2,3-b][1,4]oxazin-7-yl]-2-methylbenzenesulfonamide,
(263) 3-chloro-N-[6-({4-chloro-3-[(1-methylpiperidin-4-yl)methoxy]benzyl}oxy)-4-methyl-3,4-dihydro-2H-pyrazino[2,3-b][1,4]oxazin-7-yl]-2-methylbenzenesulfonamide,
(264) 3-chloro-N-[6-({4-chloro-3-[2-(dimethylamino)ethoxy]benzyl}oxy)-4-methyl-3,4-dihydro-2H-pyrazino[2,3-b][1,4]oxazin-7-yl]-2-methylbenzenesulfonamide,
(265) 3-chloro-2-methyl-N-{4-methyl-6-[(4-methyl-3,4-dihydro-2H-1,4-benzoxazin-6-yl)methoxy]-3,4-dihydro-2H-pyrazino[2,3-b][1,4]oxazin-7-yl}benzenesulfonamide,
(266) 3-chloro-2-methyl-N-{4-methyl-6-[(4-methyl-3,4-dihydro-2H-1,4-benzoxazin-7-yl)methoxy]-3,4-dihydro-2H-pyrazino[2,3-b][1,4]oxazin-7-yl}benzenesulfonamide,
(267) 3-chloro-2-methyl-N-[4-methyl-6-(2-phenoxyethoxy)-3,4-dihydro-2H-pyrazino[2,3-b][1,4]oxazin-7-yl]benzenesulfonamide,
(268) 3-chloro-2-methyl-N-[4-methyl-7-(pyridin-3-ylmethoxy)-3,4-dihydro-2H-pyrazino[2,3-b][1,4]oxazin-6-yl]benzenesulfonamide,
(269) 3-chloro-N-{7-[(3,4-dimethoxybenzyl)oxy]-4-methyl-3,4-dihydro-2H-pyrazino[2,3-b][1,4]oxazin-6-yl}-2-methylbenzenesulfonamide,
(270) 3-chloro-N-[7-({3-[2-(dimethylamino)ethoxy]-4-methoxybenzyl}oxy)-4-methyl-3,4-dihydro-2H-pyrazino[2,3-b][1,4]oxazin-6-yl]-2-methylbenzenesulfonamide,
(271) 3-chloro-N-[7-({4-chloro-3-[(1-methylpiperidin-4-yl)methoxy]benzyl}oxy)-4-methyl-3,4-dihydro-2H-pyrazino[2,3-b][1,4]oxazin-6-yl]-2-methylbenzenesulfonamide, (272) 3-chloro-N-[7-({4-chloro-3-[2-(dimethylamino)ethoxy]benzyl}oxy)-4-methyl-3,4-dihydro-2H-pyrazino[2,3-b][1,4]oxazin-6-yl]-2-methylbenzenesulfonamide,
(273) 3-chloro-2-methyl-N-{4-methyl-7-[(4-methyl-3,4-dihydro-2H-1,4-benzoxazin-6-yl)methoxy]-3,4-dihydro-2H-pyrazino[2,3-b][1,4]oxazin-6-yl}benzenesulfonamide,
(274) 3-chloro-2-methyl-N-{4-methyl-7-[(4-methyl-3,4-dihydro-2H-1,4-benzoxazin-7-yl)methoxy]-3,4-dihydro-2H-pyrazino[2,3-b][1,4]oxazin-6-yl}benzenesulfonamide,
(275) 3-chloro-2-methyl-N-[4-methyl-7-(2-phenoxyethoxy)-3,4-dihydro-2H-pyrazino[2,3-b][1,4]oxazin-6-yl]benzenesulfonamide,
(276) 3-chloro-2-methyl-N-[6-(pyridin-3-ylmethoxy)-2,3-dihydro-1H-pyrrolo[2,3-b]pyridin-5-yl]benzenesulfonamide,
(277) 3-chloro-N-{6-[(3,4-dimethoxybenzyl)oxy]-2,3-dihydro-1H-pyrrolo[2,3-b]pyridin-5-yl}-2-methylbenzenesulfonamide,
(278) 3-chloro-N-[6-({3-[2-(dimethylamino)ethoxy]-4-methoxybenzyl}oxy)-2,3-dihydro-1H-pyrrolo[2,3-b]pyridin-5-yl]-2-methylbenzenesulfonamide,
(279) 3-chloro-N-[6-({4-chloro-3-[(1-methylpiperidin-4-yl)methoxy]benzyl}oxy)-2,3-dihydro-1H-pyrrolo[2,3-b]pyridin-5-yl]-2-methylbenzenesulfonamide,
(280) 3-chloro-N-[6-({4-chloro-3-[2-(dimethylamino)ethoxy]benzyl}oxy)-2,3-dihydro-1H-pyrrolo[2,3-b]pyridin-5-yl]-2-methylbenzenesulfonamide,
(281) 3-chloro-2-methyl-N-{6-[(4-methyl-3,4-dihydro-2H-1,4-benzoxazin-6-yl)methoxy]-2,3-dihydro-1H-pyrrolo[2,3-b]pyridin-5-yl}benzenesulfonamide,
(282) 3-chloro-2-methyl-N-{6-[(4-methyl-3,4-dihydro-2H-1,4-benzoxazin-7-yl)methoxy]-2,3-dihydro-1H-pyrrolo[2,3-b]pyridin-5-yl}benzenesulfonamide,
(283) 3-chloro-2-methyl-N-[6-(2-phenoxyethoxy)-2,3-dihydro-1H-pyrrolo[2,3-b]pyridin-5-yl]benzenesulfonamide,
(284) 3-chloro-2-methyl-N-[5-(pyridin-3-ylmethoxy)-2,3-dihydro-1H-pyrrolo[2,3-b]pyridin-6-yl]benzenesulfonamide,
(285) 3-chloro-N-{5-[(3,4-dimethoxybenzyl)oxy]-2,3-dihydro-1H-pyrrolo[2,3-b]pyridin-6-yl}-2-methylbenzenesulfonamide,
(286) 3-chloro-N-[5-({3-[2-(dimethylamino)ethoxy]-4-methoxybenzyl}oxy)-2,3-dihydro-1H-pyrrolo[2,3-b]pyridin-6-yl]-2-methylbenzenesulfonamide,
(287) 3-chloro-N-[5-({4-chloro-3-[(1-methylpiperidin-4-yl)methoxy]benzyl}oxy)-2,3-dihydro-1H-pyrrolo[2,3-b]pyridin-6-yl]-2-methylbenzenesulfonamide,
(288) 3-chloro-N-[5-({4-chloro-3-[2-(dimethylamino)ethoxy]benzyl}oxy)-2,3-dihydro-1H-pyrrolo[2,3-b]pyridin-6-yl]-2-methylbenzenesulfonamide,
(289) 3-chloro-2-methyl-N-{5-[(4-methyl-3,4-dihydro-2H-1,4-benzoxazin-6-yl)methoxy]-2,3-dihydro-1H-pyrrolo[2,3-b]pyridin-6-yl}benzenesulfonamide,
(290) 3-chloro-2-methyl-N-{5-[(4-methyl-3,4-dihydro-2H-1,4-benzoxazin-7-yl)methoxy]-2,3-dihydro-1H-pyrrolo[2,3-b]pyridin-6-yl}benzenesulfonamide,
(291) 3-chloro-2-methyl-N-[5-(2-phenoxyethoxy)-2,3-dihydro-1H-pyrrolo[2,3-b]pyridin-6-yl]benzenesulfonamide,
(292) 3-chloro-2-methyl-N-[6-(pyridin-3-ylmethoxy)imidazo[1,2-a]pyrazin-5-yl]benzenesulfonamide,
(293) 3-chloro-N-{6-[(3,4-dimethoxybenzyl)oxy]imidazo[1,2-a]pyrazin-5-yl}-2-methylbenzenesulfonamide,
(294) 3-chloro-N-[6-({3-[2-(dimethylamino)ethoxy]-4-methoxybenzyl}oxy)imidazo[1,2-a]pyrazin-5-yl]-2-methylbenzenesulfonamide,
(295) 3-chloro-N-[6-({4-chloro-3-[(1-methylpiperidin-4-yl)methoxy]benzyl}oxy)imidazo[1,2-a]pyrazin-5-yl]-2-methylbenzenesulfonamide,
(296) 3-chloro-N-[6-({4-chloro-3-[2-(dimethylamino)ethoxy]benzyl}oxy)imidazo[1,2-a]pyrazin-5-yl]-2-methylbenzenesulfonamide,
(297) 3-chloro-2-methyl-N-{6-[(4-methyl-3,4-dihydro-2H-1,4-benzoxazin-6-yl)methoxy]imidazo[1,2-a]pyrazin-5-yl}benzenesulfonamide,
(298) 3-chloro-2-methyl-N-{6-[(4-methyl-3,4-dihydro-2H-1,4-benzoxazin-7-yl)methoxy]imidazo[1,2-a]pyrazin-5-yl}benzenesulfonamide,
(299) 3-chloro-2-methyl-N-[6-(2-phenoxyethoxy)imidazo[1,2-a]pyrazin-5-yl]benzenesulfonamide,
(300) 3-chloro-2-methyl-N-[5-(pyridin-3-ylmethoxy)imidazo[1,2-a]pyrazin-6-yl]benzenesulfonamide,
(301) 3-chloro-N-{5-[(3,4-dimethoxybenzyl)oxy]imidazo[1,2-a]pyrazin-6-yl}-2-methylbenzenesulfonamide,
(302) 3-chloro-N-[5-({3-[2-(dimethylamino)ethoxy]-4-methoxybenzyl}oxy)imidazo[1,2-a]pyrazin-6-yl]-2-methylbenzenesulfonamide,
(303) 3-chloro-N-[5-({4-chloro-3-[(1-methylpiperidin-4-yl)methoxy]benzyl}oxy)imidazo[1,2-a]pyrazin-6-yl]-2-methylbenzenesulfonamide,
(304) 3-chloro-N-[5-({4-chloro-3-[2-(dimethylamino)ethoxy]benzyl}oxy)imidazo[1,2-a]pyrazin-6-yl]-2-methylbenzenesulfonamide,
(305) 3-chloro-2-methyl-N-{5-[(4-methyl-3,4-dihydro-2H-1,4-benzoxazin-6-yl)methoxy]imidazo[1,2-a]pyrazin-6-yl}benzenesulfonamide,
(306) 3-chloro-2-methyl-N-{5-[(4-methyl-3,4-dihydro-2H-1,4-benzoxazin-7-yl)methoxy]imidazo[1,2-a]pyrazin-6-yl}benzenesulfonamide,
(307) 3-chloro-2-methyl-N-[5-(2-phenoxyethoxy)imidazo[1,2-a]pyrazin-6-yl]benzenesulfonamide,
(308) 3-chloro-2-methyl-N-[2-(pyridin-3-ylmethoxy)imidazo[1,2-a]pyrazin-3-yl]benzenesulfonamide,
(309) 3-chloro-N-{2-[(3,4-dimethoxybenzyl)oxy]imidazo[1,2-a]pyrazin-3-yl}-2-methylbenzenesulfonamide,
(310) 3-chloro-N-[2-({3-[2-(dimethylamino)ethoxy]-4-methoxybenzyl}oxy)imidazo[1,2-a]pyrazin-3-yl]-2-methylbenzenesulfonamide,
(311) 3-chloro-N-[2-({4-chloro-3-[(1-methylpiperidin-4-yl)methoxy]benzyl}oxy)imidazo[1,2-a]pyrazin-3-yl]-2-methylbenzenesulfonamide,
(312) 3-chloro-N-[2-({4-chloro-3-[2-(dimethylamino)ethoxy]benzyl}oxy)imidazo[1,2-a]pyrazin-3-yl]-2-methylbenzenesulfonamide,
(313) 3-chloro-2-methyl-N-{2-[(4-methyl-3,4-dihydro-2H-1,4-benzoxazin-6-yl)methoxy]imidazo[1,2-a]pyrazin-3-yl}benzenesulfonamide,
(314) 3-chloro-2-methyl-N-{2-[(4-methyl-3,4-dihydro-2H-1,4-benzoxazin-7-yl)methoxy]imidazo[1,2-a]pyrazin-3-yl}benzenesulfonamide,
(315) 3-chloro-2-methyl-N-[2-(2-phenoxyethoxy)imidazo[1,2-a]pyrazin-3-yl]benzenesulfonamide,
(316) 3-chloro-2-methyl-N-[3-(pyridin-3-ylmethoxy)imidazo[1,2-a]pyrazin-2-yl]benzenesulfonamide,
(317) 3-chloro-N-{3-[(3,4-dimethoxybenzyl)oxy]imidazo[1,2-a]pyrazin-2-yl}-2-methylbenzenesulfonamide,
(318) 3-chloro-N-[3-({3-[2-(dimethylamino)ethoxy]-4-methoxybenzyl}oxy)imidazo[1,2-a]pyrazin-2-yl]-2-methylbenzenesulfonamide,
(319) 3-chloro-N-[3-({4-chloro-3-[(1-methylpiperidin-4-yl)methoxy]benzyl}oxy)imidazo[1,2-a]pyrazin-2-yl]-2-methylbenzenesulfonamide, (320) 3-chloro-N-[3-({4-chloro-3-[2-(dimethylamino)ethoxy]benzyl}oxy)imidazo[1,2-a]pyrazin-2-yl]-2-methylbenzenesulfonamide,
(321) 3-chloro-2-methyl-N-{3-[(4-methyl-3,4-dihydro-2H-1,4-benzoxazin-6-yl)methoxy]imidazo[1,2-a]pyrazin-2-yl}benzenesulfonamide,
(322) 3-chloro-2-methyl-N-{3-[(4-methyl-3,4-dihydro-2H-1,4-benzoxazin-7-yl)methoxy]imidazo[1,2-a]pyrazin-2-yl}benzenesulfonamide,
(323) 3-chloro-2-methyl-N-[3-(2-phenoxyethoxy)imidazo[1,2-a]pyrazin-2-yl]benzenesulfonamide,
(324) 3-chloro-2-methyl-N-[2-(pyridin-3-ylmethoxy)-1,5-naphthyridine3-yl]benzenesulfonamide,
(325) 3-chloro-N-{2-[(3,4-dimethoxybenzyl)oxy]-1,5-naphthyridine3-yl}-2-methylbenzenesulfonamide,
(326) 3-chloro-N-[2-({3-[2-(dimethylamino)ethoxy]-4-methoxybenzyl}oxy)-1,5-naphthyridine3-yl]-2-methylbenzenesulfonamide,
(327) 3-chloro-N-[2-({4-chloro-3-[(1-methylpiperidin-4-yl)methoxy]benzyl}oxy)-1,5-naphthyridine3-yl]-2-methylbenzenesulfonamide,
(328) 3-chloro-N-[2-({4-chloro-3-[2-(dimethylamino)ethoxy]benzyl}oxy)-1,5-naphthyridine3-yl]-2-methylbenzenesulfonamide,
(329) 3-chloro-2-methyl-N-{2-[(4-methyl-3,4-dihydro-2H-1,4-benzoxazin-6-yl)methoxy]-1,5-naphthyridine3-yl}benzenesulfonamide,
(330) 3-chloro-2-methyl-N-{2-[(4-methyl-3,4-dihydro-2H-1,4-benzoxazin-7-yl)methoxy]-1,5-naphthyridine3-yl}benzenesulfonamide,
(331) 3-chloro-2-methyl-N-[2-(2-phenoxyethoxy)-1,5-naphthyridine3-yl]benzenesulfonamide,
(332) 3-chloro-2-methyl-N-[3-(pyridin-3-ylmethoxy)-1,5-naphthyridine2-yl]benzenesulfonamide,
(333) 3-chloro-N-{3-[(3,4-dimethoxybenzyl)oxy]-1,5-naphthyridine2-yl}-2-methylbenzenesulfonamide,
(334) 3-chloro-N-[3-({3-[2-(dimethylamino)ethoxy]-4-methoxybenzyl}oxy)-1,5-naphthyridine2-yl]-2-methylbenzenesulfonamide,
(335) 3-chloro-N-[3-({4-chloro-3-[(1-methylpiperidin-4-yl)methoxy]benzyl}oxy)-1,5-naphthyridine2-yl]-2-methylbenzenesulfonamide,
(336) 3-chloro-N-[3-({4-chloro-3-[2-(dimethylamino)ethoxy]benzyl}oxy)-1,5-naphthyridine2-yl]-2-methylbenzenesulfonamide,
(337) 3-chloro-2-methyl-N-{3-[(4-methyl-3,4-dihydro-2H-1,4-benzoxazin-6-yl)methoxy]-1,5-naphthyridine2-yl}benzenesulfonamide,
(338) 3-chloro-2-methyl-N-{3-[(4-methyl-3,4-dihydro-2H-1,4-benzoxazin-7-yl)methoxy]-1,5-naphthyridine2-yl}benzenesulfonamide,
(339) 3-chloro-2-methyl-N-[3-(2-phenoxyethoxy)-1,5-naphthyridine2-yl]benzenesulfonamide,
(340) 3-chloro-2-methyl-N-[2-(pyridin-3-ylmethoxy)pyrido[3,4-b]pyrazin-3-yl]benzenesulfonamide,
(341) 3-chloro-N-{2-[(3,4-dimethoxybenzyl)oxy]pyrido[3,4-b]pyrazin-3-yl}-2-methylbenzenesulfonamide,
(342) 3-chloro-N-[2-({3-[2-(dimethylamino)ethoxy]-4-methoxybenzyl}oxy)pyrido[3,4-b]pyrazin-3-yl]-2-methylbenzenesulfonamide,
(343) 3-chloro-N-[2-({4-chloro-3-[(1-methylpiperidin-4-yl)methoxy]benzyl}oxy)pyrido[3,4-b]pyrazin-3-yl]-2-methylbenzenesulfonamide,
(344) 3-chloro-N-[2-({4-chloro-3-[2-(dimethylamino)ethoxy]benzyl}oxy)pyrido[3,4-b]pyrazin-3-yl]-2-methylbenzenesulfonamide,
(345) 3-chloro-2-methyl-N-{2-[(4-methyl-3,4-dihydro-2H-1,4-benzoxazin-6-yl)methoxy]pyrido[3,4-b]pyrazin-3-yl}benzenesulfonamide,
(346) 3-chloro-2-methyl-N-{2-[(4-methyl-3,4-dihydro-2H-1,4-benzoxazin-7-yl)methoxy]pyrido[3,4-b]pyrazin-3-yl}benzenesulfonamide,
(347) 3-chloro-2-methyl-N-[2-(2-phenoxyethoxy)pyrido[3,4-b]pyrazin-3-yl]benzenesulfonamide,
(348) 3-chloro-2-methyl-N-[3-(pyridin-3-ylmethoxy)pyrido[3,4-b]pyrazin-2-yl]benzenesulfonamide,
(349) 3-chloro-N-{3-[(3,4-dimethoxybenzyl)oxy]pyrido[3,4-b]pyrazin-2-yl}-2-methylbenzenesulfonamide,
(350) 3-chloro-N-[3-({3-[2-(dimethylamino)ethoxy]-4-methoxybenzyl}oxy)pyrido[3,4-b]pyrazin-2-yl]-2-methylbenzenesulfonamide,
(351) 3-chloro-N-[3-({4-chloro-3-[(1-methylpiperidin-4-yl)methoxy]benzyl}oxy)pyrido[3,4-b]pyrazin-2-yl]-2-methylbenzenesulfonamide,
(352) 3-chloro-N-[3-({4-chloro-3-[2-(dimethylamino)ethoxy]benzyl}oxy)pyrido[3,4-b]pyrazin-2-yl]-2-methylbenzenesulfonamide,
(353) 3-chloro-2-methyl-N-{3-[(4-methyl-3,4-dihydro-2H-1,4-benzoxazin-6-yl)methoxy]pyrido[3,4-b]pyrazin-2-yl}benzenesulfonamide,
(354) 3-chloro-2-methyl-N-{3-[(4-methyl-3,4-dihydro-2H-1,4-benzoxazin-7-yl)methoxy]pyrido[3,4-b]pyrazin-2-yl}benzenesulfonamide,
(355) 3-chloro-2-methyl-N-[3-(2-phenoxyethoxy)pyrido[3,4-b]pyrazin-2-yl]benzenesulfonamide,
(356) 3-chloro-2-methyl-N-[2-(pyridin-3-ylmethoxy)pyrido[2,3-b]pyrazin-3-yl]benzenesulfonamide,
(357) 3-chloro-N-{2-[(3,4-dimethoxybenzyl)oxy]pyrido[2,3-b]pyrazin-3-yl}-2-methylbenzenesulfonamide,
(358) 3-chloro-N-[2-({3-[2-(dimethylamino)ethoxy]-4-methoxybenzyl}oxy)pyrido[2,3-b]pyrazin-3-yl]-2-methylbenzenesulfonamide,
(359) 3-chloro-N-[2-({4-chloro-3-[(1-methylpiperidin-4-yl)methoxy]benzyl}oxy)pyrido[2,3-b]pyrazin-3-yl]-2-methylbenzenesulfonamide,
(360) 3-chloro-N-[2-({4-chloro-3-[2-(dimethylamino)ethoxy]benzyl}oxy)pyrido[2,3-b]pyrazin-3-yl]-2-methylbenzenesulfonamide,
(361) 3-chloro-2-methyl-N-{2-[(4-methyl-3,4-dihydro-2H-1,4-benzoxazin-6-yl)methoxy]pyrido[2,3-b]pyrazin-3-yl}benzenesulfonamide,
(362) 3-chloro-2-methyl-N-{2-[(4-methyl-3,4-dihydro-2H-1,4-benzoxazin-7-yl)methoxy]pyrido[2,3-b]pyrazin-3-yl}benzenesulfonamide,
(363) 3-chloro-2-methyl-N-[2-(2-phenoxyethoxy)pyrido[2,3-b]pyrazin-3-yl]benzenesulfonamide,
(364) 3-chloro-2-methyl-N-[3-(pyridin-3-ylmethoxy)quinoxalin-2-yl]benzenesulfonamide,
(365) 3-chloro-N-{3-[(3,4-dimethoxybenzyl)oxy]quinoxalin-2-yl}-2-methylbenzenesulfonamide,
(366) 3-chloro-N-[3-({3-[2-(dimethylamino)ethoxy]-4-methoxybenzyl}oxy)quinoxalin-2-yl]-2-methylbenzenesulfonamide,
(367) 3-chloro-N-[3-({4-chloro-3-[(1-methylpiperidin-4-yl)methoxy]benzyl}oxy)quinoxalin-2-yl]-2-methylbenzenesulfonamide,
(368) 3-chloro-N-[3-({4-chloro-3-[2-(dimethylamino)ethoxy]benzyl}oxy)quinoxalin-2-yl]-2-methylbenzenesulfonamide,
(369) 3-chloro-2-methyl-N-{3-[(4-methyl-3,4-dihydro-2H-1,4-benzoxazin-6-yl)methoxy]quinoxalin-2-yl}benzenesulfonamide, (370) 3-chloro-2-methyl-N-{3-[(4-methyl-3,4-dihydro-2H-1,4-benzoxazin-7-yl)methoxy]quinoxalin-2-yl}benzenesulfonamide,
(371) 3-chloro-2-methyl-N-[3-(2-phenoxyethoxy)quinoxalin-2-yl]benzenesulfonamide,
(372) 3-chloro-2-methyl-N-[3-(pyridin-3-ylmethoxy)pyrido[2,3-b]pyrazin-2-yl]benzenesulfonamide,
(373) 3-chloro-N-{3-[(3,4-dimethoxybenzyl)oxy]pyrido[2,3-b]pyrazin-2-yl}-2-methylbenzenesulfonamide,
(374) 3-chloro-N-[3-({3-[2-(dimethylamino)ethoxy]-4-methoxybenzyl}oxy)pyrido[2,3-b]pyrazin-2-yl]-2-methylbenzenesulfonamide,
(375) 3-chloro-N-[3-({4-chloro-3-[(1-methylpiperidin-4-yl)methoxy]benzyl}oxy)pyrido[2,3-b]pyrazin-2-yl]-2-methylbenzenesulfonamide,
(376) 3-chloro-N-[3-({4-chloro-3-[2-(dimethylamino)ethoxy]benzyl}oxy)pyrido[2,3-b]pyrazin-2-yl]-2-methylbenzenesulfonamide,
(377) 3-chloro-2-methyl-N-{3-[(4-methyl-3,4-dihydro-2H-1,4-benzoxazin-6-yl)methoxy]pyrido[2,3-b]pyrazin-2-yl}benzenesulfonamide,
(378) 3-chloro-2-methyl-N-{3-[(4-methyl-3,4-dihydro-2H-1,4-benzoxazin-7-yl)methoxy]pyrido[2,3-b]pyrazin-2-yl}benzenesulfonamide,
(379) 3-chloro-2-methyl-N-[3-(2-phenoxyethoxy)pyrido[2,3-b]pyrazin-2-yl]benzenesulfonamide,
(380) 3-chloro-2-methyl-N-[3-(pyridin-3-ylmethoxy)-6,7-dihydro-5H-cyclopent[b]pyrazin-2-yl]benzenesulfonamide,
(381) 3-chloro-N-{3-[(3,4-dimethoxybenzyl)oxy]-6,7-dihydro-5H-cyclopent[b]pyrazin-2-yl}-2-methylbenzenesulfonamide,
(382) 3-chloro-N-[3-({3-[2-(dimethylamino)ethoxy]-4-methoxybenzyl}oxy)-6,7-dihydro-5H-cyclopent[b]pyrazin-2-yl]-2-methylbenzenesulfonamide,
(383) 3-chloro-N-[3-({4-chloro-3-[(1-methylpiperidin-4-yl)methoxy]benzyl}oxy)-6,7-dihydro-5H-cyclopent[b]pyrazin-2-yl]-2-methylbenzenesulfonamide,
(384) 3-chloro-N-[3-({4-chloro-3-[2-(dimethylamino)ethoxy]benzyl}oxy)-6,7-dihydro-5H-cyclopent[b]pyrazin-2-yl]-2-methylbenzenesulfonamide,
(385) 3-chloro-2-methyl-N-{3-[(4-methyl-3,4-dihydro-2H-1,4-benzoxazin-6-yl)methoxy]-6,7-dihydro-5H-cyclopent[b]pyrazin-2-yl}benzenesulfonamide,
(386) 3-chloro-2-methyl-N-{3-[(4-methyl-3,4-dihydro-2H-1,4-benzoxazin-7-yl)methoxy]-6,7-dihydro-5H-cyclopent[b]pyrazin-2-yl}benzenesulfonamide,
(387) 3-chloro-2-methyl-N-[3-(2-phenoxyethoxy)-6,7-dihydro-5H-cyclopent[b]pyrazin-2-yl]benzenesulfonamide,
(388) 3-chloro-2-methyl-N-[3-(pyridin-3-ylmethoxy)-5,6,7,8-tetrahydroquinoxalin-2-yl]benzenesulfonamide,
(389) 3-chloro-N-{3-[(3,4-dimethoxybenzyl)oxy]-5,6,7,8-tetrahydroquinoxalin-2-yl}-2-methylbenzenesulfonamide,
(390) 3-chloro-N-[3-({3-[2-(dimethylamino)ethoxy]-4-methoxybenzyl}oxy)-5,6,7,8-tetrahydroquinoxalin-2-yl]-2-methylbenzenesulfonamide,
(391) 3-chloro-N-[3-({4-chloro-3-[(1-methylpiperidin-4-yl)methoxy]benzyl}oxy)-5,6,7,8-tetrahydroquinoxalin-2-yl]-2-methylbenzenesulfonamide,
(392) 3-chloro-N-[3-({4-chloro-3-[2-(dimethylamino)ethoxy]benzyl}oxy)-5,6,7,8-tetrahydroquinoxalin-2-yl]-2-methylbenzenesulfonamide,
(393) 3-chloro-2-methyl-N-{3-[(4-methyl-3,4-dihydro-2H-1,4-benzoxazin-6-yl)methoxy]-5,6,7,8-tetrahydroquinoxalin-2-yl}benzenesulfonamide,
(394) 3-chloro-2-methyl-N-{3-[(4-methyl-3,4-dihydro-2H-1,4-benzoxazin-7-yl)methoxy]-5,6,7,8-tetrahydroquinoxalin-2-yl}benzenesulfonamide,
(395) 3-chloro-2-methyl-N-[3-(2-phenoxyethoxy)-5,6,7,8-tetrahydroquinoxalin-2-yl]benzenesulfonamide,
(396) 3-chloro-2-methyl-N-[5-(pyridin-3-ylmethoxy)pyrimidin-4-yl]benzenesulfonamide,
(397) 3-chloro-N-{5-[(3,4-dimethoxybenzyl)oxy]pyrimidin-4-yl}-2-methylbenzenesulfonamide,
(398) 3-chloro-N-[5-({3-[2-(dimethylamino)ethoxy]-4-methoxybenzyl}oxy)pyrimidin-4-yl]-2-methylbenzenesulfonamide,
(399) 3-chloro-N-[5-({4-chloro-3-[(1-methylpiperidin-4-yl)methoxy]benzyl}oxy)pyrimidin-4-yl]-2-methylbenzenesulfonamide,
(400) 3-chloro-N-[5-({4-chloro-3-[2-(dimethylamino)ethoxy]benzyl}oxy)pyrimidin-4-yl]-2-methylbenzenesulfonamide,
(401) 3-chloro-2-methyl-N-{5-[(4-methyl-3,4-dihydro-2H-1,4-benzoxazin-6-yl)methoxy]pyrimidin-4-yl}benzenesulfonamide,
(402) 3-chloro-2-methyl-N-{5-[(4-methyl-3,4-dihydro-2H-1,4-benzoxazin-7-yl)methoxy]pyrimidin-4-yl}benzenesulfonamide,
(403) 3-chloro-2-methyl-N-[5-(2-phenoxyethoxy)pyrimidin-4-yl]benzenesulfonamide,
(404) 3-chloro-2-methyl-N-[4-(pyridin-3-ylmethoxy)pyrimidin-5-yl]benzenesulfonamide,
(405) 3-chloro-N-{4-[(3,4-dimethoxybenzyl)oxy]pyrimidin-5-yl}-2-methylbenzenesulfonamide,
(406) 3-chloro-N-[4-({3-[2-(dimethylamino)ethoxy]-4-methoxybenzyl}oxy)pyrimidin-5-yl]-2-methylbenzenesulfonamide,
(407) 3-chloro-N-[4-({4-chloro-3-[(1-methylpiperidin-4-yl)methoxy]benzyl}oxy)pyrimidin-5-yl]-2-methylbenzenesulfonamide,
(408) 3-chloro-N-[4-({4-chloro-3-[2-(dimethylamino)ethoxy]benzyl}oxy)pyrimidin-5-yl]-2-methylbenzenesulfonamide,
(409) 3-chloro-2-methyl-N-{4-[(4-methyl-3,4-dihydro-2H-1,4-benzoxazin-6-yl)methoxy]pyrimidin-5-yl}benzenesulfonamide,
(410) 3-chloro-2-methyl-N-{4-[(4-methyl-3,4-dihydro-2H-1,4-benzoxazin-7-yl)methoxy]pyrimidin-5-yl}benzenesulfonamide,
(411) 3-chloro-2-methyl-N-[4-(2-phenoxyethoxy)pyrimidin-5-yl]benzenesulfonamide,
(412) 3-chloro-2-methyl-N-[3-(pyridin-3-ylmethoxy)pyridin-2-yl]benzenesulfonamide,
(413) 3-chloro-N-{3-[(3,4-dimethoxybenzyl)oxy]pyridin-2-yl}-2-methylbenzenesulfonamide,
(414) 3-chloro-N-[3-({3-[2-(dimethylamino)ethoxy]-4-methoxybenzyl}oxy)pyridin-2-yl]-2-methylbenzenesulfonamide,
(415) 3-chloro-N-[3-({4-chloro-3-[(1-methylpiperidin-4-yl)methoxy]benzyl}oxy)pyridin-2-yl]-2-methylbenzenesulfonamide,
(416) 3-chloro-N-[3-({4-chloro-3-[2-(dimethylamino)ethoxy]benzyl}oxy)pyridin-2-yl]-2-methylbenzenesulfonamide,
(417) 3-chloro-2-methyl-N-{3-[(4-methyl-3,4-dihydro-2H-1,4-benzoxazin-6-yl)methoxy]pyridin-2-yl}benzenesulfonamide,
(418) 3-chloro-2-methyl-N-{3-[(4-methyl-3,4-dihydro-2H-1,4-benzoxazin-7-yl)methoxy]pyridin-2-yl}benzenesulfonamide, (419) 3-chloro-2-methyl-N-[3-(2-phenoxyethoxy)pyridin-2-yl]benzenesulfonamide,
(420) 3-chloro-2-methyl-N-[4-(pyridin-3-ylmethoxy)pyridin-3-yl]benzenesulfonamide,
(421) 3-chloro-N-{4-[(3,4-dimethoxybenzyl)oxy]pyridin-3-yl}-2-methylbenzenesulfonamide,
(422) 3-chloro-N-[4-({3-[2-(dimethylamino)ethoxy]-4-methoxybenzyl}oxy)pyridin-3-yl]-2-methylbenzenesulfonamide,
(423) 3-chloro-N-[4-({4-chloro-3-[(1-methylpiperidin-4-yl)methoxy]benzyl}oxy)pyridin-3-yl]-2-methylbenzenesulfonamide,
(424) 3-chloro-N-[4-({4-chloro-3-[2-(dimethylamino)ethoxy]benzyl}oxy)pyridin-3-yl]-2-methylbenzenesulfonamide,
(425) 3-chloro-2-methyl-N-{4-[(4-methyl-3,4-dihydro-2H-1,4-benzoxazin-6-yl)methoxy]pyridin-3-yl}benzenesulfonamide,
(426) 3-chloro-2-methyl-N-{4-[(4-methyl-3,4-dihydro-2H-1,4-benzoxazin-7-yl)methoxy]pyridin-3-yl}benzenesulfonamide,
(427) 3-chloro-2-methyl-N-[4-(2-phenoxyethoxy)pyridin-3-yl]benzenesulfonamide,
(428) 3-chloro-2-methyl-N-[3-(pyridin-3-ylmethoxy)pyridin-4-yl]benzenesulfonamide,
(429) 3-chloro-N-{3-[(3,4-dimethoxybenzyl)oxy]pyridin-4-yl}-2-methylbenzenesulfonamide,
(430) 3-chloro-N-[3-({3-[2-(dimethylamino)ethoxy]-4-methoxybenzyl}oxy)pyridin-4-yl]-2-methylbenzenesulfonamide,
(431) 3-chloro-N-[3-({4-chloro-3-[(1-methylpiperidin-4-yl)methoxy]benzyl}oxy)pyridin-4-yl]-2-methylbenzenesulfonamide,
(432) 3-chloro-N-[3-({4-chloro-3-[2-(dimethylamino)ethoxy]benzyl}oxy)pyridin-4-yl]-2-methylbenzenesulfonamide,
(433) 3-chloro-2-methyl-N-{3-[(4-methyl-3,4-dihydro-2H-1,4-benzoxazin-6-yl)methoxy]pyridin-4-yl}benzenesulfonamide,
(434) 3-chloro-2-methyl-N-{3-[(4-methyl-3,4-dihydro-2H-1,4-benzoxazin-7-yl)methoxy]pyridin-4-yl}benzenesulfonamide,
(435) 3-chloro-2-methyl-N-[3-(2-phenoxyethoxy)pyridin-4-yl]benzenesulfonamide,
(436) 3-chloro-2-methyl-N-[2-(pyridin-3-ylmethoxy)pyridin-3-yl]benzenesulfonamide,
(437) 3-chloro-N-{2-[(3,4-dimethoxybenzyl)oxy]pyridin-3-yl}-2-methylbenzenesulfonamide,
(438) 3-chloro-N-[2-({3-[2-(dimethylamino)ethoxy]-4-methoxybenzyl}oxy)pyridin-3-yl]-2-methylbenzenesulfonamide,
(439) 3-chloro-N-[2-({4-chloro-3-[(1-methylpiperidin-4-yl)methoxy]benzyl}oxy)pyridin-3-yl]-2-methylbenzenesulfonamide,
(440) 3-chloro-N-[2-({4-chloro-3-[2-(dimethylamino)ethoxy]benzyl}oxy)pyridin-3-yl]-2-methylbenzenesulfonamide,
(441) 3-chloro-2-methyl-N-{2-[(4-methyl-3,4-dihydro-2H-1,4-benzoxazin-6-yl)methoxy]pyridin-3-yl}benzenesulfonamide,
(442) 3-chloro-2-methyl-N-{2-[(4-methyl-3,4-dihydro-2H-1,4-benzoxazin-7-yl)methoxy]pyridin-3-yl}benzenesulfonamide,
(443) 3-chloro-2-methyl-N-[2-(2-phenoxyethoxy)pyridin-3-yl]benzenesulfonamide,
(444) N-[3-({4-chloro-3-[(1-methylpiperidin-4-yl)methoxy]benzyl}oxy)-5-methylpyrazin-2-yl]-4-methylbenzenesulfonamide,
(445) 2,3-dichloro-N-[3-({4-chloro-3-[(1-methylpiperidin-4-yl)methoxy]benzyl}oxy)-5-methylpyrazin-2-yl]benzenesulfonamide,
(446) 2-chloro-N-[3-({4-chloro-3-[(1-methylpiperidin-4-yl)methoxy]benzyl}oxy)-5-methylpyrazin-2-yl]benzenesulfonamide,
(447) N-[3-({4-chloro-3-[(1-methylpiperidin-4-yl)methoxy]benzyl}oxy)-5-methylpyrazin-2-yl]-2-(trifluoromethyl)benzenesulfonamide,
(448) 4-methyl-N-{5-methyl-3-[(4-methyl-3,4-dihydro-2H-1,4-benzoxazin-7-yl)methoxy]pyrazin-2-yl}benzenesulfonamide,
(449) 2,3-dichloro-N-{5-methyl-3-[(4-methyl-3,4-dihydro-2H-1,4-benzoxazin-7-yl)methoxy]pyrazin-2-yl}benzenesulfonamide,
(450) 2-chloro-N-{5-methyl-3-[(4-methyl-3,4-dihydro-2H-1,4-benzoxazin-7-yl)methoxy]pyrazin-2-yl}benzenesulfonamide,
(451) N-{5-methyl-3-[(4-methyl-3,4-dihydro-2H-1,4-benzoxazin-7-yl)methoxy]pyrazin-2-yl}-2-(trifluoromethyl)benzenesulfonamide,
(452) N-[2-({4-chloro-3-[(1-methylpiperidin-4-yl)methoxy]benzyl}oxy)quinolin-3-yl]-4-methylbenzenesulfonamide,
(453) 2,3-dichloro-N-[2-({4-chloro-3-[(1-methylpiperidin-4-yl)methoxy]benzyl}oxy)quinolin-3-yl]benzenesulfonamide,
(454) 2-chloro-N-[2-({4-chloro-3-[(1-methylpiperidin-4-yl)methoxy]benzyl}oxy)quinolin-3-yl]benzenesulfonamide,
(455) N-[2-({4-chloro-3-[(1-methylpiperidin-4-yl)methoxy]benzyl}oxy)quinolin-3-yl]-2-(trifluoromethyl)benzenesulfonamide,
(456) N-[2-({4-chloro-3-[2-(dimethylamino)ethoxy]benzyl}oxy)quinolin-3-yl]-4-methylbenzenesulfonamide,
(457) 2,3-dichloro-N-[2-({4-chloro-3-[2-(dimethylamino)ethoxy]benzyl}oxy)quinolin-3-yl]benzenesulfonamide,
(458) 2-chloro-N-[2-({4-chloro-3-[2-(dimethylamino)ethoxy]benzyl}oxy)quinolin-3-yl]benzenesulfonamide,
(459) N-[2-({4-chloro-3-[2-(dimethylamino)ethoxy]benzyl}oxy)quinolin-3-yl]-2-(trifluoromethyl)benzenesulfonamide,
(460) 4-methyl-N-{2-[(4-methyl-3,4-dihydro-2H-1,4-benzoxazin-7-yl)methoxy]quinolin-3-yl}benzenesulfonamide,
(461) 2,3-dichloro-N-{2-[(4-methyl-3,4-dihydro-2H-1,4-benzoxazin-7-yl)methoxy]quinolin-3-yl}benzenesulfonamide,
(462) 2-chloro-N-{2-[(4-methyl-3,4-dihydro-2H-1,4-benzoxazin-7-yl)methoxy]quinolin-3-yl}benzenesulfonamide,
(463) N-{2-[(4-methyl-3,4-dihydro-2H-1,4-benzoxazin-7-yl)methoxy]quinolin-3-yl}-2-(trifluoromethyl)benzenesulfonamide,
(464) N-[2-({4-chloro-3-[(1-methylpiperidin-4-yl)methoxy]benzyl}oxy)-6-methyl-5,6,7,8-tetrahydro-1,6-naphthyridine-3-yl]-4-methylbenzenesulfonamide,
(465) 2,3-dichloro-N-[2-({4-chloro-3-[(1-methylpiperidin-4-yl)methoxy]benzyl}oxy)-6-methyl-5,6,7,8-tetrahydro-1,6-naphthyridine3-yl]benzenesulfonamide,
(466) 2-chloro-N-[2-({4-chloro-3-[(1-methylpiperidin-4-yl)methoxy]benzyl}oxy)-6-methyl-5,6,7,8-tetrahydro-1,6-naphthyridine3-yl]benzenesulfonamide,
(467) N-[2-({4-chloro-3-[(1-methylpiperidin-4-yl)methoxy]benzyl}oxy)-6-methyl-5,6,7,8-tetrahydro-1,6-naphthyridine3-yl]-2-(trifluoromethyl)benzenesulfonamide, (468) N-[2-({4-chloro-3-[2-(dimethylamino)ethoxy]benzyl}oxy)-6-methyl-5,6,7,8-tetrahydro-1,6-naphthyridine3-yl]-4-methylbenzenesulfonamide, (469) 2,3-dichloro-N-[2-({4-chloro-3-[2-(dimethylamino)ethoxy]benzyl}oxy)-6-methyl-5,6,7,8-tetrahydro-1,6-naphthyridine3-yl]benzenesulfonamide, (470) 2-chloro-N-[2-({4-chloro-3-[2-(dimethylamino)ethoxy]benzyl}oxy)-6-methyl-5,6,7,8-tetrahydro-1,6-naphthyridine3-yl]benzenesulfonamide, (471) N-[2-({4-chloro-3-[2-(dimethylamino)ethoxy]benzyl}oxy)-6-methyl-5,6,7,8-tetrahydro-1,6-naphthyridine3-yl]-2-(trifluoromethyl)benzenesulfonamide, (472) 4-methyl-N-{6-methyl-2-[(4-methyl-3,4-dihydro-2H-1,4-benzoxazin-7-yl)methoxy]-5,6,7,8-tetrahydro-1,6-naphthyridine3-yl}benzenesulfonamide, (473) 2,3-dichloro-N-{6-methyl-2-[(4-methyl-3,4-dihydro-2H-1,4-benzoxazin-7-yl)methoxy]-5,6,7,8-tetrahydro-1,6-naphthyridine3-yl}benzenesulfonamide, (474) 2-chloro-N-{6-methyl-2-[(4-methyl-3,4-dihydro-2H-1,4-benzoxazin-7-yl)methoxy]-5,6,7,8-tetrahydro-1,6-naphthyridine3-yl}benzenesulfonamide, (475) N-{6-methyl-2-[(4-methyl-3,4-dihydro-2H-1,4-benzoxazin-7-yl)methoxy]-5,6,7,8-tetrahydro-1,6-naphthyridine3-yl}-2-(trifluoromethyl)benzenesulfonamide, (476) N-[2-({4-chloro-3-[(1-methylpiperidin-4-yl)methoxy]benzyl}oxy)-1,6-naphthyridine3-yl]-4-methylbenzenesulfonamide, (477) 2,3-dichloro-N-[2-({4-chloro-3-[(1-methylpiperidin-4-yl)methoxy]benzyl}oxy)-1,6-naphthyridine3-yl]benzenesulfonamide, (478) 2-chloro-N-[2-({4-chloro-3-[(1-methylpiperidin-4-yl)methoxy]benzyl}oxy)-1,6-naphthyridine3-yl]benzenesulfonamide, (479) N-[2-({4-chloro-3-[(1-methylpiperidin-4-yl)methoxy]benzyl}oxy)-1,6-naphthyridine3-yl]-2-(trifluoromethyl)benzenesulfonamide, (480) N-[2-({4-chloro-3-[2-(dimethylamino)ethoxy]benzyl}oxy)-1,6-naphthyridine3-yl]-4-methylbenzenesulfonamide, (481) 2,3-dichloro-N-[2-({4-chloro-3-[2-(dimethylamino)ethoxy]benzyl}oxy)-1,6-naphthyridine3-yl]benzenesulfonamide, (482) 2-chloro-N-[2-({4-chloro-3-[2-(dimethylamino)ethoxy]benzyl}oxy)-1,6-naphthyridine3-yl]benzenesulfonamide, (483) N-[2-({4-chloro-3-[2-(dimethylamino)ethoxy]benzyl}oxy)-1,6-naphthyridine3-yl]-2-(trifluoromethyl)benzenesulfonamide, (484) 4-methyl-N-{2-[(4-methyl-3,4-dihydro-2H-1,4-benzoxazin-7-yl)methoxy]-1,6-naphthyridine3-yl}benzenesulfonamide, (485) 2,3-dichloro-N-{2-[(4-methyl-3,4-dihydro-2H-1,4-benzoxazin-7-yl)methoxy]-1,6-naphthyridine3-yl}benzenesulfonamide, (486) 2-chloro-N-{2-[(4-methyl-3,4-dihydro-2H-1,4-benzoxazin-7-yl)methoxy]-1,6-naphthyridine3-yl}benzenesulfonamide, (487) N-{2-[(4-methyl-3,4-dihydro-2H-1,4-benzoxazin-7-yl)methoxy]-1,6-naphthyridine3-yl}-2-(trifluoromethyl)benzenesulfonamide, (488) N-[3-({4-chloro-3-[(1-methylpiperidin-4-yl)methoxy]benzyl}oxy)quinoxalin-2-yl]-4-methylbenzenesulfonamide, (489) 2,3-dichloro-N-[3-({4-chloro-3-[(1-methylpiperidin-4-yl)methoxy]benzyl}oxy)quinoxalin-2-yl]benzenesulfonamide, (490) 2-chloro-N-[3-({4-chloro-3-[(1-methylpiperidin-4-yl)methoxy]benzyl}oxy)quinoxalin-2-yl]benzenesulfonamide, (491) N-[3-({4-chloro-3-[(1-methylpiperidin-4-yl)methoxy]benzyl}oxy)quinoxalin-2-yl]-2-(trifluoromethyl)benzenesulfonamide, (492) N-[3-({4-chloro-3-[2-(dimethylamino)ethoxy]benzyl}oxy)quinoxalin-2-yl]-4-methylbenzenesulfonamide, (493) 2,3-dichloro-N-[3-({4-chloro-3-[2-(dimethylamino)ethoxy]benzyl}oxy)quinoxalin-2-yl]benzenesulfonamide, (494) 2-chloro-N-[3-({4-chloro-3-[2-(dimethylamino)ethoxy]benzyl}oxy)quinoxalin-2-yl]benzenesulfonamide, (495) N-[3-({4-chloro-3-[2-(dimethylamino)ethoxy]benzyl}oxy)quinoxalin-2-yl]-2-(trifluoromethyl)benzenesulfonamide, (496) 4-methyl-N-{3-[(4-methyl-3,4-dihydro-2H-1,4-benzoxazin-7-yl)methoxy]quinoxalin-2-yl}benzenesulfonamide, (497) 2,3-dichloro-N-{3-[(4-methyl-3,4-dihydro-2H-1,4-benzoxazin-7-yl)methoxy]quinoxalin-2-yl}benzenesulfonamide, (498) 2-chloro-N-{3-[(4-methyl-3,4-dihydro-2H-1,4-benzoxazin-7-yl)methoxy]quinoxalin-2-yl}benzenesulfonamide, (499) N-{3-[(4-methyl-3,4-dihydro-2H-1,4-benzoxazin-7-yl)methoxy]quinoxalin-2-yl}-2-(trifluoromethyl)benzenesulfonamide, (500) N-[3-({4-chloro-3-[(1-methylpiperidin-4-yl)methoxy]benzyl}oxy)-6,7-dihydro-5H-cyclopent[b]pyrazin-2-yl]-4-methylbenzenesulfonamide, (501) 2,3-dichloro-N-[3-({4-chloro-3-[(1-methylpiperidin-4-yl)methoxy]benzyl}oxy)-6,7-dihydro-5H-cyclopent[b]pyrazin-2-yl]benzenesulfonamide, (502) 2-chloro-N-[3-({4-chloro-3-[(1-methylpiperidin-4-yl)methoxy]benzyl}oxy)-6,7-dihydro-5H-cyclopent[b]pyrazin-2-yl]benzenesulfonamide, (503) N-[3-({4-chloro-3-[(1-methylpiperidin-4-yl)methoxy]benzyl}oxy)-6,7-dihydro-5H-cyclopent[b]pyrazin-2-yl]-2-(trifluoromethyl)benzenesulfonamide, (504) N-[3-({4-chloro-3-[2-(dimethylamino)ethoxy]benzyl}oxy)-6,7-dihydro-5H-cyclopent[b]pyrazin-2-yl]-4-methylbenzenesulfonamide, (505) 2,3-dichloro-N-[3-({4-chloro-3-[2-(dimethylamino)ethoxy]benzyl}oxy)-6,7-dihydro-5H-cyclopent[b]pyrazin-2-yl]benzenesulfonamide, (506) 2-chloro-N-[3-({4-chloro-3-[2-(dimethylamino)ethoxy]benzyl}oxy)-6,7-dihydro-5H-cyclopent[b]pyrazin-2-yl]benzenesulfonamide, (507) N-[3-({4-chloro-3-[2-(dimethylamino)ethoxy]benzyl}oxy)-6,7-dihydro-5H-cyclopent[b]pyrazin-2-yl]-2-(trifluoromethyl)benzenesulfonamide, (508) 4-methyl-N-{3-[(4-methyl-3,4-dihydro-2H-1,4-benzoxazin-7-yl)methoxy]-6,7-dihydro-5H-cyclopent[b]pyrazin-2-yl}benzenesulfonamide, (509) 2,3-dichloro-N-{3-[(4-methyl-3,4-dihydro-2H-1,4-benzoxazin-7-yl)methoxy]-6,7-dihydro-5H-cyclopent[b]pyrazin-2-yl}benzenesulfonamide, (510) 2-chloro-N-{3-[(4-methyl-3,4-dihydro-2H-1,4-benzoxazin-7-yl)methoxy]-6,7-dihydro-5H-cyclopent[b]pyrazin-2-yl}benzenesulfonamide, (511) N-{3-[(4-methyl-3,4-dihydro-2H-1,4-benzoxazin-7-yl)methoxy]-6,7-dihydro-5H-cyclopent[b]pyrazin-2-yl}-2-(trifluoromethyl)benzenesulfonamide, (512) N-[3-({4-chloro-3-[(1-methylpiperidin-4-yl)methoxy]benzyl}oxy)-5,6,7,8-tetrahydroquinoxalin-2-yl]-4-methylbenzenesulfonamide,
(513) 2,3-dichloro-N-[3-({4-chloro-3-[(1-methylpiperidin-4-yl)methoxy]benzyl}oxy)-5,6,7,8-tetrahydroquinoxalin-2-yl]benzenesulfonamide,
(514) 2-chloro-N-[3-({4-chloro-3-[(1-methylpiperidin-4-yl)methoxy]benzyl}oxy)-5,6,7,8-tetrahydroquinoxalin-2-yl]benzenesulfonamide,
(515) N-[3-({4-chloro-3-[(1-methylpiperidin-4-yl)methoxy]benzyl}oxy)-5,6,7,8-tetrahydroquinoxalin-2-yl]-2-(trifluoromethyl)benzenesulfonamide,
(516) N-[3-({4-chloro-3-[2-(dimethylamino)ethoxy]benzyl}oxy)-5,6,7,8-tetrahydroquinoxalin-2-yl]-4-methylbenzenesulfonamide,
(517) 2,3-dichloro-N-[3-({4-chloro-3-[2-(dimethylamino)ethoxy]benzyl}oxy)-5,6,7,8-tetrahydroquinoxalin-2-yl]benzenesulfonamide,
(518) 2-chloro-N-[3-({4-chloro-3-[2-(dimethylamino)ethoxy]benzyl}oxy)-5,6,7,8-tetrahydroquinoxalin-2-yl]benzenesulfonamide,
(519) N-[3-({4-chloro-3-[2-(dimethylamino)ethoxy]benzyl}oxy)-5,6,7,8-tetrahydroquinoxalin-2-yl]-2-(trifluoromethyl)benzenesulfonamide,
(520) 4-methyl-N-{3-[(4-methyl-3,4-dihydro-2H-1,4-benzoxazin-7-yl)methoxy]-5,6,7,8-tetrahydroquinoxalin-2-yl}benzenesulfonamide,
(521) 2,3-dichloro-N-{3-[(4-methyl-3,4-dihydro-2H-1,4-benzoxazin-7-yl)methoxy]-5,6,7,8-tetrahydroquinoxalin-2-yl}benzenesulfonamide,
(522) 2-chloro-N-{3-[(4-methyl-3,4-dihydro-2H-1,4-benzoxazin-7-yl)methoxy]-5,6,7,8-tetrahydroquinoxalin-2-yl}benzenesulfonamide,
(523) N-{3-[(4-methyl-3,4-dihydro-2H-1,4-benzoxazin-7-yl)methoxy]-5,6,7,8-tetrahydroquinoxalin-2-yl}-2-(trifluoromethyl)benzenesulfonamide,
(524) N-[5-({4-chloro-3-[(1-methylpiperidin-4-yl)methoxy]benzyl}oxy)pyrimidin-4-yl]-4-methylbenzenesulfonamide,
(525) 2,3-dichloro-N-[5-({4-chloro-3-[(1-methylpiperidin-4-yl)methoxy]benzyl}oxy)pyrimidin-4-yl]benzenesulfonamide,
(526) 2-chloro-N-[5-({4-chloro-3-[(1-methylpiperidin-4-yl)methoxy]benzyl}oxy)pyrimidin-4-yl]benzenesulfonamide,
(527) N-[5-({4-chloro-3-[(1-methylpiperidin-4-yl)methoxy]benzyl}oxy)pyrimidin-4-yl]-2-(trifluoromethyl)benzenesulfonamide,
(528) N-[5-({4-chloro-3-[2-(dimethylamino)ethoxy]benzyl}oxy)pyrimidin-4-yl]-4-methylbenzenesulfonamide,
(529) 2,3-dichloro-N-[5-({4-chloro-3-[2-(dimethylamino)ethoxy]benzyl}oxy)pyrimidin-4-yl]benzene sulfonamide,
(530) 2-chloro-N-[5-({4-chloro-3-[2-(dimethylamino)ethoxy]benzyl}oxy)pyrimidin-4-yl]benzenesulfonamide,
(531) N-[5-({4-chloro-3-[2-(dimethylamino)ethoxy]benzyl}oxy)pyrimidin-4-yl]-2-(trifluoromethyl)benzenesulfonamide,
(532) 4-methyl-N-{5-[(4-methyl-3,4-dihydro-2H-1,4-benzoxazin-7-yl)methoxy]pyrimidin-4-yl}benzene sulfonamide,
(533) 2,3-dichloro-N-{5-[(4-methyl-3,4-dihydro-2H-1,4-benzoxazin-7-yl)methoxy]pyrimidin-4-yl}benzenesulfonamide,
(534) 2-chloro-N-{5-[(4-methyl-3,4-dihydro-2H-1,4-benzoxazin-7-yl)methoxy]pyrimidin-4-yl}benzenesulfonamide,
(535) N-{5-[(4-methyl-3,4-dihydro-2H-1,4-benzoxazin-7-yl)methoxy]pyrimidin-4-yl}-2-(trifluoromethyl)benzenesulfonamide,
(536) N-[5-bromo-3-({4-chloro-3-[(1-methylpiperidin-4-yl)methoxy]benzyl}oxy)pyridin-2-yl]-4-methylbenzenesulfonamide,
(537) N-[5-bromo-3-({4-chloro-3-[(1-methylpiperidin-4-yl)methoxy]benzyl}oxy)pyridin-2-yl]-2,3-dichlorobenzenesulfonamide,
(538) N-[5-bromo-3-({4-chloro-3-[(1-methylpiperidin-4-yl)methoxy]benzyl}oxy)pyridin-2-yl]-2-chlorobenzenesulfonamide,
(539) N-[5-bromo-3-({4-chloro-3-[(1-methylpiperidin-4-yl)methoxy]benzyl}oxy)pyridin-2-yl]-2-(trifluoromethyl)benzenesulfonamide,
(540) N-[5-bromo-3-({4-chloro-3-[2-(dimethylamino)ethoxy]benzyl}oxy)pyridin-2-yl]-4-methylbenzenesulfonamide,
(541) N-[5-bromo-3-({4-chloro-3-[2-(dimethylamino)ethoxy]benzyl}oxy)pyridin-2-yl]-2,3-dichlorobenzenesulfonamide,
(542) N-[5-bromo-3-({4-chloro-3-[2-(dimethylamino)ethoxy]benzyl}oxy)pyridin-2-yl]-2-chlorobenzenesulfonamide,
(543) N-[5-bromo-3-({4-chloro-3-[2-(dimethylamino)ethoxy]benzyl}oxy)pyridin-2-yl]-2-(trifluoromethyl)benzenesulfonamide,
(544) N-{5-bromo-3-[(4-methyl-3,4-dihydro-2H-1,4-benzoxazin-7-yl)methoxy]pyridin-2-yl}-4-methylbenzenesulfonamide,
(545) N-{5-bromo-3-[(4-methyl-3,4-dihydro-2H-1,4-benzoxazin-7-yl)methoxy]pyridin-2-yl}-2,3-dichlorobenzenesulfonamide,
(546) N-{5-bromo-3-[(4-methyl-3,4-dihydro-2H-1,4-benzoxazin-7-yl)methoxy]pyridin-2-yl}-2-chlorobenzenesulfonamide or
(547) N-{5-bromo-3-[(4-methyl-3,4-dihydro-2H-1,4-benzoxazin-7-yl)methoxy]pyridin-2-yl}-2-(trifluoromethyl)benzenesulfonamide.

As the specifically preferable compounds, for example, the compounds described in the following (1) to (14) or Examples in the specification, a salt thereof, an N-oxide thereof, a solvate thereof or a prodrug thereof, and the like can be cited.

(1) N-[5-bromo-3-({3-[2-(dimethylamino)ethoxy]-4-methoxybenzyl}oxy)pyridin-2-yl]-4-methylbenzenesulfonamide;
(2) 3-chloro-N-[3-({4-chloro-3-[(1-methylpiperidin-4-yl)methoxy]benzyl}oxy)-5-methylpyrazin-2-yl]-2-methylbenzenesulfonamide;
(3) 2-chloro-N-[3-({4-chloro-3-[(1-methylpiperidin-4-yl)methoxy]benzyl}oxy)-5-methylpyrazin-2-yl]-2-methylbenzenesulfonamide;
(4) 3-chloro-2-methyl-N-[5-methyl-3-(quinolin-2-ylmethoxy)pyrazin-2-yl]benzenesulfonamide;
(5) 2-chloro-N-[3-({3-[2-(dimethylamino)ethoxy]-4-methoxybenzyl}oxy)quinoxalin-2-yl]benzenesulfonamide;
(6) N-[3-({4-chloro-3-[(1-methylpiperidin-4-yl)methoxy]benzyl}oxy)-5-methylpyrazin-2-yl]-4-methylbenzenesulfonamide,
(7) N-[3-({4-chloro-3-[(1-methylpiperidin-4-yl)methoxy]benzyl}oxy)-5-methylpyrazin-2-yl]-2-(trifluoromethyl)benzenesulfonamide,
(8) 3-chloro-2-methyl-N-{5-methyl-3-[(2-methyl-1,2,3,4-tetrahydro-7-isoquinolinyl)methoxy]-2-pyrazinyl}benzenesulfonamide;

(9) N-[5-bromo-3-({4-chloro-3-[(1-methyl-4-piperidinyl) methoxy]benzyl}oxy)-2-pyrazinyl]-4-methylbenzene-sulfonamide;

(10) 3-chloro-N-{3-[(3,5-dimethyl-1-phenyl-1H-pyrazol-4-yl)methoxy]-5-methyl-2-pyrazinyl}-2-methylbenzene-sulfonamide;

(11) 3-chloro-2-methyl-N-{5-methyl-3-[(2-phenyl-1,3-thiazol-4-yl)methoxy]-2-pyrazinyl}benzenesulfonamide;

(12) tert-butyl 7-{[(6-bromo-3-{[(4-methylphenyl)sulfonyl]amino}-2-pyrazinyl)oxy]methyl}-3,4-dihydro-2(1H)-isoquinolinecarboxylate;

(13) N-[5-chloro-3-({3-[2-(dimethylamino)ethoxy]-4-methoxybenzyl}oxy)-2-pyridinyl]-4-methylbenzene-sulfonamide;

(14) 3-chloro-N-[5-chloro-3-({3-[2-(dimethylamino)ethoxy]-4-methoxybenzyl}oxy)-2-pyridinyl]-2-methyl-benzenesulfonamide.

Process for the preparation of the compound of the present invention:

A compound of the present invention represented by formula (I) may be prepared by optimized and/or combined known methods, for example, a method shown below, methods described in Examples, or methods described in *Comprehensive Organic Transformations: A Guide to Functional Group Preparations,* 2nd Edition (Richard C. Larock, John Wiley & Sons Inc., 1999), or other methods. In addition, the starting material in each preparation method described below may be used in the form of a salt. Such salt used is the salt of compounds represented by formula (I) as defined above.

Among the compounds of the present invention represented by formula (I), a compound in which J is bound to ring D via an oxygen atom, i.e., a compound represented by formula (I-A):

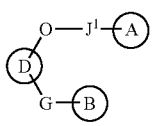

(I-A)

wherein $J^1$ represents a bond or a spacer having 1 to 7 atom(s) in its main chain, and other symbols have the same meanings as described above, can be prepared by a method of (a-1) or (b-1) shown below.

(a-1): A compound of the present invention represented by formula (I-A) can be prepared by subjecting a compound represented by formula (II):

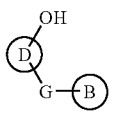

(II)

wherein all symbols have the same meanings as described above, and a compound represented by formula (III):

(III)

wherein X represents a leaving group (a leaving group includes, for example, halogen, methanesulfonyloxy (OMs), p-toluenesulfonyloxy (OTs), trifluoromethanesulfonyloxy (OTf), and the like.) or hydroxy, and other symbols have the same meanings as described above, to etherification, and if necessary, to deprotection reaction and/or to cleavage reaction from a resin.

The etherification is carried out by a known method, for example, by reacting in an organic solvent (N,N-dimethylformamide, dimethylsulfoxide, chloroform, methylene chloride, diethyl ether, tetrahydrofuran, methyl t-butyl ether, 1,4-dioxane, 1,2-dimethoxyethane, etc.) in the presence of a base [alkali metal hydride (sodium hydride, potassium hydride, etc.), organometal reagent (N-butyl lithium, sodium hydride, etc.), quaternary ammonium salt (tetrabutylammonium fluoride, etc.), or the like] at 0 to 120° C.

And the etherification reaction when X is hydroxy is known. It carried out, with a corresponding alcohol compound, by reacting in an organic solvent (dichloromethane, diethylether, tetrahydrofuran, acetonitrile, benzene, toluene, etc.) in the presence of an azo compound (diethyl azodicarboxylate (DEAD), isopropyl azodicarboxylate, 1,1'-(azodicarbonyl)dipiperidine, 1,1'-azobis(N,N-dimethylformamide), etc.) and phosphine compound (triphenylphosphine, tributylphosphine, trimethylphosphine, polymer-supported triphenyl phosphine, etc.) at 0 to 60° C.

The compound wherein at least one group of formula (I-A) has carboxy, hydroxy, amino or thiol can be prepared by subjecting the compound in which the respective groups are protected by protective group, to deprotection reaction.

A protective group for carboxy includes, for example, methyl, ethyl, allyl, t-butyl, trichloroethyl, benzyl (Bn), phenacyl, and the like.

A protective group for hydroxyl includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc), and the like.

A protective group for amino includes, for example, benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluororenylmethoxycarbonyl, benzyl (Bn), p-methoxybenzyl, benzyloxymethyl (BOM), 2-(trimethylsilyl)ethoxymethyl (SEM), and the like.

A protective group for thiol includes, for example, benzyl, methoxybenzyl, methoxymethyl (MOM), 2-tetrahydropyranyl (THP), diphenylmethyl, acetyl (Ac), and the like.

A protective group for carboxy, hydroxy, amino or thiol is not particularly limited in addition to the above-described groups as long as it can be deprotected easily and selectively. For example, those described in *Protective Groups in Organic Synthesis* (T. W. Greene, John Wiley & Sons Inc., 1999) may be used.

The deprotection of the protective group for carboxy, hydroxy, amino or thiol is well known. For example, it is (1) alkaline hydrolysis, (2) deprotection of a protective group in acidic conditions, (3) deprotection of a protective group by hydrogenolysis, (4) deprotection of a protective group containing silyl, (5) deprotection of a protective group using a metal, (6) deprotection of a protective group using an organometal, and the like.

In the following, these methods are specifically described:

(1) The deprotection of the protective group by alkaline hydrolysis condition may be carried out, for example, in an organic solvent (methanol, tetrahydrofuran, 1,4-dioxane, etc.) with alkaline metal hydroxide (sodium hydroxide, potassium hydroxide, lithium hydroxide, etc.), alkaline earth metal hydroxide (barium hydroxide, calcium hydroxide, etc.), carbonate (sodium carbonate or potassium carbonate, etc.), an aqueous solution thereof or a mixture thereof at 0 to 40° C.

(2) The deprotection of the protective group in acidic conditions may be carried out, for example, in an organic solvent (methylene chloride, chloroform, 1,4-dioxane, ethyl acetate, anisole, etc.), organic acid (acetic acid, trifluoroacetic acid, methanesulfonic acid, p-toluenesulfonic acid, etc.), inorganic acid (hydrochloric acid, sulfuric acid, etc.), or a mixture thereof (hydrogen bromide/acetic acid, etc.) at 0 to 100° C.

(3) The deprotection of the protective group by hydrogenolysis may be carried out, for example, in a solvent (ethers (tetrahydrofuran, 1,4-dioxane, 1,2-dimethoxyethane, diethyl ether, etc.), alcohols (methanol, ethanol, etc.), benzenes (benzene, toluene, etc.), ketones (acetone, methylethylketone, etc.), nitriles (acetonitrile, etc.), amides (N,N-dimethylformamide, etc.), water, ethyl acetate, acetic acid, a mixture of two or more thereof, etc.) in the presence of a catalyst (palladium on carbon, palladium black, palladium hydroxide, platinum oxide, Raney nickel, etc.) under hydrogen atmosphere at a normal pressure or elevated pressure, or in the presence of ammonium formate at 0 to 200° C.

(4) The deprotection of the protective group for silyl may be carried out, for example, in a water-miscible organic solvent (tetrahydrofuran, acetonitrile, etc.), with fluoride (tetrabutylammonium fluoride, an aqueous solution of hydrofluoride, hydrofluoride-pyridine complex, etc.) at −20 to 40° C.

(5) The deprotection of the protective group using a metal may be carried out, for example, in an acidic solvent (acetic acid, a buffer of pH 4.2 to 7.2, a mixed solution of the buffer and an organic solvent such as tetrahydrofuran, etc.) in the presence of powder zinc, with or without an ultrasonic wave at a temperature of 0 to 40° C.

(6) The deprotection of the protective group using a metal complex may be carried out, for example, in an organic solvent (methylene chloride, N,N-dimethylformamide, tetrahydrofuran, ethyl acetate, acetonitrile, 1,4-dioxane, ethanol, etc.), water or a mixed solvent thereof in the presence of a trap reagent (tributyltin hydride, triethylsilane, dimedone, morpholine, diethylamine, pyrrolidine, etc.), an organic acid (acetic acid, formic acid, 2-ethylhexanic acid, etc.) and/or an organic acid salt (sodium 2-ethylhexanate, potassium 2-ethylhexanate, etc) in the presence or absence of a phosphine reagent (triphenylphosphine, etc.) using a metal complex (tetrakis(triphenylphosphine)palladium (O), dichlorobis(triphenylphosphine)palladium (II), palladium acetate (II), chlorotris(triphenylphosphine)rhodium (I), etc.) at 0 to 40° C.

In addition to the above methods, the deprotection may be carried out by the method described in *Protective Groups in Organic Synthesis* (T. W. Greene, John Wiley & Sons Inc., 1999).

Furthermore, if the compound has a moiety to bind to a resin in the molecule, and the resin is a polystyrene resin, the compound of the present invention can be cleaved from the resin by the following method. The cleavage reaction from the resin may be carried out by a known method, for example, by reacting in an organic solvent (methylene chloride, 1,2-dichloroethane, toluene, etc.), with acid (acetic acid, trifluoroacetic acid, hydrochloric acid, etc.) at 0 to 100° C.

As well understood to the skilled persons in the art, the objective compounds of the present invention may be prepared easily by using these deprotection reactions.

Furthermore, if necessary, after those reactions, a procedure of converting the compound into the objective non-toxic salts may be carried out according to a known method.

(b-1): A compound of the present invention represented by formula (I-A) can be prepared by subjecting a compound represented by formula (IV):

wherein all symbols have the same meanings as described above, and a compound represented by formula (V):

wherein all symbols have the same meanings as described above, to the same reaction as those in above-described (a-1), and if necessary, to deprotection reaction and/or to cleavage reaction from a resin. The deprotection of the protective group can be carried out in the same manner as those in the above-described method. Furthermore, if the compound has a moiety to bind to a resin in the molecule, and the resin is a polystyrene resin, the compound of the present invention can be cleaved from the resin in the same manner as those in the above-described method.

Among the compounds of the present invention represented by formula (I), a compound in which G is bound to ring D via —NHSO$_2$—, i.e., a compound represented by formula (I-B):

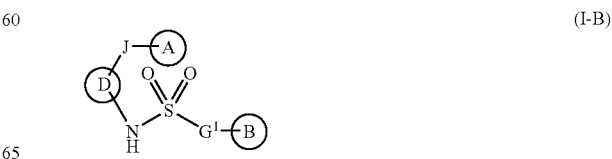

wherein $G^1$ represents a bond or a spacer having 1 or 2 atom(s) in its main chain, and other symbols have the same meanings as described above, can be prepared by a method of (a-2) or (b-2) shown below.

(a-2): A compound of the present invention represented by formula (I-B) can be prepared by subjecting a compound of formula (VI):

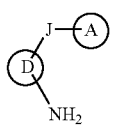

(VI)

wherein all symbols have the same meanings as described above, and a compound of formula (VII):

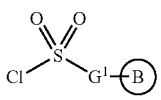

(VII)

wherein all symbols have the same meanings as described above, to sulfonamidation.

The sulfonamidation is known and it may be carried out, for example, by reacting in an organic solvent (chloroform, methylene chloride, 1,2-dichloroethane, diethyl ether, tetrahydrofuran, etc.) in the presence of a base (diisopropylethylamine, pyridine, triethylamine, N,N-dimethylaniline, N,N-dimethylaminopyridine, sodium hydride, potassium hydride, etc.) at 0 to 40° C.

The compound wherein at least one group of formula (I-B) contains carboxy, hydroxy, amino or thiol can be prepared by subjecting the compound in which the respective groups are protected by protective group, to deprotection reaction. The deprotection of the protective group can be carried out in the same manner as those in the above-described method. Furthermore, if the compound has a moiety to bind to a resin in the molecule, and the resin is a polystyrene resin, the compound of the present invention can be cleaved from the resin in the same manner as those in the above-described method.

(b-2): A compound of the present invention represented by formula (I-B) can be prepared by subjecting a compound represented by formula (VIII):

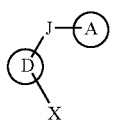

(VIII)

wherein all symbols have the same meanings as described above, and a compound represented by formula (IX):

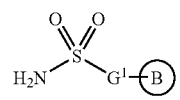

(IX)

wherein all symbols have the same meanings as described above, to reaction, and if necessary, to deprotection reaction and/or to cleavage reaction from a resin.

This reaction may be carried out by a known method, for example, by reacting in an organic solvent (N,N-dimethylformamide, N,N-dimethylacetamide, dimethylsulfoxide, etc.) in the presence or absence of a base (potassium carbonate, cesium carbonate, triethylamine, N-butyl lithium, sodium hydride, sodium hydroxide, etc.) at 0 to 200° C.

The deprotection of the protective group can be carried out in the same manner as those in the above-described method. Furthermore, if the compound has a moiety to bind to a resin in the molecule, and the resin is a polystyrene resin, the compound of the present invention can be cleaved from the resin in the same manner as those in the above-described method.

Among the compounds of the present invention represented by formula (I), a compound in which G is bound to ring D via —NHCO—, i.e., a compound represented by formula (I-C):

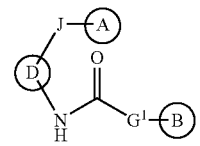

(I-C)

wherein all symbols have the same meanings as described above, can be prepared by subjecting a compound represented by formula (VI) and a compound represented by formula (X):

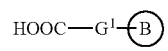

(X)

wherein all symbols have the same meanings as described above, to amidation, and if necessary, to deprotection reaction and/or to cleavage reaction from a resin.

The amidation is well known, and it includes, for example, (1) a method using an acyl halide, (2) a method using a mixed acid anhydride, and (3) a method using a condensing agent, and the like.

In the following, these methods are explained in detail.

(1) The method using an acyl halide may be carried out, for example, by reacting carboxylic acid with acyl halide (e.g., oxalyl chloride, thionyl chloride, etc.) in an organic solvent (e.g., chloroform, methylene chloride, diethyl ether, tetrahydrofuran, etc.) or without a solvent at −20° C. to reflux temperature. And then the obtained acyl halide derivative may be reacted with amine in an inert organic solvent (e.g., chloroform, methylene chloride, diethyl ether, tetrahydrofuran, etc.) in the presence of a base (e.g., pyridine, triethyl amine, N,N-dimethyl aniline, N,N-dimethylaminopyridine, diisopropylethylamine, etc.) at 0 to 40° C. Alternatively, the obtained acyl halide derivative may be reacted with amine in an organic solvent (e.g., 1,4-dioxane, tetrahydrofuran, etc.) using an alkaline aqueous solution (e.g., sodium bicarbonate, sodium hydroxide, etc.) at 0 to 40° C.

(2) The method using a mixed acid anhydride may be carried out, for example, by reacting carboxylic acid with acyl halide (e.g., pivaloyl chloride, p-toluenesulfonyl chloride, methanesulfonyl chloride, etc.) or an acid derivative (e.g., ethyl chloroformate, isobutyl chloroformate, etc.) in an organic solvent (e.g., chloroform, methylene chloride, diethyl ether, tetrahydrofuran, etc.) or without a solvent in the presence of a base (e.g., pyridine, triethylamine, N,N-dimethylaniline, N,N-dimethylaminopyridine, diisopropylethylamine, etc.) at 0 to 40° C. And then the obtained mixed acid anhydride derivative may be reacted with amine in an organic solvent (e.g., chloroform, methylene chloride, diethyl ether, tetrahydrofuran, etc.) at 0 to 40° C.

(3) The method using a condensing agent may be carried out, for example, by reacting carboxylic acid with amine in an organic solvent (e.g., chloroform, methylene chloride, N,N-dimethylformamide, diethyl ether, tetrahydrofuran, etc.) or without a solvent in the presence or absence of a base (e.g., pyridine, triethylamine, N,N-dimethylaniline, N,N-dimethylaminopyridine, etc.), using a condensing agent (e.g., 1,3-dicyclohexyl carbodiimide (DCC), 1-ethyl-3-[3-(dimethylamino)propyl]carbodiimide (EDC), 1,3-diisopropylcarbodiimide (DIC), 1,1'-carbodiimidazole (CDI), 2-chloro-1-methylpyridinium iodide, 1-propanephosphonic acid cyclic anhydride (PPA), etc.) in the presence or absence of 1-hydroxybenzotriazole (HOBt) at 0 to 40° C.

The reactions described in (1), (2) and (3) may be carried out under an atmosphere of an inert gas (e.g., argon, nitrogen, etc.) on anhydrous condition.

The compound in which at least one group of formula (I-C) contains carboxy, hydroxy, amino or thiol can be prepared by subjecting the compound in which the respective groups are protected by protective group, to deprotection reaction. The deprotection of the protective group can be carried out in the same manner as those in the above-described method. Furthermore, if the compound has a moiety to bind to a resin in the molecule, and the resin is a polystyrene resin, the compound of the present invention can be cleaved from the resin in the same manner as those in the above-described method.

Among the compounds of the present invention represented by formula (I), a compound in which J is a bond or bound to ring D via carbon, i.e., a compound represented by formula (I-D):

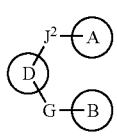

(I-D)

wherein $J^2$ is the same as J, wherein the atoms which bind to the bond or ring D are carbon atoms, and other symbols have the same meanings as described above, can be prepared by a method of (a-3) or (b-3) shown below.

(a-3): A compound of the present invention represented by formula (I-D) can be prepared by subjecting a compound represented by formula (IV) and a compound represented by formula (XI):

(XI)

wherein all symbols have the same meanings as described above, to reaction, and if necessary, to deprotection reaction and/or to cleavage reaction from a resin.

The reaction of the compound represented by formula (IV) and the compound represented by formula (XI) may be carried out by a known method, for example, by reacting in an organic solvent (benzene, toluene, N,N-dimethylformamide, 1,4-dioxane, tetrahydrofuran, methanol, acetonitrile, 1,2-dimethoxyethane, acetone, etc.) in the presence of a base (sodium ethylate, sodium hydroxide, potassium hydroxide, triethylamine, sodium carbonate, sodium hydrocarbonate, potassium carbonate, cesium carbonate, thallium carbonate, tripotassium phosphate, cesium fluoride, barium hydroxide, tetrabutylammonium fluoride, etc.) or an aqueous solution thereof, or a mixture thereof and a catalyst (tetrakis(triphenylphosphine)palladium ($Pd(PPh_3)_4$), dichlorobis(triphenylphosphine)palladium ($Pd(Cl_2(PPh_3)_2)$), palladium acetate ($Pd(OAc)_2$), palladium black, 1,1'-bis(diphenylphosphinoferrocene)dichloropalladium ($PdCl_2(dppf)_2$), dichlorodiallylpalladium ($PdCl_2(allyl)_2$), phenylbis(triphenylphosphine)palladium iodide ($PhPdI(PPh_3)_2$), etc.) at 10 to 120° C.

The deprotection reaction and the cleavage reaction from the resin can be carried out in the same manner as those in the above-described method.

(b-3): A compound of the present invention represented by formula (I-D) can be prepared by subjecting the compound represented by formula (XII):

(XII)

wherein all symbols have the same meanings as described above, and the compound represented by formula (XIII):

(XIII)

wherein all symbols have the same meanings as described above, to the same reaction as those above-described for the compound represented by formula (IV) and the compound represented by formula (XI), and if necessary, to deprotection reaction and/or to cleavage reaction from a resin.

The deprotection reaction and the cleavage reaction from the resin can be carried out in the same manner as those in the above-described method.

Among the compounds of the present invention represented by formula (I), a compound in which G is a bond or bound to ring D via carbon, i.e., a compound represented by formula (I-E):

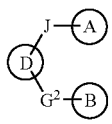
(I-E)

wherein $G^2$ is the same as G, wherein G is a bond or the atom which binds to ring D is carbon, and other symbols have the same meanings as described above, can be prepared by a method of (a-4) or (b-4) shown below.

(a-4): A compound of the present invention represented by formula (I-E) can be prepared by subjecting a compound represented by formula (VIII) and a compound represented by formula (XIV):

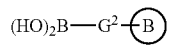
(XIV)

wherein all symbols have the same meanings as described above, to the same reaction as those above-described for the compound represented by formula (IV) and the compound represented by formula (XI), and if necessary, to deprotection reaction and/or to cleavage reaction from a resin.

The deprotection reaction and the cleavage reaction from the resin can be carried out in the same manner as those in the above-described method.

(b-4): A compound of the present invention represented by formula (I-E) can be prepared by subjecting a compound represented by formula (XV):

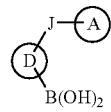
(XV)

wherein all symbols have the same meanings as described above, and a compound represented by formula (XVI):

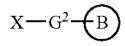
(XVI)

wherein all symbols have the same meanings as described above, to the same reaction as those above-described for the compound represented by formula (IV) and the compound represented by formula (XI), and if necessary, to deprotection reaction and/or to cleavage reaction from a resin.

The deprotection reaction and the cleavage reaction from the resin can be carried out in the same manner as those in the above-described method.

Among the compounds of the present invention represented by formula (I), a compound in which one of substituents in ring D is C1-8, C2-8 alkenyl or C2-8 alkynyl, i.e., a compound represented by formula (I-F):

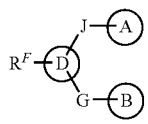
(I-F)

wherein $R^F$ represents C1-8 alkyl, C2-8 alkenyl or C2-8 alkynyl, and other symbols have the same meanings as described above, can be prepared by subjecting a compound represented by formula (XVII):

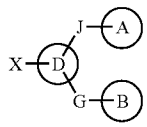
(XVII)

wherein all symbols have the same meanings as described above, to alkylation reaction, and if necessary, to deprotection reaction and/or to cleavage reaction from a resin.

The alkylation reaction may be carried out by a known method, for example, by reacting in an organic solvent (tetrahydrofuran, diethyl ether, etc.) in the presence of an organometal reagent (methylmagnesium bromide, n-butyl lithium, ethynylmagnesium bromide, etc.) and a catalyst ([1, 3-bis(diphenylphosphino)propane]dichloro nickel (II) (NiCl$_2$(dppp)), etc.) at 0 to 40° C.

The deprotection reaction and the cleavage reaction from the resin can be carried out in the same manner as those in the above-described method.

Among the compounds of the present invention represented by formula (I), a compound in which one of substituents in ring D is an optionally substituted cyclic group, i.e., the compound represented by formula (I-G):

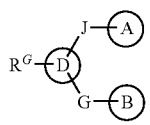
(I-G)

wherein $R^G$ represents an optionally substituted cyclic group, and other symbols have the same meanings as described above, can be prepared by subjecting a compound represented by formula (XVII) and the compound represented by formula (XVIII):

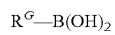
(XVIII)

wherein all symbols have the same meanings as described above, to the same reaction as those above-described for the compound represented by formula (IV) and the compound represented by formula (XI), and if necessary, to deprotection reaction and/or to cleavage reaction from a resin.

The deprotection reaction and the cleavage reaction from the resin can be carried out in the same manner as those in the above-described method.

Among the compounds of the present invention represented by formula (I), a compound in which one of substituents in ring D represents COOR$^{a1}$, and R$^{a1}$ represents a group other than hydrogen, i.e., a compound represented by formula (I-H):

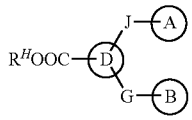
(I-H)

wherein R$^H$ is the same as R$^{a1}$ except hydrogen, and other symbols have the same meanings as described above, can be prepared by subjecting a compound represented by formula (XVII) and a compound represented by formula (XIX):

R$^H$—OH (XIX)

wherein all symbols have the same meanings as described above, to reaction under an atmosphere of carbon monoxide gas, and if necessary, to deprotection reaction and/or to cleavage reaction from a resin.

The reaction of the compound represented by formula (XVII) with the compound represented by formula (XIX) may be carried out by a known method, for example, by reacting in an organic solvent (N,N-dimethylformamide, dimethyl sulfoxide, tetrahydrofuran, 1,2-dimethoxyethane, etc.) in the presence of a base (triethylamine, diisopropylethylamine, N-methylmorpholine, etc.) and a catalyst (tetrakis(triphenylphosphine)palladium (Pd(PPh$_3$)$_4$), dichlorobis(triphenylphosphine)palladium (PdCl$_2$(PPh$_3$)$_2$), palladium acetate (Pd(OAc)$_2$), palladium black, 1,1'-bis(diphenylphosphinoferrocene)dichloropalladium (PdCl$_2$(dppf)$_2$), dichlorodiallylpalladium (PdCl$_2$(allyl)$_2$), phenylbis(triphenylphosphine)palladium iodide (PhPdI(PPh$_3$)$_2$), etc.) at 10 to 120° C. under an atmosphere of carbon monoxide gas.

The deprotection reaction and the cleavage reaction from the resin can be carried out in the same manner as those in the above-described method.

Among the compounds of the present invention represented by formula (I), a compound in which one of substituents in ring D is COOH, i.e., a compound represented by formula (I-I):

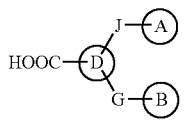
(I-I)

wherein all symbols have the same meanings as described above, can be prepared by a method of (a-5) or (b-5) shown below.

(a-5): A compound of the present invention represented by formula (I-I) can be prepared by subjecting the ester compound represented by formula (I-H) to deprotection reaction. The deprotection of the protective group can be carried out in the same manner as those in the above-described method.

(b-5): A compound of the present invention represented by formula (I-I) can be prepared by subjecting a compound represented by formula (XVII) and 2-trimethylsilylethanol represented by formula (XX):

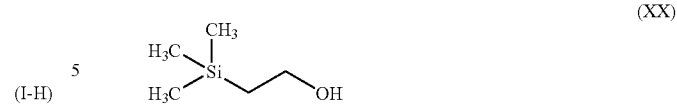
(XX)

to reaction in the presence of carbon monoxide gas, and if necessary, to deprotection reaction and/or to cleavage reaction from a resin.

The reaction between the compound represented by formula (XVII) and the compound represented by formula (XX) may be carried out in the same manner as those above-described in the reaction between the compound represented by formula (XVII) and the compound represented by formula (XIX).

The deprotection reaction and the cleavage reaction from the resin can be carried out in the same manner as those in the above-described method.

Among the compounds of the present invention represented by formula (I), a compound in which one of substituents in ring D represents CONR$^{a1}$R$^{a2}$, i.e., a compound represented by formula (I-J):

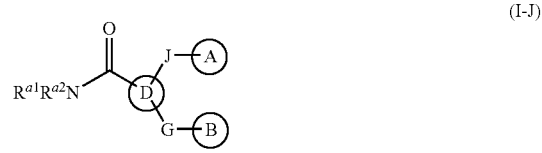
(I-J)

wherein all symbols have the same meanings as described above, can be prepared by subjecting the compound represented by formula (I-I) prepared by above-described method and the compound represented by formula (XXI):

(XXI)

wherein all symbols have the same meanings as described above, to amidation which is the same reaction used for synthesizing the compound represented by formula (I-C), and if necessary, to deprotection reaction and/or to cleavage reaction from a resin.

The deprotection reaction and the cleavage reaction from the resin can be carried out in the same manner as those in the above-described method.

Among the compounds of the present invention represented by formula (I), a compound in which one of substituents in ring D is CH$_2$OH, i.e., a compound represented by formula (I-K):

(I-K)

wherein all symbols have the same meanings as described above, can be prepared by subjecting the compound represented by formula (I-H) or the compound represented by formula (I-I) which was prepared by above-described method, to reduction reaction, and if necessary, to deprotection reaction and/or to cleavage reaction from a resin.

The reduction reaction may be carried out by a known method, for example, by reacting in an organic solvent (tetrahydrofuran, diethyl ether, etc.) in the presence of a reducing agent (sodium borohydride, lithium borohydride, aluminum lithium hydride, diisobutyl aluminum hydride, a boran-dimethylsulfide complex, etc.) at −20 to 100° C.

The deprotection reaction and the cleavage reaction from the resin can be carried out in the same manner as those in the above-described method.

Among the compounds of the present invention represented by formula (I), a compound in which J is bound to ring D via —NHCH$_2$—, i.e., a compound represented by formula (I-L):

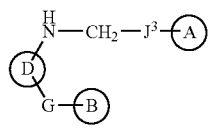

(I-L)

wherein J$^3$ is a bond or a spacer having 1 to 6 atom(s) in its main chain, and other symbols have the same meanings as described above, can be prepared by subjecting a compound represented by formula (XXVI):

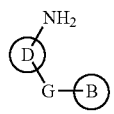

(XXVI)

wherein all symbols have the same meanings as described above, and a compound represented by formula (XXVII):

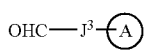

(XXVII)

wherein all symbols have the same meanings as above, to reductive amination and if necessary, to deprotection reaction and/or to cleavage reaction from a resin.

The reductive amination is well known. For example, it may be carried out in an organic solvent (dichloroethane, dichloromethane, dimethylformamide or acetic acid, or a mixture thereof etc.) in the presence of a reducing agent (sodium triacetoxyborohydride, sodium cyanoborohydride or sodium borohydride etc.) at 0 to 40° C.

The deprotection reaction and the cleavage reaction from the resin can be carried out in the same manner as those in the above-described method.

Among the compounds of the present invention represented by formula (I), a compound in which J is bound to ring D via —NHCO—, i.e., a compound represented by formula (I-M):

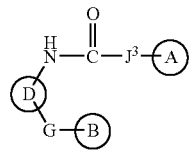

(I-M)

wherein all symbols have the same meanings as described above, can be prepared by subjecting a compound represented by formula (XXVI) and a compound represented by formula (XXVIII):

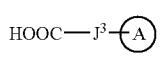

(XXVIII)

wherein all symbols have the same meanings as described above, to amidation and if necessary, to deprotection reaction and/or to cleavage reaction from a resin.

The amidation reaction, deprotection reaction and the cleavage reaction from the resin can be carried out in the same manner as those in the above-described method.

Among the compounds of the present invention represented by formula (I), a compound in which J is bound to ring D via —C≡C—, i.e., a compound represented by formula (I-N):

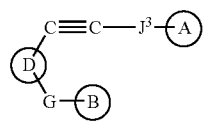

(I-N)

wherein all symbols have the same meanings as described above, can be prepared by subjecting a compound represented by formula (IV) and a compound represented by formula (XXIX):

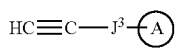

(XXIX)

wherein all symbols have the same meanings as described above, to reaction and if necessary, to deprotection reaction and/or to cleavage reaction from a resin.

This reaction is carried out by a known method. For example, it may be carried out in an organic solvent (e.g., benzene, toluene, dimethylformamide, dioxane, tetrahydrofuran, methanol, acetonitrile, dimethoxyethane, acetone, etc.) in the presence of a base (triethylamine, propylamine, diethylamine, or a mixture thereof, etc.) and a palladium catalyst (tetrakis(triphenylphosphine)palladium (Pd(PPh$_3$)$_4$), dichlorobis(triphenylphosphine)palladium (PdCl$_2$(PPh$_3$)$_2$), palladium acetate (Pd(OAc)$_2$), palladium black, 1,1'-bis(diphenylphosphinoferrocene)dichloropalladium (PdCl$_2$(dppf)$_2$), dichlorodiallylpalladium (PdCl$_2$(allyl)$_2$), phenylbis(triphenylphosphine)palladium iodide (PhPdI(PPh₃)₂), etc.) and a Copper catalyst (copper bromide, copper iodide, etc.) at room temperature to 120° C.

Among the compounds of the present invention represented by formula (II), a compound in which G is bound to ring D via —NHSO₂—, i.e., a compound represented by formula (II-B):

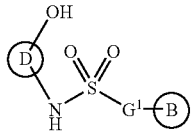

(II-B)

wherein all symbols have the same meanings as described above, can be prepared by subjecting a compound represented by formula (XXII):

(XXII)

wherein X¹ is a leaving group (leaving group has the same meaning as described above) and other symbols have the same meanings as described above, and a compound represented by formula (IX) to the same reaction described in (b-2) and if necessary, to deprotection reaction and/or to cleavage reaction from a resin.

The deprotection reaction and the cleavage reaction from the resin can be carried out in the same manner as those in the above-described method.

Among the compounds represented by formula (IV), a compound in which G is bound to ring D via —NHSO₂—, i.e., a compound represented by formula (IV-B):

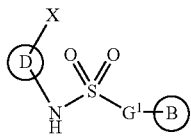

(IV-B)

wherein all symbols have the same meanings as described above, can be prepared by subjecting a compound represented by formula (XXIII):

(XXIII)

wherein all symbols have the same meanings as described above, and a compound represented by formula (IX) to the same reaction described in (b-2) and if necessary, to deprotection reaction and/or to cleavage reaction from a resin.

The deprotection reaction and the cleavage reaction from the resin can be carried out in the same manner as those in the above-described method.

Among the compounds represented by formula (XIII), a compound in which G is bound to ring D via —NHSO₂—, i.e., a compound represented by formula (XII-B):

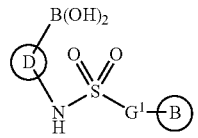

(XII-B)

wherein all symbols have the same meanings as described above, can be prepared by subjecting a compound represented by formula (XXIV):

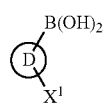

(XXIV)

wherein all symbols have the same meanings as described above, and a compound represented by formula (IX) to the same reaction described in (b-2) and if necessary, to deprotection reaction and/or to cleavage reaction from a resin.

The deprotection reaction and the cleavage reaction from the resin can be carried out in the same manner as those in the above-described method.

Among the compounds represented by formula (VI), a compound in which J is bound to ring D via oxygen atom, i.e., a compound represented by formula (VI-B):

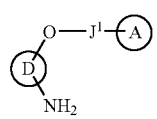

(VI-B)

wherein all symbols have the same meanings as described above, can be prepared by subjecting a compound represented by formula (XXV):

(XXV)

wherein all symbols have the same meanings as described above, and a compound represented by formula (V) to the same reaction described in (a-1) and if necessary, to deprotection reaction and/or to cleavage reaction from a resin.

The deprotection reaction and the cleavage reaction from the resin can be carried out in the same manner as those in the above-described method.

Among the compounds represented by formula (VIII), a compound in which J is bound to ring D via oxygen atom, i.e., a compound represented by formula (VIII-B):

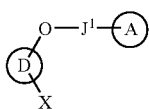

(VIII-B)

wherein all symbols have the same meanings as described above, can be prepared by subjecting a compound represented by formula (XXIII) and a compound represented by formula (V) to the same reaction described in (a-1) and if necessary, to deprotection reaction and/or to cleavage reaction from a resin.

The deprotection reaction and the cleavage reaction from the resin can be carried out in the same manner as those in the above-described method.

Among the compounds represented by formula (XV), a compound in which J is bound to ring D via oxygen atom, i.e., a compound represented by formula (XV-B):

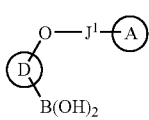

(XV-B)

wherein all symbols have the same meanings as described above, can be prepared by subjecting a compound represented by formula (XXIV) and a compound represented by formula (V) to the same reaction described in (a-1) and if necessary, to deprotection reaction and/or to cleavage reaction from a resin.

The deprotection reaction and the cleavage reaction from the resin can be carried out in the same manner as those in the above-described method.

Among the compounds represented by formula (XXVI), a compound in which G is bound to ring D via —NHSO$_2$—, i.e., a compound represented by formula (XXVI-B):

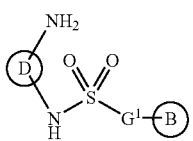

(XXVI-B)

wherein all symbols have the same meanings as described above, can be prepared by subjecting a compound represented by formula (XXVI-C):

(XXVI-C)

wherein all symbols have the same meanings as described above, and a compound represented by formula (VII) to sulfoneamidation, nitration, and reduction sequentially.

This nitration is carried out by a known method. For example, it may be carried out, with nitric acids (e.g., concentrated nitric acid, fuming nitric acid, ammonium nitrate, potassium nitrate, calcium nitrate, sodium nitrite, etc.), in an organic solvent (e.g., carbon tetrachloride, dichloromethane, chloroform, acetic acid, acetic anhydride, etc.) in the presence of acid (concentrated sulfuric acid, concentrated hydrochloric acid, trifluoroacetic acid, sodium hydrogen sulfate, etc.) at 0 to 40° C.

The reduction reaction of nitro is carried out by a known method. For example, the following method is used.

1) It may be carried out, for example, in a solvent [ethers (e.g., tetrahydrofuran, dioxane, dimethoxyethane, diethyl ether, etc.), alcohols (e.g., methanol, ethanol, etc.), benzenes (e.g., benzene, toluene, etc.), ketones (e.g., acetone, methylethylketone, etc.), nitriles (e.g., acetonitrile, etc.), amides (e.g., dimethylformamide, etc.), water, ethyl acetate, acetic acid or a mixture of at least two of them] in the presence of a hydrogenation catalyst (e.g., palladium-carbon, palladium black, palladium, palladium hydroxide, platinum dioxide, nickel, Raney nickel, ruthenium chloride, etc.) in the presence or in the absence of an acid (e.g., hydrochloric acid, sulfuric acid, hypochlorous acid, boric acid, tetrafluoroboric acid, acetic acid, p-toluenesulfonic acid, oxalic acid, trifluoroacetic acid, formic acid, etc.) under the hydrogen atmosphere at normal pressure or under pressurization, or in the presence of ammonium formate or hydrazine at a temperature of 0 to 200° C.

2) It may be carried out, for example, in a water-miscible solvent (ethanol, methanol, tetrahydrofuran, etc.) in the presence or absence of an acid (hydrochloric acid, hydrobromic acid, ammonium chloride, acetic acid, ammonium formate, etc.) using a metal reagent (zinc, iron, tin, tin chloride, iron chloride, samarium, indium, sodium borohydride-Nickel chloride, etc.) at a temperature of 50 to 150° C.

The compounds represented by formula (II) to (XXIX), used as other staring materials and each reagent, are either known per se or can be produced easily by a known method, for example, a method described in *Comprehensive Organic Transformations: A Guide to Functional Group Preparations,* 2nd Edition (Richard C. Larock, John Wiley & Sons Inc, 1999) or a combination method thereof For example, 3-chloroquinoline-2-amine (CAS No.: 497829-97-7),
6-chloro-2-(methylthio)pyrido[2,3-d]pyrimidine-7-amine (CAS No.: 352329-16-9),
5,6,7,8-tetrahydroquinoline-2,3-diamine (CAS No.: 346735-06-6),
3-chloroisoquinoline-4-amine (CAS No.: 342899-38-1),
5-bromo-6-chloro-1,3-dihydro-2H-pyrrolo[2,3-b]pyridine-2-one (CAS No.: 297757-11-0),
2-chloro-6-methyl-5,6,7,8-tetrahydro-1,6-naphthyridine-3-amine (CAS No.: 216966-50-6),
2,4-dibromo-6,7-dihydro-5H-cyclopenta[b]pyridine-3-amine (CAS No.: 214699-65-7),
2-chloro-7-ethyl-6,7,8,9-tetrahydro-5H-pyrido[2,3-d]azepine-3-amine (CAS No.: 200811-71-8),
5,6-dichloro-2-[(2S)-1-methylpyrrolidin-2-yl]furo[3,2-b]pyridine (CAS No.: 188056-41-9),
3-bromo-5-methyl-1,6-naphthyridine-2-amine (CAS No.: 147293-26-3),
2,3-dichloro-6,7-dihydro-5H-cyclopenta[b]pyridine-4-amine (CAS No.: 142425-91-0),
2-chloro-6,7-dihydro-5H-cyclopenta[b]pyridine-3,4-diamine (CAS No.: 142425-82-9),
2-chloroquinoline-3-amine (CAS No.: 116632-54-3), 6,7-dichloropyrido[2,3-b]pyrazine (CAS No.: 115121-23-8),
1-methoxyisoquinoline-3,4-diamine (CAS No.: 110128-59-1),
4,6,7-trichloro-3-methyl-2,3-dihydrofuro[3,2-c]pyridine (CAS No.: 81706-97-0),
5,7,8-trichloro-3,4-dihydro-2H-pyrano[3,2-c]pyridine (CAS No.: 81706-86-7),
2,3-dichloro-7-phenylthieno[2,3-b]pyrazine (CAS No.: 67718-23-4),
4-chloroisoquinoline-3-amine (CAS No.: 66729-00-8),
5,6-dichloro[1,3]thiazolo[4,5-b]pyrazine (CAS No.: 66490-66-2),
6,7-dichloro-4-methyl-3,4-dihydro-2H-pyrazino[2,3-b][1,4]oxazine (CAS No.: 63880-12-6),
5,6-dichloro-4-methyl-2,3-dihydro-1H-pyrrolo[2,3-b]pyridine (CAS No.: 59558-39-3),
2,3,5,6,8-pentachloroimidazo[1,2-a]pyrazine (CAS No.: 57948-42-2),
1,5-naphthyridine-2,3-diamine (CAS No.: 50786-31-7),
3-bromoisoquinoline-4-amine (CAS No.: 40073-37-8),
2,3-dichloropyrido[3,4-b]pyrazine (CAS No.: 35251-99-1), and
2,3-dichloropyrido[2,3-b]pyrazine (CAS No.: 25710-18-3) are known compound.

In each reaction in the present specification, as apparent to the skilled persons in the art, the reactions involving heating may be carried out using a water bath, an oil bath, a sand bath or a microwave.

In each reaction in the present specification, a solid-supported reagent which is supported on a high molecular polymer (e.g., polystyrene, polyacrylamide, polypropylene, polyethylene glycol, etc.) may be suitably used.

In each reaction in the present specification, the reaction products may be purified by a conventional purification method, for example, by distillation at a normal or reduced pressure, high performance liquid chromatography using silica gel or magnesium silicate, thin layer chromatography, ion-exchange resin, scavenger resin, column chromatography, washing or recrystallization. The purification may be done after each reaction or after several reactions.

In the reactions using a polystyrene resin in the present specification, the reaction products may be purified by a conventional purification method, for example, by washing with a solvent (N,N-dimethylformamide, methylene chloride, methanol, tetrahydrofuran, toluene, acetic acid/toluene, etc.) several times.

Pharmacological Activities:

Pharmacological tests in addition to those described in Experimental Examples include the followings. As shown below, chemokine receptor (especially in CCR4 and/or CCR5) antagonistic activity in vitro of the compound of the present invention can be demonstrated, and also efficacy in vivo can be confirmed.

As a system for screening a CCR4 antagonist, for example, a system for measuring effects for the transient increase of Ca ions induced by mediation of CCR4 ligands other than MDC, for example, TARC, etc. can be conducted since CCR4 is a seven transmembraneous G protein-coupled type receptor. Furthermore, CCR4 antagonistic activity also can be demonstrated by the method described in WO2002/30357, WO2002/30358 or WO2002/94264, or a modification thereof, and these methods can be also used as a screening method. Furthermore, these publications also disclose experimental methods using animals, and therefore according to the methods or a modification thereof, the efficacy of a CCR4 antagonist in vivo model can be confirmed.

And as a system for screening a CCR5 antagonist, for example, the method described in WO2001/40227, WO2002/74770, or a modification thereof can be used. By using these method, the antagonistic activity of the compound can be revealed and these method can be also used as a screening method.

Toxicity:

The toxicity of the compound of the present invention is very low, and it is believed that the compound is safe enough for pharmaceutical use.

Application to Medicaments:

Since the compound of the present invention represented by formula (I) has a chemokine-receptor antagonistic activity in animals including human, especially in human, it is considered that it is useful as a preventive and/or therapeutic agent for a chemokine receptor-mediated disease. The chemokine receptor-mediated disease includes, for example, inflammatory and/or allergic disease [e.g., systemic inflammatory response syndrome (SIRS), anaphylaxis or anaphylactoid reaction, allergic vasculitis, transplant rejection reaction, hepatitis, nephritis, nephropathy, pancreatitis, rhinitis, arthritis, inflammatory ocular disease (e.g., conjunctivitis, etc.), inflammatory bowel disease (e.g., ulcerative colitis, Crohn's disease, eosinophilic gastroenteropathy, etc.), disease in cerebro and/or circulatory system (e.g., arteriosclerosis, thrombosis, ischemic/reperfusion disorder, restenosis, infarction, etc.), respiratory disease (e.g., acute respiratory distress syndrome (ARDS), asthma, pulmonary fibrosis, allergic broncho-pulmonary aspergillosis, etc.), dermatosis (e.g., dermatitis such as atopic dermatitis, psoriasis, contact dermatitis, eczema, urticaria and pruritus, and the like), autoimmune disease (e.g., multiple sclerosis, chronic articular rheumatism, systemic lupus erythematodes, Type I diabetes mellitus, glomerular nephritis, Sjoegren's syndrome, etc.), and the like], metabolism and/or endocrine system disease (e.g., diabetes mellitus, etc.), cancer disease [for example, malignant neoplasm such as leukemia, cancer and cancer metastasis, etc.), and the like], infection [for example, viral disease (e.g., human immunodeficiency virus infection, acquired immunodeficiency syndrome, SARS, etc.), and the like], and the like.

Furthermore, the compound of the present invention represented by formula (I) has an ability to modulate TNFα content in living body, especially in blood, namely, TNFα modulating activity, more specifically TNFα production inhibitory activity. In addition, the compound of the present invention has an ability to inhibit a function of effector cell which expressing chemokine receptor (e.g., cell migration and the like), namely effector cell-function inhibitory activity. Therefore the compound of the present invention is considered to be useful as a preventive and/or therapeutic agent for a disease which is suggested to be mediated by TNFα, and/or a disease which is suggested to be mediated by effector cell, especially the above-described diseases.

The compound represented by formula (I) or a salt thereof may be administered as a combination drug in combination with other drug in order to accomplish the following purposes:

1) to supplement and/or enhance the preventive and/or therapeutic effect of the present compound;
2) to improve the kinetics and/or absorption and reduce the dose of the compound; and/or
3) to eliminate the side effects of the compound.

And also, the compound represented by formula (I) or a salt thereof may be administered as a combination drug in combination with other drug in order to accomplish the following purposes: (1) to supplement and/or enhance the preventive and/or therapeutic effect of the other drug used in combination drug; (2) to improve the kinetics and/or absorption and reduce the dose of the other drug used in combination drug; and/or (3) to eliminate the side effects of the other drug used in combination drug.

A combination drug of the compound represented by formula (I) and other drug may be administered in the form of the formulations having these components incorporated in one preparation, or may be administered in separate preparations. In the case where these drugs are administered in separate preparations, they may be administered simultaneously or at different times. In the latter case, the compound represented by formula (I) may be administered before the other drug. Alternatively, the other drug may be administered before the compound represented by formula (I). The method for the administration of these drugs may be the same or different.

The diseases on which the preventive and/or therapeutic effect of the above-mentioned combination drug works are not specifically limited but may be those for which the preventive and/or therapeutic effect of the compound represented by formula (I) is supplemented and/or enhanced.

The weight ratio of the compound represented by formula (I) and the other drug is not specifically limited.

As other drug, two or more drugs may be administered with the compound of the present invention.

Furthermore, the other drug for supplementing and/or enhancing the preventive and/or therapeutic effect of the compound represented by formula (I) includes not only those found so far but also those which will be found on the basis of the above mentioned mechanism.

Examples of other drugs for supplementing and/or enhancing the preventive and/or therapeutic effect of the compounds represented by formula (I) on atopic dermatitis include, for example, steroids, nonsteroidal anti-inflammatory drugs (NSAID), immunosuppressants, prostaglandins, antiallergic drugs, mediator release inhibitors, antihistamines, metabolism promoters (forskolin preparations, etc.), phosphodiesterase inhibitors, chemokine inhibitors, and the like.

Examples of other drugs for supplementing and/or enhancing the preventive and/or therapeutic effect of the compounds represented by formula (I) on allergic conjunctivitis include, for example, leukotriene receptor antagonists, antihistamines, mediator release inhibitors, nonsteroidal anti-inflammatory drugs, prostaglandins, steroids, nitric oxide synthase inhibitors, chemokine inhibitors, and the like.

Examples of other drug for supplementing and/or enhancing the preventive and/or therapeutic effect of the compounds represented by formula (I) on allergic rhinitis include, for example, antihistamines, mediator release inhibitors, thromboxane synthase inhibitors, thromboxane A2 receptor antagonists, leukotriene receptor antagonists, steroids, α-adrenaline receptor stimulants, xanthine derivatives, anticholinergic agents, prostaglandins, nitric oxide synthase inhibitors, β2-adrenaline receptor stimulants, phosphodiesterase inhibitors, chemokine inhibitors, and the like.

Examples of other drug for supplementing and/or enhancing the preventive and/or therapeutic effect of the compounds represented by formula (I) on asthma include, for example, bronchodilators (β2-adrenaline receptor stimulants, xanthine derivatives, anticholinergic agents, etc.), antiinflammatory agents (steroids, nonsteroidal anti-inflammatory drugs (NSAID), etc.), prostaglandins, leukotriene receptor antagonists, phosphodiesterase inhibitors, chemokine inhibitors, Chinese herbal medicines, and the like.

Examples of other drug for supplementing and/or enhancing the preventive and/or therapeutic effect of the compounds represented by formula (I) on HIV infection or AIDS include, for example, reverse transcriptase inhibitors, protease inhibitors, chemokine inhibitors (e.g., CCR1 antagonists, CCR2 antagonists, CCR3 antagonists, CCR4 antagonists, CCR5 antagonists, CXCR4 antagonists, and the like), fusion inhibitors, integrase inhibitor, antibodies against cell surface antigen of HIV-1, vaccine for HIV-1, and the like.

Examples of other drug for supplementing and/or enhancing the preventive and/or therapeutic effect of the compounds represented by formula (I) on transplant rejection reaction include, for example, immunosuppressants, and the like.

Examples of other drug for supplementing and/or enhancing the preventive and/or therapeutic effect of the compounds represented by formula (I) on multiple sclerosis include, for example, steroids, interferon, immunosuppressants, chemokine inhibitors, aldose reductase inhibitors, cannabinoid-2 receptor stimulants, adrenocorticotropic hormone, and the like.

Examples of other drug for supplementing and/or enhancing the preventive and/or therapeutic effect of the compounds represented by formula (I) on rheumatoid arthritis include, for example, metalloproteinase inhibitors, immunosuppressants, chemokine inhibitors, non-steroidal anti-inflammatory drugs (NSAID), steroids, prostaglandins, phosphodiesterase inhibitors, cannabinoid receptor-2 stimulants, disease modifying anti-rheumatic drugs, antiinflammatory enzyme preparations, cartilage protectant, T-cell function suppressor, TNFα inhibitor, IL-1 inhibitor, IL-6 inhibitor, interferon-γ activator, NF-κB inhibitor, and the like.

Regarding the steroids, in the case of external preparations, examples include, for example, clobetasol propionate, diflorasone diacetate, fluocinonide, mometasone furoate, betamethasone dipropionate, betamethasone butyrate propionate, betamethasone valerate, difluprednate, butesonid, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone dipropionate, clobetasone butyrate, prednisolone, beclometasone dipropionate, fludroxycortide, and the like.

Examples of internal medicines and injections include, for example, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethason acetate, betamethasone, and the like.

Examples of inhalations include, for example, beclometasone dipropionate, fluticasone propionate, budesonide, flunisolide, triamcinolone, ST-126P, ciclesonide, dexamethasone palmitate, mometasone furoate, prasterone sulfonate, deflazacort, methylprednisolone suleptanate, methylprednisolone sodium succinate, and the like.

Examples of nonsteroidal anti-inflammatory drugs include, for example, sasapyrine, sodium salicylate, aspirin, aspirin.di-aluminate composition, diflunisal, indometacin, suprofen, ufenamate, dimethyl isopropylazulene, bufexamac, felbinac, diclofenac, tolmetin sodium, Clinoril, fenbufen, nabumetone, proglumetacin, indometacin farnesil, acemetacin, proglumetacin maleate, amfenac sodium, mofezolac, etodolac, ibuprofen, ibuprofen piconol, naproxen, flurbiprofen, flurbiprofenaxetil, ketoprofen, fenoprofen calcium, thiaprofen, oxaprozin, pranoprofen, loxoprofen sodium, alminoprofen, zaltoprofen, mefenamic acid, aluminum mefenamate, tolfenamic acid, floctafenine, ketophenylbutazon, oxyphenbutasone, piroxicam, tenoxicam, ampiroxicam, Napageln ointment, epirizole, tiaramide hydrochloride, tinoridine hydrochloride, emorfazone, sulpyrine, migrenin, Saridon, Sedes-G, Amipylo-N, Sorbon, pyrine preparation for cold syndrome, acetaminophen, phenacetin, dimetotiazine mesilate, simetride composition, non-pyrine preparation for cold syndrome, and the like.

Examples of immunosuppressant include, for example, Protopic (FK-506), methotrexate, cyclosporine, ascomycin, leflunomide, bucillamine, salazosulfapyridine, sirolimus, mycophenolate mofetil, and the like.

Examples of prostaglandins (hereinafter, abbreviated to PG) include PG receptor agonist, PG receptor antagonist, and the like.

Examples of PG receptor include PGE receptor (EP1, EP2, EP3, EP4), PGD receptor (DP, CRTH2), PGF receptor (FP), PGI receptor (IP), TX receptor (TP), and the like.

Examples of mediator release inhibitor include, for example, tranilast, sodium cromoglicate, amlexanox, repirinast, ibudilast, tazanolast, pemirolast potassium, and the like.

Examples of antihistaminics include, for example, ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine, famotidine, ranitidine, cimetidine, and the like.

Examples of phosphodiesterase inhibitor include, for example, the PDE4 inhibitors such as rolipram, cilomilast (trade name: ariflo), Bay19-8004, NIK-616, roflumilast (BY-217), cipamphylline (BRL-61063), atizoram (CP-80633), SCH-351591, YM-976, V-11294A, PD-168787, D-4396, IC-485, and the like.

Examples of leukotriene receptor antagonist include, for example, pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057, and the like.

Examples of thromboxane A2 receptor antagonist include, for example, seratrodast, ramatroban, domitroban calcium hydrate, KT-2-962, and the like.

Examples of thromboxane synthase inhibitor include, for example, ozagrel hydrochloride, imitrodast sodium, and the like.

Examples of xanthine derivatives include, for example, aminophylline, theophylline, doxophylline, cipamphylline, diprophylline, and the like.

Examples of anticholinergic agent include, for example, ipratropium bromide, oxitropium bromide, flutropium bromide, cimetropium bromide, temiverine, tiotropium bromide, revatropate (UK-112166), oxybutynin hydrochloride, bethanechol chloride, propiverine hydrochloride, propantheline bromide, methylbenactyzium bromide, scopolamine butylbromide, tolterodine tartrate, trospium chloride, Z-338, UK-112166-04, KRP-197, darifenacin, YM-905, mepenzolate bromide, ipratropium bromide, and the like.

Examples of β2-adrenaline receptor stimulant include, for example, fenoterol hydrobromide, salbutamol sulfate, terbutaline sulfate, formoterol fumarate, salmeterol xinafoate, isoproterenol sulfate, orciprenaline sulfate, chlorprenaline sulfate, epinephrine, trimetoquinol hydrochloride, hexoprenalinemesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-formoterol, KUR-1246, KUL-7211, AR-C89855, S-1319, and the like.

Examples of Chinese herbal medicine include, for example, Shoseiryu-to, Mao-to, Bakumonto-to, and the like.

Examples of reverse transcriptase inhibitor include, in concrete terms, (1) nucleic-acid reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil), PMPA (brand name: Tenofovir), and the like, (2) nonnucleic-acid reverse transcriptase inhibitors: nevirapine (brand name: Viramune), delavirdine (brand name: Rescriptor), efavirenz (brand name: Sustiva, Stocklin), capravirine (AG1549), and the like.

Examples of protease inhibitor include, in concrete terms, indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra), tipranavir, and the like.

As chemokine antagonists, internal ligands of chemokine receptor, its derivatives, non-peptide low molecular compounds or antibodies of chemokine receptor are included.

Examples of internal ligand of chemokine receptor include, in concrete terms, MIP-1α, MIP-1β, RANTES, SDF-1α, SDF-1β, MCP-1, MCP-2, MCP-4, Eotaxin, MDC, and the like.

Examples of the derivatives of internal ligand include, in concrete terms, AOP-RANTES, Met-SDF-1α, Met-SDF-1β, and the like.

Examples of antibodies of chemokine receptor include, in concrete terms, Pro-140, and the like.

Examples of CCR1 antagonist include, in concrete terms, the compounds disclosed in the specification of WO98/04554, WO98/38167, WO99/40061, WO00/14086, WO00/14089, WO01/72728, JP2002-179676, WO02/036581, WO03/013656, WO03/035627, WO03/035037, or BX-471, and the like.

Examples of CCR2 antagonist include, in concrete terms, the compounds disclosed in the specification of WO99/07351, WO99/40913, WO00/46195, WO00/46196, WO00/46197, WO00/46198, WO00/46199, WO00/69432, WO00/69815 or the compounds disclosed in Bioorg. Med. Chem. Lett., 10, 1803 (2000), and the like.

Examples of CCR3 antagonist include, in concrete terms, the compounds disclosed in the specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327, WO01/09088, and the like.

Examples of CCR4 antagonist include, in concrete terms, the compounds disclosed in the specification of WO02/030357, WO02/030358, WO02/094264, WO03/051870, WO03/059893, and the like.

Examples of CCR5 antagonist include, in concrete terms, the compounds disclosed in the specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO00/59503, WO00/76933, WO98/25605, WO99/04794, WO99/38514, or the compounds disclosed in *Bioorg. Med. Chem. Lett.*, 10, 1803 (2000), or TAK-779, SCH-351125 (SCH-C), SCH-417690 (SCH-D), UK-427857, GW 873140A, TAK-220, and the like.

Examples of CXCR4 antagonist include, in concrete terms, AMD-3100, T-22, KRH-1120 or the compounds disclosed in the specification of WO00/66112, and the like.

Examples of fusion inhibitor include, in concrete terms, T-20 (pentafuside), T-1249, and the like.

Examples of integrase inhibitor include, in concretely terms, Equisetin, Temacrazine, PL-2500, V-165, NSC-618929, L-870810, L-708906 analog, S-1360, 1838, and the like.

The drug described hereinbefore is merely example, so the combination drug of the present invention does not limited thereto.

The typical examples of the usual dosage in clinical trials of reverse transcriptase inhibitors or protease inhibitors written below are intended to illustrate the present invention, but do not limit them.

| | |
|---|---|
| Zidovudine: | 100 mg capsule, 200 mg per dose, 3 times per day; 300 mg tablet, 300 mg per dose, twice per day; |
| didanosine: | 25-200 mg tablet, 125-200 mg per dose, twice per day; |
| zalcitabine: | 0.375-0.75 mg tablet, 0.75 mg per dose, 3 times per day; |
| stavudine: | 15-40 mg capsule, 30-40 mg per dose, twice per day; |
| lamivudine: | 150 mg tablet, 150 mg per dose, twice per day; |
| abacavir: | 300 mg tablet, 300 mg per dose, twice per day; |
| nevirapine: | 200 mg tablet, 200 mg per dose, once per day for 14 days and then twice per day; |
| delavirdine: | 100 mg tablet, 400 mg per dose, 3 times per day; |
| efavirenz: | 50-200 mg capsule, 600 mg per dose, once per day; |
| indinavir: | 200-400 mg capsule, 800 mg per dose, 3 times per day; |
| ritonavir: | 100 mg capsule, 600 mg per dose, twice per day; |
| nelfinavir: | 250 mg tablet, 750 mg per dose, 3 times per day; |
| saquinavir: | 200 mg capsule, 1200 mg per dose, 3 times per day; |
| amprenavir: | 50-150 mg tablet, 1200 mg per dose, twice per day. |

Examples of disease-modifying anti-rheumatic drugs include, in concrete terms, aurothioglucose, gold sodium thiomalate, auranofin, actarit, D-penicillamine, lobenzarit disodium, bucillamine, hydroxychloroquine, salazosulfapyridine, and the like.

Examples of antiinflammatory enzyme preparations include, in concrete terms, lysozyme hydrochloride, bromelain, pronase, serrapeptase, combination drug of streptokinase-streptodornase, and the like.

Examples of cartilage protectant include, in concrete terms, sodium hyaluronate, glucosamine, chondroitin sulfate, glycosaminoglycan polysulfate, and the like.

Mass ratio of "the compound represented by formula (I)" and other drug is not particularly limited. The other drug may be administered as a combination of optional two or more species. In addition, not only those which have so far been found but also will be found based on the above-described mechanism are included in other drug which complement and/or reinforce the preventive and/or therapeutic effect of "the compound represented by formula (I)".

The compound of the present invention represented by formula (I) is safe and low-toxic, thus can be administered to human and mammals other than human (e.g., rat, mouse, rabbit, sheep, swine, bovine, cat, dog, monkey, etc.).

For the purpose above described, the compounds represented by formula (I), pharmacologically acceptable salts thereof, acid addition salts or hydrates thereof, or a combination of the compounds represented by formula (I) and other drugs may be normally administered systemically or locally, usually by oral or parenteral administration.

The doses to be administered are determined depending upon, for example, ages, body weights, symptoms, the desired therapeutic effects, the route of administration and the duration of the treatment. For the human adult, the doses per person are generally from 1 ng to 100 mg, by oral administration, up to several times per day, and from 0.1 ng to 10 mg, by parenteral administration, up to several times per day, or continuous administration 1 to 24 hours per day from vein.

As mentioned above, the doses to be used depend upon various conditions. Therefore, there are cases in which doses lower than or greater than the ranges specified above may be used.

To administer the compounds of the present invention represented by formula (I) or a combination of the compounds represented by formula (I) and other drugs, use is made of solid preparations for internal use and liquid preparations for internal use for oral administration as well as preparations for injections, external preparations, suppositories, eye drops, nasal drops, inhalations and the like for parenteral administration.

Examples of the solid preparations for internal use for oral administration include tablets, pills, capsules, powders, granules and the like. The capsules include hard capsules and soft capsules.

Such a solid preparation for internal use is prepared by a formulation method commonly employed by using one or two or more active substances either as it is or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

The liquid preparations for internal use for oral administration include pharmaceutically acceptable aqueous solutions, suspensions, emulsions, syrups, elixirs and the like. Such a liquid preparation is prepared by dissolving, suspending or emulsifying one or more active substance(s) in a diluent commonly employed (purified water, ethanol or a mixture thereof, etc.). Such liquid forms may also further comprise some additives such as humectants, suspending agents, emulsifying agents, sweetening agents, flavoring agents, aroma, preservatives, buffers and the like.

The dosage forms of the parenteral administration preparations for external use include ointments, gels, creams, fomentations, patches, liniments, atomized agents, inhalations, sprays, aerosols, eye drops, nasal drops and the like. Such a preparation contains one or two or more active substance(s) and is prepared by a well known method or a commonly employed formulation.

Ointments are prepared in accordance with a well known formulation or a commonly employed formulation. For Example, they are prepared by softening or melting one or two or more active substance(s) in a base. The ointment base is selected from well known ones or those commonly employed. For Example, use may be made of one base or a mixture of two or more thereof selected from higher fatty acids or higher fatty acid esters (adipic acid, myristic acid, palmitic acid, stearic acid, oleic acid, adipic acid esters, myristic acid esters, palmitic acid esters, stearic acid esters, oleic acid esters, etc.), waxes (beeswax, whale wax, ceresin, etc.), surfactants (polyoxyethylene alkyl ether phosphoric acid esters, etc.), higher alcohols (cetanol, stearyl alcohol, cetostearyl alcohol, etc.), silicone oils (dimethylpolysiloxane, etc.), hydrocarbons (hydrophilic vaseline, white vaseline, refined lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, yolk oil, squalane, squalene, etc.), water, absorption promoters and skin irritation inhibitors. The ointments may further contain a humectant, a preservative, a stabilizer, an antioxidant, a flavor, and the like.

Gels are prepared in accordance with a well known formulation or a formulation commonly employed. For Example, they are prepared by melting one or more active substance(s) in a base. The gel base is selected from well known ones or those commonly employed. For Example, use may be made of one base or a mixture of two or more thereof selected from lower alcohols (ethanol, isopropyl alcohol, etc.), gelling agents (carboxymethylcellulose, hydroxyethylcellulose, hydroxypropylcellulose, ethylcellulose, etc.), neutralizing agents (triethanolamine, diisopropanolamine, etc.), surfactants (polyethylene glycol monostearate, etc.), gums, water, absorption promoters and skin irritation inhibitors. The gels may further contain a preservative, an antioxidant, a flavor, and the like.

Creams are prepared in accordance with a well known formulation or a formulation commonly employed. For Example, they are prepared by melting or emulsifying one or more active substance(s) in a base. The cream base is selected from well known ones or those commonly employed. For Example, use may be made of one base or a mixture of two or more thereof selected from higher fatty acid esters, lower alcohols, hydrocarbons, polyhydric alcohols (propylene glycol, 1,3-butylene glycol, etc.), higher alcohols (2-hexyldecanol, cetanol, etc.), emulsifiers (polyoxyethylene alkyl ethers, fatty acid esters, etc.), water, absorption promoters and skin irritation inhibitors. The creams may further contain a preservative, an antioxidant, a flavor, and the like.

Fomentations are prepared in accordance with a well known formulation or a formulation commonly employed. For Example, they are prepared by melting one or more active substance(s) in a base, kneading and then applying and spreading the kneaded matter on a substrate. The fomentation base is selected from well known ones or those commonly employed. For Example, use may be made of one base or a mixture of two or more thereof selected from thickeners (polyacrylic acid, polyvinylpyrrolidone, gum acacia, starch, gelatin, methylcellulose, etc.), moistening agents (urea, glycerin, propylene glycol, etc.), fillers (kaolin, zinc oxide, talc, calcium, magnesium, etc.), water, dissolution aids, tackifiers and skin irritation inhibitors. The fomentations may further contain a preservative, an antioxidant, a flavor, and the like.

Patches are prepared in accordance with a well known formulation or a formulation commonly employed. For Example, they are prepared by melting one or more active substance(s) in a base and then applying and spreading on a substrate. The patch base is selected from well known ones or those commonly employed. For Example, use may be made of one base or a mixture of two or more thereof selected from polymer bases, fats and oils, higher fatty acids, tackifiers and skin irritation inhibitors. The patches may further contain a preservative, an antioxidant, a flavor, and the like.

Liniments are prepared in accordance with a well known formulation or a formulation commonly employed. For Example, they are prepared by dissolving, suspending or emulsifying one or two or more active substance(s) in one or more media selected from water, alcohols (ethanol, polyethylene glycol, etc.), higher fatty acids, glycerin, soap, emulsifiers, suspending agents, and the like. The liniments may further contain a preservative, an antioxidant, a flavor, and the like.

Atomized agents, inhalations and sprays may contain, in addition to a diluent commonly employed, a stabilizer such as sodium hydrogen sulfite, a buffering agent for imparting isotonicity, for example, an isotonic agent such as sodium chloride, sodium citrate or citric acid. Methods for producing a spray are described in detail in, for example, U.S. Pat. No. 2,868,691 and U.S. Pat. No. 3,095,355.

The injections for parenteral administration include all forms of injections and also drops, for example, an intramuscular injection, a subcutaneous injection, an intradermal injection, an intraarterial injection, an intravenous injection, a peritoneal injection, an intrathecal injection, an intravenous drop, and the like.

The injections for parenteral administration include solutions, suspensions, emulsions and solid injections to be dissolved or suspended before use. Such an injection is used by dissolving, suspending or emulsifying one or more active substance(s) in a solvent. The solvent includes, for example, distilled water for injection, physiological saline, vegetable oils, alcohols such as propylene glycol, polyethylene glycol and ethanol, and mixtures thereof. The injection may further contain a stabilizer, a dissolution aid (glutamic acid, aspartic acid, Polysorbate 80 (registered trademark), etc.), a suspending agent, an emulsifier, a soothing agent, a buffer, a preservative, and the like. Such an injection may be produced by sterilizing at the final step or employing an aseptic process. Alternatively, it is also possible that an aseptic solid product such as a freeze-dried product is produced and sterilized or dissolved in aseptic distilled water for injection or another solvent before use.

Eye drops for parenteral administration may be in the form of liquid, suspension, emulsion, liquid dissolved in a solvent in use or ointment.

These eye drops are prepared by any known method. For Example, one or more active substance(s) are dissolved, suspended or emulsified in a solvent. As such a solvent for eye drops, there may be used sterilized purified water, physiological saline and other aqueous solvents or non-aqueous solvents for injection (e.g., vegetable oils, etc.), singly or in combination thereof The eye drops may contain ones selected from an isotonic agent (e.g., sodium chloride, concentrated glycerin, etc.), a buffering agent (e.g., sodium phosphate, sodium acetate, etc.), a surfactant (e.g., Polysolvate 80 (trade name), Polyoxyl stearate 40, polyoxyethylene-hydrogenated castor oil, etc.), a stabilizer (sodium citrate, sodium edetate, etc.), a preservative (e.g., benzalconium chloride, paraben, etc.), and the like. The eye drops are sterilized at the final step or prepared by an aseptic process. Alternatively, an aseptic solid agent such as freeze-dried product which has previously been prepared may be rendered aseptic or dissolved in aseptic distilled water for injection or other solvent before use.

The inhalations for parenteral administration include aerosols, powders for inhalation and liquids for inhalation. Such inhalations may be dissolved or suspended in water or another adequate medium for use.

The inhalations may be prepared in accordance with a well known method.

For Example, liquid preparations for inhalation may be, if necessary, prepared by appropriately selecting a preservative (benzalkonium chloride, paraben, etc.), a colorant, a buffering agent (sodium phosphate, sodium acetate, etc.), an isotonic agent (sodium chloride, concentrated glycerin, etc.), a thickener (carboxyvinyl polymer, etc.), an absorption promoter, and the like.

Powders for inhalation may be prepared, if necessary, by appropriately selecting a lubricant (stearic acid and its salt, etc.), a binder (starch, dextrin, etc.), an excipient (lactose, cellulose, etc.), a colorant, a preservative (benzalkonium chloride, paraben, etc.), an absorption promoter, and the like.

When the liquids for inhalation are administered, a sprayer (atomizer, nebulizer) is usually used. When the powders for inhalation are used, an inhalation administration apparatus for powder agents is usually used.

Other compositions for parenteral administration include suppositories and pessaries for vaginal administration which contain one or more active substance(s), and are prepared in accordance with common formulations.

The compounds of the present invention are designated as follows.

The name of the compounds used in the present specification is designated according to IUPAC regulations, or using a computer program conducting designation generally according to IUPAC regulations, ACD/Name (registered trademark, version 6.00, Advanced Chemistry Development Inc.). For example, the compound, wherein ring A is phenyl; J is —O—CH$_2$—; ring D is 5-bromo-2,3-substituted pyridine ring; G is —NHSO$_2$—; and ring B is 4-methylphenyl, that is, the compound represented by the following formula:

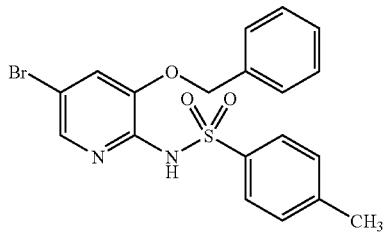

was named N-[3-(benzyloxy)-5-bromopyridin-2-yl]-4-methylbenzenesulfonamide.

Effect of the Invention

The compound of the present invention represented by formula (I) has a chemokine-receptor (especially CCR4 and/or CCR5) antagonistic activity, it is useful as a preventive and/or therapeutic agent for a disease which is mediated by chemokine receptor, namely chemokine receptor-mediated disease. And also, the compound of the present invention antagonizes chemokine receptor strongly in the presence of protein.

BEST MODE FOR CARRYING OUT THE INVENTION

The present invention is explained below in detail based on Reference Examples and Examples, but the present invention is not limited thereto.

The solvents in the parentheses show the eluting or developing solvents in chromatographic separations or TLC and the ratios of the solvents used are by volume.

The value of NMR is a measurement of 1H NMR at 300 MHz. The solvents in the parentheses in NMR show the solvents for measurement.

Example 1

N-[5-bromo-3-hydroxypyridin-2-yl]-4-methylbenzenesulfonamide

With 4-methylbenzenesulfonyl chloride, 6-bromo-[1,3]-oxazolo[4,5-b]pyridin-2(3H)-one (described in *Heterocycles*, 41, 2799 (1995)) was allowed to react. Then, with an aqueous solution of sodium hydroxide, the mixture was hydrolyzed to give the title compound having the following physical data.

TLC: Rf 0.44 (hexane:ethyl acetate=1:1);
NMR (d$_6$-DMSO): δ 2.35, 7.21, 7.34, 7.69, 7.83, 10.10, 10.75.

Example 2

N-[3-(benzyloxy)-5-bromopyridin-2-yl]-4-methylbenzenesulfonamide

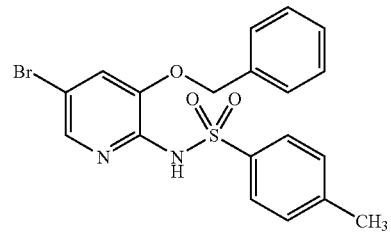

To a solution of the compound prepared in Example 1 (468 mg) in tetrahydrofuran (10 mL), benzyl alcohol (0.16 mL) and triphenylphosphine (396 mg) were added. To the mixture, 40% diethyl azodicarboxylate (657 mg) was added at room temperature. The reaction mixture was stirred for 4.5 hours at room temperature. The reaction mixture was concentrated. To the obtained residue, methyl t-butyl ether was added, solidified, filtrated and dried up to give the compound of the present invention (154 mg) having the following physical data.

TLC: Rf 0.36 (hexane:ethyl acetate=4:1);
NMR (CDCl$_3$): δ 2.41, 5.04, 7.20, 7.28, 7.36, 7.43, 7.53, 7.89, 8.00.

Example 2(1) and 2(2)

The following compounds of the present invention were obtained, using a corresponding alcohol derivative instead of benzyl alcohol, by the same procedure as a series of reactions of Example 2.

Example 2(1)

N-[5-bromo-3-(pyridin-3-ylmethoxy)pyridin-2-yl]-4-methylbenzenesulfonamide

TLC: Rf 0.62 (ethyl acetate);

NMR ($d_6$-DMSO): δ 2.34, 5.22, 7.33, 7.45, 7.70, 7.83, 7.93, 8.57, 8.75, 10.48.

Example 2(2)

N-[5-bromo-3-({3-[2-(dimethylamino)ethoxy]-4-methoxybenzyl}oxy)pyridin-2-yl]-4-methylbenzenesulfonamide Physical property: amorphous;

TLC: Rf 0.60 (chloroform:methanol=9:1);

NMR ($d_6$-DMSO): δ 2.26, 2.33, 2.68, 3.74, 4.04, 5.09, 6.95, 7.03, 7.17, 7.30, 7.56, 7.74, 7.81.

Example 3

N-[3-(benzylamino)-5-(trifluoromethyl)pyridin-2-yl]-4-methylbenzenesulfonamide

To a solution of N-[3-amino-5-(trifluoromethyl)pyridin-2-yl]-4-methylbenzenesulfonamide (prepared by the same procedure described in *Chem. Pharm. Bull.*, 43, 1696 (1995)) (100 mg) in dimethylformamide (2 mL), benzaldehyde (134 μL) and acetate (1 mL) were added. To the mixture, sodium triacetoxy borohydride (384 mg) was added at room temperature. The reaction mixture was stirred for overnight at room temperature. To the reaction mixture, water was added and extracted with ethyl acetate. The extract was washed with water, dried with anhydrous magnesium sulfate and concentrated. The obtained residue was purified by column chromatography on silica gel (hexane:ethyl acetate=4:1→2:1). The purified product was washed with ether and filtrated. The obtained solid was washed with methanol, filtrated and dried to give the compound of the present invention (25 mg) having the following physical data.

TLC: Rf 0.70 (hexane:ethyl acetate=2:1);

NMR ($d_6$-DMSO): δ 2.35, 4.40, 6.49, 6.68, 7.33, 7.84, 12.40.

Example 3(1)-3(3)

The following compounds were obtained, using a corresponding aldehyde derivative instead of benzaldehyde, by the same procedure as a series of reactions of Example 3.

Example 3(1)

N-[3-[(3,4-dimethoxybenzyl)amino]-5-(trifluoromethyl)pyridin-2-yl]-4-methylbenzenesulfonamide TLC: Rf0.68 (hexane:ethyl acetate=1:1);

NMR ($d_6$-DMSO): δ 2.35, 3.67, 3.69, 4.29, 6.54, 6.85, 6.95, 7.33, 7.45, 7.82.

Example 3(2)

4-methyl-N-[3-[(pyridin-3-ylmethyl)amino]-5-(trifluoromethyl)pyridin-2-yl]benzenesulfonamide TLC: Rf 0.27 (hexane:ethyl acetate=1:1);

NMR ($d_6$-DMSO): δ 2.35, 4.45, 6.65, 7.33, 7.47, 7.69, 7.83, 8.43, 8.54.

Example 3(3)

N-[3-({3-[2-(dimethylamino)ethoxy]-4-methoxybenzyl}amino)-5-(trifluoromethyl)pyridin-2-yl]-4-methylbenzenesulfonamide TLC: Rf 0.40 (chloroform:methanol:aqueous ammonia=80:10:1);

NMR ($d_6$-DMSO): δ 2.32, 2.65, 3.20, 3.73, 4.16, 4.26, 6.21, 6.54, 6.92, 7.04, 7.27, 7.43, 7.79.

Example 4

N-[2-{[(4-methylphenyl)sulfonyl]amino}-5-(trifluoromethyl)pyridin-3-yl]benzamide To a solution of N-[3-amino-5-(trifluoromethyl)pyridin-2-yl]-4-methylbenzenesulfonamide (109 mg) in tetrahydrofuran (1 mL) and pyridine (1 mL), benzoyl chloride (50 μL) was added at room temperature. The reaction mixture was stirred for 3 hours at room temperature. To the reaction mixture, water was added and extracted with ethyl acetate. The extract was washed with water, dried with anhydrous magnesium sulfate and concentrated. The obtained residue was solidified by ethyl acetate:ether=1:2, filtrated and dried to give the compound of the present invention (81 mg) having the following physical data.

TLC: Rf 0.36 (hexane:ethyl acetate=2:1);

NMR ($d_6$-DMSO): δ 2.36, 7.38, 7.60, 7.90, 7.98, 8.29, 9.88, 11.31.

Example 4(1)

3,4-dimethoxy-N-[2-{[(4-methylphenyl)sulfonyl]amino}-5-(trifluoromethyl)pyridin-3-yl]benzamide The compound having the following physical data was obtained, using 3,4-dimethoxybenzyl chloride instead of benzyl chloride, by the same procedure as a series of reactions of Example 4.

TLC: Rf 0.42 (hexane:ethyl acetate=1:1);

NMR ($d_6$-DMSO): δ 2.36, 3.82, 3.85, 7.14, 7.37, 7.53, 7.89, 8.27, 9.76.

Example 5

N-(3-bromo-5-methylpyrazin-2-ly)-3-chloro-2-methylbenzenesulfonamide

The title compound having the following physical data was obtained, by subjecting 3-bromo-5-methylpyrazin-2-amine and 3-chloro-2-methylbenzenesulfonyl chloride to sulfonamide reaction.

TLC: Rf 0.58 (hexane:ethyl acetate=1:1);

NMR ($d_6$-DMSO): δ 2.36, 2.66, 7.41, 7.72, 7.91, 8.08, 11.29.

Example 6

3-chloro-N-[3-({4-chloro-3-[(1-methylpiperidin-4-yl)methoxy]benzyl}oxy)-5-methylpyrazin-2-yl]-2-methylbenzenesulfonamide

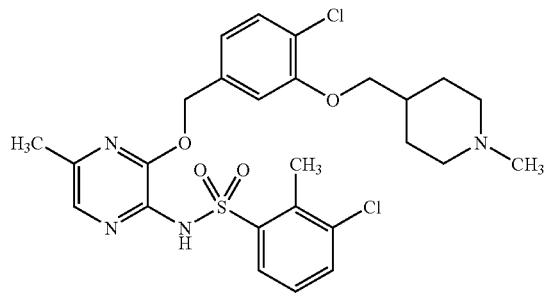

To a solution of {4-chloro-3-[(1-methylpiperidin-4-yl)methoxy]phenyl}methanol (86 mg) in dioxane (1 mL), 60% sodium hydride (27 mg) was added at room temperature. The mixture was stirred for 1 hour at room temperature. To the mixture, a solution of the compound prepared in Example 5 (100 mg) in 1,4-dioxane (1 mL) was added. The reaction mixture was stirred for 2 hours at 90° C. To the reaction mixture, water was added and extracted with ethyl acetate. The extract was washed with water and a saturated aqueous solution of sodium chloride in sequence, dried with anhydrous magnesium sulfate and concentrated. To the obtained residue, ethyl acetate was added, washed by sonication, filtrated and dried to the compound of the present invention (76 mg) having the following physical data. physical property: powder;

TLC: Rf 0.44 (chloroform:methanol=10:1);

NMR ($d_6$-DMSO): δ 1.61, 1.97, 2.26, 2.62, 2.73, 2.96, 3.36, 3.95, 5.34, 7.08, 7.30, 7.38, 7.42, 7.58, 7.68, 7.93.

Example 6(1) and 6(2)

The following compounds of the present invention were obtained, using 3-chloro-2-methylbenzenesulfonyl chloride or 2-chlorobenzenesulfonyl chloride, and {4-chloro-3-[(1-methylpiperidin-4-yl)methoxy]phenyl}methanol or quinolin-2-yl methanol by the same procedure as a series of reactions of Example 5→Example 6.

Example 6(1)

2-chloro-N-[3-({4-chloro-3-[(1-methylpiperidin-4-yl)methoxy]benzyl}oxy)-5-methylpyrazin-2-yl]-2-methylbenzenesulfonamide Physical property: powder;

TLC: Rf 0.17 (chloroform:methanol=10:1);

NMR ($d_6$-DMSO): δ 1.61, 1.98, 2.26, 2.73, 2.96, 3.33, 3.96, 5.34, 7.09, 7.30, 7.42, 7.50, 7.58, 7.60, 8.05.

Example 6(2)

3-chloro-2-methyl-N-[5-methyl-3-(quinolin-2-ylmethoxy)pyrazin-2-yl]benzenesulfonamide Physical property: powder;

TLC: Rf 0.69 (hexane:ethyl acetate=1:1);

NMR ($d_6$-DMSO): δ 2.22, 2.65, 5.62, 7.37, 7.69, 7.98, 8.41, 11.20.

Example 7

2-chloro-N-(3-chloroquinoxalin-2-yl)benzenesulfonamide

In the presence of potassium carbonate (625 mg), 2,3-dichloroquinoxaline (275 mg) and 2-chlorobenzenesulfonamide (264 mg) were allowed to react in the solution of dimethylformamide (4 mL) for 3 hours at 90° C. To the reaction mixture, water and hydrochloric acid were added and extracted with ethyl acetate. The residue was washed with a saturated aqueous solution of sodium chloride, dried with anhydrous magnesium sulfate and concentrated to obtain the title compound (493 mg) having the following physical data.

TLC: Rf 0.58 (hexane:ethyl acetate=1:1);

NMR ($d_6$-DMSO): δ 7.64, 8.27.

Example 8

2-chloro-N-[3-({3-[2-(dimethylamino)ethoxy]-4-methoxybenzyl}oxy)quinoxalin-2-yl]benzenesulfonamide

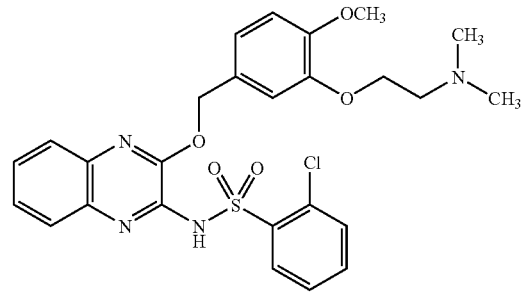

The compound of the present invention having the following physical data was obtained, using the compound prepared in Example 7 and {3-[2-(dimethylamino)ethoxy]-4-methoxyphenyl}methanol by the same procedure as a series of reactions of Example 6.

Physical property: powder;

TLC: Rf 0.55 (chloroform:methanol=9:1);

NMR ($d_6$-DMSO): δ 2.82, 3.41, 3.78, 4.28, 5.34, 7.03, 7.15, 7.35, 8.21.

Example 9

3-nitro-2-(pyridin-3-ylmethoxy)-5-(trifluoromethyl)pyridine

The title compound having the following physical data was obtained, using 3-amino-5-(trifluoromethyl)pyridin-2-ol instead of the compound prepared in Example 1, and pyridin- 3-ylmethanol instead of benzyl alcohol by the same procedure as a series of reactions of Example 2.

TLC: Rf 0.43 (chloroform:methanol=10:1);
NMR (d$_6$-DMSO): δ 5.29, 7.39, 7.80, 8.51, 8.65, 8.71, 9.14.

Example 10

2-(pyridin-3-ylmethoxy)-5-(trifluoromethyl)pyridin-3-amine

To a mixed solution of the compound prepared in Example 10 (199 mg) in ethanol (4 mL) and water (2 mL), hydrosulfite sodium (927 mg) was added at 50° C. The reaction mixture was stirred for 30 minutes at 50° C. To the reaction mixture, water was added and extracted with ethyl acetate. The extract was washed with a saturated aqueous solution of sodium chloride, dried with anhydrous magnesium sulfate and concentrated to obtain the title compound (77 mg) having the following physical data.

TLC: Rf 0.63 (chloroform:methanol=9:1);
NMR (CDCl$_3$): δ 4.49, 5.18, 6.57, 7.14, 7.30, 7.67, 8.61.

Example 11

3-chloro-2-methyl-N-[2-(pyridin-3-ylmethoxy)-5-(trifluoromethyl)pyridin-3-yl]benzenesulfonamide

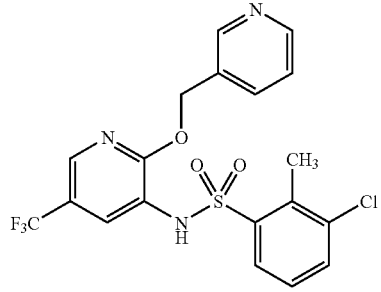

The compound of the present invention having the following physical data was obtained, using the compound prepared in Example 10 and 3-chloro-2-methylbenzenesulfonyl chloride, by the same procedure as a series of reactions of Example 5.

TLC: Rf 0.79 (chloroform:methanol=9:1);
NMR (d$_6$-DMSO): δ 2.62, 5.13, 7.33, 7.51, 7.70, 7.76, 8.47, 10.41.

Example 12

3-(phenylethynyl)-5-(trifluoromethyl)pyridin-2-amine

Under an atmosphere of argon, to a solution of 3-bromo-5-(trifluoromethyl)pyridin-2-amine (the compound described in *Bio. Org. Med. Chem.*, 9, 1715 (1999)) (163 mg) in triethylamine (1.5 mL), ethynylbenzene (82 μL), bis(triphenylphosphine)palladium dichloride (43 mg) and copper bromide (14 mg) were added. The reaction mixture was stirred for overnight at 60° C. To the reaction mixture, water was added and extracted with ethyl acetate. The extract was washed with a saturated aqueous solution of sodium chloride, dried with anhydrous magnesium sulfate and concentrated. The obtained residue was purified by column chromatography on silica gel (hexane:ethyl acetate=5:1) to give the title compound (26 mg) having the following physical data.

TLC: Rf 0.42 (hexane:ethyl acetate=3:1);
NMR (d$_6$-DMSO): δ 7.13, 7.42, 7.68, 7.90, 8.28.

Example 13

4-methyl-N-[3-(phenylethynyl)-5-(trifluoromethyl)pyridin-2-yl]benzenesulfonamide The compound of the present invention having the following physical data, using the compound prepared in Example 12 and p-toluenesulfonyl chloride, by the same procedure as a series of reactions of Example 5.

TLC: Rf 0.41 (hexane:ethyl acetate=3:1);
NMR (d$_6$-DMSO): δ 2.37, 7.39, 7.49, 7.67, 7.95, 8.30, 8.51, 11.21.

Example 14

N-[3-({4-chloro-3-[(1-methylpiperidin-4-yl)methoxy]benzyl}oxy)-5-methylpyrazin-2-yl]-4-methylbenzenesulfonamide

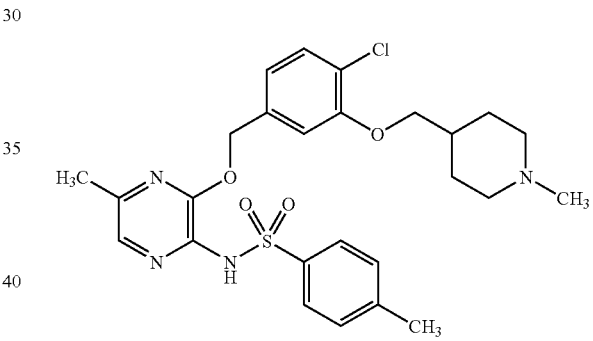

The title compound having the following physical data was obtained, using N-(3-bromo-5-methylpyradinmethylpyrazin-2-yl)-4-methylbenzenesulfonamide (the compound described in Reference Example 3 of WO04/007472) and {4-chloro-3-[(1-methylpiperidin-4-yl)methoxy]phenyl}methanol, by the same procedure as a series of reactions of Example 6.

Physical property: powder;
TLC: Rf 0.26 (chloroform:methanol=10:1);
NMR (d$_6$-DMSO): δ 1.65, 1.97, 2.26, 2.34, 2.72, 2.98, 3.39, 3.98, 5.33, 7.11, 7.32, 7.34, 7.43, 7.63, 7.82, 10.35.

Example 14(1)-14(7)

The following title compounds were obtained, using a corresponding bromo-compound instead of N-(3-bromo-5-methylpyrazin-2-yl)-4-methylbenzenesulfonamide and a corresponding alcohol compound instead of {4-chloro-3-[(1-methylpiperidin-4-yl)methoxy]phenyl}methanol, by the same procedure as a series of reactions of Example 14.

Example 14(1)

N-[3-({4-chloro-3-[(1-methylpiperidin-4-yl)methoxy]benzyl}oxy)-5-methylpyrazin-2-yl]-2-(trifluoromethyl)benzenesulfonamide Physical property: powder;
TLC: Rf 0.31 (chloroform:methanol=10:1);
NMR (d$_6$-DMSO): δ 1.63, 1.95, 2.28, 2.72, 2.96, 3.35, 3.97, 5.34, 7.09, 7.31, 7.42, 7.61, 7.82, 7.93, 8.21.

Example 14(2)

3-chloro-2-methyl-N-{5-methyl-3-[(2-methyl-1,2,3,4-tetrahydro-7-isoquinolinyl)methoxy]-2-pyrazinyl}benzenesulfonamide Physical property: powder;
TLC: Rf 0.56 (chloroform:methanol=10:1);
NMR (d$_6$-DMSO): δ 2.17, 2.52, 2.89, 3.79, 5.25, 7.15, 7.28, 7.33, 7.54, 7.87.

Example 14(3)

N-[5-bromo-3-({4-chloro-3-[(1-methyl-4-piperidinyl)methoxy]benzyl}oxy)-2-pyrazinyl]-4-methylbenzenesulfonamide Physical property: powder;
TLC: Rf 0.17 (chloroform:methanol=10:1);
NMR (d$_6$-DMSO): δ 1.62, 1.99, 2.35, 2.73, 2.96, 3.97, 5.33, 7.13, 7.34, 7.45, 7.83, 7.92.

Example 14(4)

N-[3-({4-chloro-3-[(1-methyl-4-piperidinyl)methoxy]benzyl}oxy)-2-pyrazinyl]-4-methylbenzenesulfonamide TLC: Rf 0.24 (chloroform:methanol=10:1);
NMR (d$_6$-DMSO): δ 1.65, 2.03, 2.35, 2.49, 2.71, 2.97, 3.97, 5.36, 7.10, 7.32, 7.36, 7.43, 7.74, 7.86, 10.56.

Example 14(5)

3-chloro-N-{3-[(3,5-dimethyl-1-phenyl-1H-pyrazol-4-yl)methoxy]-5-methyl-2-pyrazinyl}-2-methylbenzenesulfonamide Physical property: powder;
TLC: Rf 0.31 (hexane:ethyl acetate=1:1);
NMR (d$_6$-DMSO): δ 2.26, 2.28, 2.35, 2.61, 5.21, 7.45, 7.66, 7.93, 11.00.

Example 14(6)

3-chloro-2-methyl-N-{5-methyl-3-[(2-phenyl-1,3-thiazol-4-yl)methoxy]-2-pyrazinyl}benzenesulfonamide Physical property: amorphous;
TLC: Rf 0.76 (hexane:ethyl acetate=1:1);
NMR (d$_6$-DMSO): δ 2.30, 2.62, 5.50, 7.38, 7.51, 7.67, 7.93, 11.17.

Example 14(7)

tert-butyl 7-{[(6-bromo-3-{[(4-methylphenyl)sulfonyl]amino}-2-pyrazinyl)oxy]methyl}-3,4-dihydro-2(1H)-isoquinoline carboxylate Physical property: amorphous;
TLC: Rf 0.78 (hexane:ethyl acetate=1:1);
NMR (d$_6$-DMSO): δ 1.42, 2.35, 2.77, 3.54, 4.50, 5.30, 7.18, 7.34, 7.84, 7.92, 11.06.

Example 15

N-[5-bromo-3-(1,2,3,4-tetrahydro-7-isoquinolylmethoxy)-2-pyrazinyl]-4-methylbenzenesulfonamide hydrochloride To the compound prepared in Example 14 (7) (450 mg), 4 mol/L hydrogen chloride-ethyl acetate (20 mL) was added on an ice bath. The mixture was stirred for 45 minutes at room temperature. The reaction solution was diluted with methanol. To diethyl ether (225 mL), the solution was poured and stirred. The powder deposition was separated and dried to obtain the title compound (360 mg) having the following physical data.

TLC: Rf 0.11 (chloroform:methanol=10:1);
NMR (d$_6$-DMSO): δ 2.38, 3.04, 3.36, 4.25, 5.37, 7.24, 7.37, 7.86, 7.91, 9.74.

Example 16

N-[5-chloro-3-({3-[2-(dimethylamino)ethoxy]-4-methoxybenzyl}oxy)-2-pyridinyl]-2-methylbenzenesulfonamide The title compound having the following physical data was obtained, using 6-chloro[1,3]oxazolo[4,5-b]pyridin-2(3H)-one, 4-methylbenzenesulfonyl chloride and {3-[2-(dimethylamino)ethoxy]-4-methoxyphenyl}methanol, by the same procedure as a series of reactions of Example 1→Example 2.

Physical property: powder;
TLC: Rf 0.31 (ethyl acetate:methanol:triethylamine=20:2:1);
NMR (CDCl$_3$): δ 2.36, 2.39, 2.80, 3.88, 4.13, 4.94, 6.90, 7.06, 7.26, 7.78, 7.98.

Example 16(1)

3-chloro-N-[5-chloro-3-({3-[2-(dimethylamino)
ethoxy]-4-methoxybenzyl}oxy)-2-pyridinyl]-2-me-
thylbenzenesulfonamide The title compound having the following physical data was obtained, using 3-chloro-2-methylbenzenesulfonyl chloride instead of 4-methylbenzenesulfonyl chloride, by the same procedure as a series of reactions of Example 16.

Physical property: amorphous;

TLC: Rf 0.32 (chloroform:methanol=10:1);

NMR ($d_6$-DMSO): δ 2.60, 2.99, 3.75, 4.13, 5.08, 5.73, 6.96, 7.04, 7.20, 7.30, 7.38-7.42, 7.54, 7.58, 7.89.

Example 17

N-[2-{[(4-methylphenyl)sulfonyl]amino}-5-(trifluo-
romethyl)pyridin-3-yl]nicotinamide The title compound having the following physical data was obtained, using N-[3-amino-5-(trifluoromethyl)pyridin-2-yl]-4-methylbenzenesulfonamide and pyridin-3-carbonyl chloride instead of 4-methylbenzenesulfonyl chloride, by the same procedure as a series of reactions of Example 4.

TLC: Rf 0.36 (chloroform:methanol=10:1);

NMR ($d_6$-DMSO): δ 2.36, 7.37, 7.61, 7.90, 8.24, 8.34, 8.80, 9.15, 10.10, 11.18.

Biological Examples

It was demonstrated, for example, by the following experiments that the compound of the present invention represented by formula (I) has chemokine receptor-antagonistic activities (such as CCR4 and/or CCR5 antagonistic activity), inhibitory activity for effector cell functions and TNFα-regulating activity, and shows efficacy in animal disease models.

All the procedures were conducted by conventionally used method on the basis of basic biological methods. Furthermore, the measuring method of the present invention was modified to improve accuracy and/or sensitivity of the measurement for evaluating the compound of the present invention. The experimental method is explained in detail below.

Biological Example 1

Activity on Ca Ion Increase Stimulated by MDC 1-1: Isolation of Human CCR4 Gene

Human bone marrow cell cDNA was prepared using Marathon cDNA amplification kit (manufactured by Clontech). PCR primers hCCR4XbaI-F1 (SEQ ID NO:1) and hCCR4XbaI-R1 (SEQ ID NO:2) were designed based on the sequence of GenBankX85740.

Using the human bone marrow cell cDNA as the template and using Ex Taq (manufactured by Takara), a PCR reaction (2 minutes at 95° C.→[30 seconds at 95° C., 45 seconds at 60° C., 1 minute at 72° C.]×35 times) was carried out. The thus amplified PCR product was subjected to 1% agarose gel electrophoresis, purified using QIAquick Gel Extraction Kit (manufactured by QUIAGEN) and then digested with a restriction enzyme XbaI. The digested fragments were ligated to an expression vector pEF-BOS-bsr (*Nucleic acid Research,* 1990, Vol. 18, No. 17, p. 5322) using DNA Ligation Kit Ver. 2 (manufactured by Takara) and transformed into *Escherichia coli* DH5a. By preparing the resulting plasmid pEF-BOS-bsr/hCCR4, its DNA sequence was identified.

1-2: Culturing of CHO Cell

CHO-dhfr(−) was cultured using Ham's F-12 (containing fetal bovine serum (10%), penicillin (100 U/mL) and streptomycin (100 μg/mL)). Also, the transduced cell was cultured by adding blasticidin (5 μg/mL) to the above medium.

1-3: Transduction Into CHO Cell

The plasmid pEF-BOS-bsr/hCCR4 was transduced into the CHO-dhfr(−) cell using a DMRIE-C reagent (manufactured by Gibco BRL). After 48 hours, the medium was replaced with a medium containing 5 μg/mL blasticidin to carry out the selection, thereby establishing a stably overexpressing cell.

1-4: Inhibition Test on Activity of MDC Mediated by
CCR4 (Activity of MDC to Induce Transient
Increase of Ca Ions)

The thus established human CCR4 stably overexpressing CHO cell (CCR4/CHO cell) was suspended in Ham's F-12 medium and FBS (10%) and dispensed into a 96-well plate at $3.0 \times 10^4$ cells/well. One day after culturing at 37° C., the culture supernatant was discarded, and Ham's F-12 medium (containing Fura-2AM (5 μM), Probenecid (2.5 mM) and HEPES (20 mM; pH 7.4)) was dispensed at 80 μL/well to carry out incubation for 1 hour at 37° C. under shaded condition. After washing twice with 1× Hanks/HEPES (20 mM; pH 7.4) solution, the same solution was dispensed at 100 μL/well. Each of the test compounds was added to the thus Fura-2AM-incorporated CCR4/CHO cell, and 3 minutes thereafter, a recombinant human MDC (manufactured by PeproTach) diluted with 1× Hanks/HEPES (20 mM; pH 7.4) solution was added thereto to a final concentration of 10 nM. Transient increase in the intracellular $Ca^{2+}$ concentration induced by the human MDC was measured using a $Ca^{2+}$ detector for 96-well (manufactured by Hamamatsu Photonics), and inhibition ratio (%) of the test compound was calculated by the following equation:

Inhibition ratio=[(*Ec*−*Ea*)/*Ec*]×100

Ec: measured value of $Ca^{2+}$ transient increase by MDC; and

Ea: measured value of $Ca^{2+}$ transient increase by MDC when a test compound was added Inhibition ratio for each concentration of the compound was calculated, and the value ($IC_{50}$ value) indicating 50% inhibition ratio was determined from the inhibition curve.

As a result, the compounds of the invention showed an inhibition ratio of 50% or more at 10 μM. For Example, the compound of Example 2(2) showed an $IC_{50}$ value of 0.23 μM in the presence of 0.3% BSA, and the compound of Example 6(1) showed an $IC_{50}$ value of 0.08 μM in the presence of 0.3% BSA.

Biological Example 2

Activity on Cell Migration Stimulated by MDC 2-1: Inhibition Tests on MDC-Induced T Cell Strain
(CCRF-CEM Cell) Migration A medium (0.3 mL) containing or free of MDC (20 nM, manufactured by PeproTech) was added to the lower chamber of 24-transwell plate, and further a medium (0.3 mL) containing a test compound solution of 2-fold concentration (containing 0.02% dimethylsulfoxide (DMSO)) or a medium (0.3 mL) containing DMSO only was added thereto. To the upper chamber, CCRF-CEM cell suspension prepared in $1\times10^6$ cells/50μl and the test compound solution of 2-fold concentration (0.05 mL) were added. The test was initiated by superimpose the upper chamber on the lower chamber. The chambers were incubated in a carbon gas incubator (5% $CO_2$, 95% humidity) kept at 37° C. for 4 hours, and the cells remaining in the upper chamber were sucked up and removed. Then, 0.1 mL of a buffer (phosphate-buffered saline (PBS) containing ethylenediamine tetra-acetate sodium (EDTA) (20 μM) was added thereto, and subjected to reaction at 4° C. for 30 minutes. The transwell plate was centrifuged (1000 r.p.m.) for 5 minutes, and the incubation liquid (600 μL) in the lower chamber was collected, and the cell number was counted using Flow Cytometer (manufactured by Becton-Dickinson).

Migration inhibitory activity by the compound of the present invention was calculated by the following equation:

Inhibition ratio (%)=$[(A-B)/A]\times100$

A: Control value of the well to which the medium containing DMSO and not containing test compound was added; and B: Value of the well to which the medium containing DMSO and the test compound was added Inhibition ratio for each concentration of the compound was calculated, and the value ($IC_{50}$ value) indicating 50% inhibition ratio was determined from the inhibition curve.

Biological Example 3

Mouse Asthma Model 3-1: Mouse OVA-Induced Asthma Model

Ovalbumin (OVA, 0.2 mg/mL) and Alum (8 mg/mL) prepared in physiological saline were intraperitoneally administered (500 μL) to the mouse (male, C57BL/6) on Day 1 (test starting day) and Day 8 (1 week thereafter), to sensitize the mouse. On Days 15 to 21, the mouse was taken to an inhalation chamber (W: 240 mm×L: 240 mm×H: 120 mm), and a 2% OVA solution was sprayed with an ultrasonic wave type nebulizer (NE-U12, manufactured by Omron) for 20 minutes, to thus conduct induction. The compound of the present invention suspended in a medium, was administered orally at 30 minutes before OVA sensitization on Day 8 and at 30 minutes before OVA induction on Days 15 to 21. To the control group was administered only the medium. Three hours after OVA inhalation on Day 21, the mouse was exsanguinated, the catheter tube was inserted into the trachea, and the lung was washed with heparin-containing physiological saline (10 U/mL), to give a bronchoalveolar lavage fluid (BALF). Leukocyte number in BALF was counted using hemocyte counter (SF-3000, manufactured by Sysmex).

Biological Example 4

Mouse Dermatitis Model 4-1: Mouse DTH Model

The mouse (male, Balb/c) was shaved on the abdomen with hair clippers, and to the abdomen was applied ethanol solution (100 μL) of 7% (w/v) 2,4,6-trinitrochlrobenzene (TNCB), to sensitize the mouse. Seven days after sensitization, a 1% (w/v) TNCB solution in olive oil (20 μL) was applied to the auricle of the mouse (both sides of the right ear), to conduct induction. The compound of the present invention dissolved in a medium, was applied to both sides of the right ear (20 μL) 2 hours before applying TNCB. To the control groups, only the medium was applied. Right after the administration of the compound and 24 hours after TNCB application, the thickness of the mouse auricle was measured with Dialthickness gauge (manufactured by Ozaki Seisakusho), which was used as indicator for efficacy in mouse DTH model.

4-2: Mouse Dermatitis Model to Which Hapten is Applied

To the auricle (both sides of the right ear) of the mouse (male, Balb/c), 1% (w/v) TNCB solution (acetone:olive oil=4:1) (20 μL) was applied to conduct first sensitization. Seven days after sensitization, 1% (w/v) TNCB (acetone: olive oil=4:1) (20 μL) was applied to the mouse auricle, to conduct induction (Day 0). Furthermore, on Days 2, 4, 6, 8, 10, 12, 14 and 16, the same procedure as on Day 0 was repeated. The compound of the present invention was dissolved in a medium, applied to both sides of the right ear (20 μL) 2 hours before applying TNCB. To the control groups, was applied only the medium. Right after the administration of the compound and 24 hours after TNCB application, the thickness of the mouse auricle was measured with Dialthickness gauge (manufactured by Ozaki Seisakusho), which was used as indicator for efficacy in mouse dermatitis model to which hapten was continuously applied.

Experimental Example 5

Mouse TNFα Production Model 5-1: Mouse TNFα Production Model by LPS Stimulation

The present compound suspended in a medium, was orally applied to a mouse (male, C57BL/6), and after 0.5 hour, lipipolysaccharide (LPS, 055:B5, Sigma) was peritoneally administered to the mouse at a dose of 60 mg/kg. To the control groups was orally applied only the medium. Sixty minutes after LPS treatment, heparin-added blood collection was conducted from the abdominal vena cava under ether anesthesia, and centrifuged (12,000 r.p.m.) at 4° C. for 3 minutes, to give the plasma. The thus obtained plasma sample was stored at −80° C. before use. TNFα in the plasma was quantified using an ELISA kit (R&D systems).

Experimental Example 6

6-1: Inhibition Test on Activity of RANTES (Activity of RANTES to Induce Transient Increase of Ca Ions)

The thus established human CCR5 stably overexpressing CHO cell (CCR5/CHO cell) was suspended in Ham's F-12 medium (containing fetal bovine serum (10%), penicillin (100 U/mL) and streptomycin (100 μg/mL)) and dispensed into a 96-well plate at $3.0\times10^6$ cells/well. One day after culturing at 37° C., the culture supernatant was discarded, and Ham's F-12 medium (containing Fura-2AM (5 μM), Probenecid (2.5 mM) and HEPES (20 mM; pH 7.4)) was dispensed at 80 μL/well to carry out incubation for 1 hour at 37° C. under shaded condition. After washing twice with 1×

Hanks/HEPES (20 mM; pH 7.4) solution, the same solution was dispensed at 100 μL/well. Each of the test compounds was added to the thus Fura-2AM-incorporated CCR5/CHO cell, and 3 minutes thereafter, a recombinant human RANTES (manufactured by PeproTach) diluted with 1× Hanks/HEPES (20 mM; pH 7.4) solution was added thereto to a final concentration of 10 nM. Transient increase in the intracellular $Ca^{2+}$ concentration induced by the human RANTES was measured using a $Ca^{2+}$ detector for 96-well (manufactured by Hamamatsu Photonics), and inhibition ratio (%) of the test compound was calculated by the following equation:

Inhibition ratio=$[(Ec-Ea)/Ec]\times100$

Ec: measured value of $Ca^{2+}$ transient increase by RANTES; and

Ea: measured value of $Ca^{2+}$ transient increase by RANTES when a test compound was added As a result, the compounds of the invention showed an inhibition ratio of 50% or more at 10 μM.

Formulation Example 1

2-chloro-N-[3-({4-chloro-3-[(1-methylpiperidin-4-yl)methoxy]benzyl}oxy)-5-methylpyrazin-2-yl]-2-methylbenzenesulfonamide (100 g), Carboxymethylcellulose calcium (disintegrating agent) (20.0 g), Magnesium stearate (lubricating agent) (10.0 g) and Microcrystalline cellulose (870 g) were admixed in conventional method and punched out to obtain 10000 tablets each containing 10 mg of active ingredient.

Formulation Example 2

2-chloro-N-[3-({4-chloro-3-[(1-methylpiperidin-4-yl)methoxy]benzyl}oxy)-5-methylpyrazin-2-yl]-2-methylbenzenesulfonamide (200 g), mannitol (2 kg) and distilled water (50 L) were admixed in conventional method. The solution was sterilized in conventional manner, placed 5 mL portions into ampoules and freeze-dried to obtain 10000 ampoules each containing 20 mg of the active ingredient.

INDUSTRIAL APPLICABILITY

Since the compound of the present invention represented by formula (I) has a chemokine-receptor (especially CCR4 and/or CCR5) antagonistic activity, it is useful as a preventive and/or therapeutic agent for a disease which is mediated by chemokine receptor, namely chemokine receptor-mediated disease. Thus, the compound of the present invention is useful for medicament.

The invention claimed is:

1. A compound represented by formula (I-1) or (I-4):

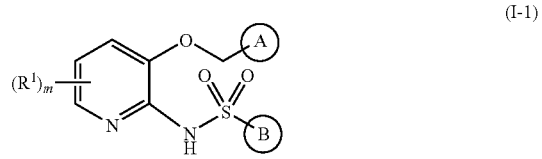

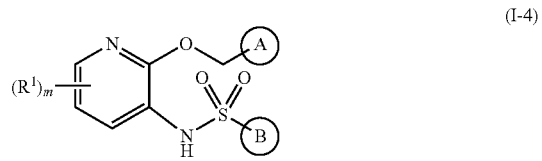

wherein $R^1$ is selected from the group consisting of halogen atom and methyl which may be substituted by 1 to 3 of halogen atom(s);

m is an integer from 0 to 2;

ring A is a benzene ring, a pyridine ring, a 3,4-dihydro-2H-1,4-benzoxaxazine ring, a 1,2,3,4-tetrahydro-1,8-naphthyridine ring, a quinoline ring, a 1,2,3,4-tetrahydroisoquinoline ring, a pyrazole ring or a thiazole ring which may be substituted by one to three substituent(s) selected from the group consisting of chlorine atom, methoxy, 2-(dimethylamino)ethoxy, piperidin-4-ylmethoxy, 1-methylpiperidin-4-ylmethoxy, methyl, t-butoxycarbonyl and phenyl;

ring B is a benzene ring which may be substituted by one or two substituent(s) selected from the group consisting of halogen atom and methyl which may be substituted by 1 to 3 of halogen atom(s), or a pharmaceutically acceptable salt thereof.

2. The compound according to claim 1, which is selected from the group consisting of N-[5-bromo-3-({3-[2-(dimethylamino)ethoxy]-4-methoxybenzyl}oxy)pyridin-2-yl]-4-methylbenzenesulfonamide;

N-[5-chloro-3-({3-[2-(dimethylamino)ethoxy]-4-methoxybenzyl}oxy)-2-pyridinyl]-4-methylbenzenesulfonamide and 3-chloro-N-[5-chloro-3-({3-[2-(dimethylamino)ethoxy]-4-methoxybenzyl}oxy)-2-pyridinyl]-2-methylbenzenesulfonamide.

3. A pharmaceutical composition which comprises a compound represented by formula (I-1) or (I-4):

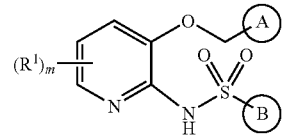

(I-1)

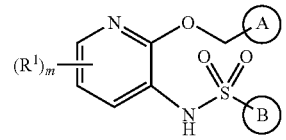

(I-4)

wherein all symbols have the same meanings as in claim 1, or a pharmaceutically acceptable salt thereof, and a pharmaceutically acceptable carrier.

* * * * *

SEQUENCE LISTING

```
<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: Chemically synthesized primer hCCR4XbaI-F1

<400> SEQUENCE: 1
ctagtctaga gacctgcctt gaggagcctg tagag                              35

<210> SEQ ID NO 2
<211> LENGTH: 35
<212> TYPE: DNA
<213> ORGANISM: Artificial Sequence
<220> FEATURE:
<223> OTHER INFORMATION: Chemically synthesized primer hCCR4XbaI-R1

<400> SEQUENCE: 2
ctagtctaga gttcattgac tctgcatttc accat                              35
```